United States Patent
Lu et al.

(10) Patent No.: US 9,439,884 B2
(45) Date of Patent: Sep. 13, 2016

(54) METHODS FOR THE TREATMENT OF IMMUNE DISORDERS

(75) Inventors: Kun Ping Lu, Newton, MA (US); Adrian Tun-Kyi, Boston, MA (US); Greg Finn, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 14/122,611

(22) PCT Filed: May 29, 2012

(86) PCT No.: PCT/US2012/039850
§ 371 (c)(1),
(2), (4) Date: Apr. 7, 2014

(87) PCT Pub. No.: WO2012/162968
PCT Pub. Date: Nov. 29, 2012

(65) Prior Publication Data
US 2014/0219957 A1  Aug. 7, 2014

Related U.S. Application Data

(60) Provisional application No. 61/490,338, filed on May 26, 2011.

(51) Int. Cl.
*A61K 31/07* (2006.01)
*A61K 31/203* (2006.01)
*A61K 45/06* (2006.01)

(52) U.S. Cl.
CPC ............ *A61K 31/203* (2013.01); *A61K 45/06* (2013.01)

(58) Field of Classification Search
CPC .......................... A61K 31/07; A61K 31/203
USPC ...................................................... 514/725
See application file for complete search history.

(56) References Cited

U.S. PATENT DOCUMENTS

| | | | |
|---|---|---|---|
| 5,952,467 A | 9/1999 | Hunter et al. | |
| 5,972,697 A | 10/1999 | Hunter et al. | |
| 6,462,173 B1 | 10/2002 | Lu et al. | |
| 6,495,376 B1 | 12/2002 | Lu et al. | |
| 6,596,848 B1 | 7/2003 | Hunter et al. | |
| 6,649,611 B2* | 11/2003 | Blumberg et al. | 514/235.8 |
| 7,125,677 B2 | 10/2006 | Hunter et al. | |
| 7,125,955 B2 | 10/2006 | Hunter et al. | |
| 7,148,003 B2 | 12/2006 | Hunter et al. | |
| 7,161,060 B1 | 1/2007 | Duff et al. | |
| 7,164,012 B2 | 1/2007 | Hunter et al. | |
| 8,129,131 B2 | 3/2012 | Lu et al. | |
| 8,258,099 B2 | 9/2012 | Lu et al. | |
| 2002/0025521 A1 | 2/2002 | Lu et al. | |
| 2005/0159485 A1* | 7/2005 | Jost-Price et al. | 514/559 |
| 2005/0239095 A1 | 10/2005 | Lu et al. | |
| 2006/0074222 A1 | 4/2006 | Lu et al. | |
| 2008/0118505 A1 | 5/2008 | Tedder | |
| 2008/0214470 A1 | 9/2008 | Lu et al. | |
| 2008/0248043 A1 | 10/2008 | Babcook et al. | |
| 2009/0258352 A1 | 10/2009 | Lu et al. | |
| 2010/0278832 A1 | 11/2010 | Kamogawa et al. | |
| 2011/0104756 A1 | 5/2011 | Rodriguez et al. | |
| 2012/0183560 A1 | 7/2012 | Akassoglou | |
| 2013/0028900 A1 | 1/2013 | Lu et al. | |
| 2014/0086909 A1 | 3/2014 | Lu et al. | |
| 2014/0242100 A1 | 8/2014 | Lu et al. | |

FOREIGN PATENT DOCUMENTS

| | | |
|---|---|---|
| WO | WO-97/17986 A1 | 5/1997 |
| WO | WO-99/09969 A1 | 3/1999 |
| WO | WO-02/065091 A2 | 8/2002 |
| WO | WO-02/092765 A2 | 11/2002 |
| WO | WO-2004/016751 A2 | 2/2004 |
| WO | WO-2004/101745 A2 | 11/2004 |
| WO | WO-2005/027727 A2 | 3/2005 |
| WO | WO 2008137488 A1 * | 11/2008 |
| WO | WO-2009/146218 A2 | 12/2009 |
| WO | WO-2013/185055 A1 | 12/2013 |
| WO | WO-2014/152157 A2 | 9/2014 |

OTHER PUBLICATIONS

International Search Report and Written Opinion for International Application No. PCT/US14/27017, mailed Oct. 28, 2014 (19 pages).
Nakamura, et al. "Proline isomer-specific antibodies reveal the early pathogenic tau conformation in Alzheimer's disease" Cell. 149(1):232-44 (2012).
U.S. Appl. No. 61/968,862, Lu et al.
Esnault et al., "Pin1 modulates the type 1 immune response," PLoS One. 2(2):e226 (2007).
International Search Report for International Application No. PCT/US2012/039850, mailed Oct. 3, 2012 (3 pages).
Jeong et al., "Novel role of Pin1 induction in type II collagen-mediated rheumatoid arthritis," J Immunol. 183(10):6689-97 (2009).
Written Opinion of the International Searching Authority for International Application No. PCT/US2012/039850, mailed Oct. 3, 2012 (5 pages).

(Continued)

*Primary Examiner* — Kevin E Weddington
(74) *Attorney, Agent, or Firm* — Clark & Elbing LLP; Kristina Bieker-Brady

(57) ABSTRACT

The invention features methods of treating an immune disorder characterized by elevated Pin1 marker levels in a subject by administering a retinoic acid compound. Additionally, the invention features methods of treating immune disorders (e.g., immune disorders characterized by elevated Pin1 marker levels) by administering a retinoic acid compound in combination with an anti-inflammatory, anti-viral, or anti-microbial compound.

20 Claims, 37 Drawing Sheets

(56) References Cited

OTHER PUBLICATIONS

Paneni et al., "Targeting prolyl-isomerase Pin1 prevents mitochondrial oxidative stress and vascular dysfunction: insights in patients with diabetes," Eur Heart J. 36(13): 817-28 (2015) (12 pages).

Shen et al., "The peptidyl-prolyl isomerase Pin1 regulates the stability of granulocyte-macrophage colony-stimulating factor mRNA in activated eosinophils," Nat Immunol. 6(12): 1280-7 (2005).

* cited by examiner 13-cis-retinoic acid (13cRA)

All-trans-retinoic acid (ATRA)

(Altucci et al. Nature Reviews Drug Discovery 6:793 (2007))

A. SAR studies

| Retinoids | Carboxylic group | % of Pin1 inhibition |
|---|---|---|
| pTide | --- | 100 |
| cis-RA | Yes | 24 |
| trans-RA | Yes | 41 |
| Retinol | No | 7 |
| Retinyl acetate | No | 5 |
| Retinal | No | 0 |
| AC-55649 | Yes | 18 |
| β-carotene | No | 0 |

B. Pin1-trans RA co-crystal

METHODS FOR THE TREATMENT OF IMMUNE DISORDERS

CROSS-REFERENCE TO RELATED APPLICATIONS

This application is the U.S. National Stage of PCT/US2012/039850, filed May 29, 2012, which, in turn, claims benefit of U.S. Provisional Application No. 61/490,338, filed May 26, 2011, each of which is incorporated by reference in its entirety.

STATEMENT AS TO FEDERALLY SPONSORED RESEARCH

This invention was made with government support under grant GM058556 awarded by NIH. The government has certain rights in the invention.

FIELD OF THE INVENTION

In general, the invention relates to the treatment of immune disorders (e.g., immune disorders characterized by elevated Pin1 marker levels) with retinoic acid compounds.

BACKGROUND OF THE INVENTION

Immune disorders are characterized by the inappropriate activation of the body's immune defenses. Rather than targeting infectious invaders, the immune response targets and damages the body's own tissues or transplanted tissues. The tissue targeted by the immune system varies with the disorder. For example, in multiple sclerosis, the immune response is directed against the neuronal tissue, while in Crohn's disease the digestive tract is targeted.

Immune disorders affect millions of individuals and include conditions such as asthma, allergic intraocular inflammatory diseases, arthritis, atopic dermatitis, atopic eczema, diabetes, hemolytic anaemia, inflammatory dermatoses, inflammatory bowel or gastrointestinal disorders (e.g., Crohn's disease and ulcerative colitis), multiple sclerosis, myasthenia gravis, pruritis/inflammation, psoriasis, rheumatoid arthritis, cirrhosis, and systemic lupus erythematosus.

A major cellular pathway in the pathogenesis of autoimmunity is the TLR/IRAK1/IRF/IFN pathway. For example, levels of IFNα (type I interferon) are elevated in patients with autoimmune diseases, including systemic lupus erythematosus (SLE), and are central to disease pathogenesis, correlating with autoantibodies and disease development. Recent genetic studies in SLE patients and lupus-prone mice have identified variants in the genes critical for the TLR/IRAK1/IRF/IFN pathways, including TLR7, IRAK1 and IRF5. In addition, several TLR inhibitors are in development for treatment of SLE. Notably, IRAK1 genetic variants have recently been identified in human SLE. IRAK1, a well-established pivotal player in TLRs and inflammation, is located on the X chromosome, which may help account for the fact that SLE is more common in women. Importantly, studies using mouse models, where the IRAK1 gene is removed, have demonstrated a key role for this kinase in the TLR7/9/IRF pathway that produces large quantities of IFNα in response to viral infection. Immune cells responsible for producing large quantities of IFNα are called pDCs. IRAK1 gene deletion prevents TLR dependent activation of IRF5/7 in pDCs and IFNα production. Significantly, autoantibody complexes obtained from SLE patients contain DNA and RNA and are taken up by pDCs to activate TLR7 and TLR9 leading to secretion of cytokines and IFNα. Moreover, TLR activation is known to inhibit activity of glucocorticoids, a frontline drug used to treat SLE. Although IRAK1 activity is regulated by phosphorylation upon TLR activation, little is known about whether it is subject to further control after phosphorylation and whether such regulation has any role in SLE.

The prevalence of asthma is increasing in the developed world, but the underlying mechanisms are not fully understood, and therapeutic modalities remain limited. Asthma is a chronic inflammatory disease of the airways that is induced by overexpression of multiple proinflammatory genes regulated by various signal pathways in response to exposure to any of numerous allergens, including Toll-like receptor/interleukin-1 receptor (TLR/IL-1R) signaling activated by house dust mite (HDM) allergens and IL-33, respectively. A major regulatory mechanism in these signal pathways and gene activation is Pro-directed phosphorylation (pS/T-P), but until recently little was known about whether and how they are regulated following phosphorylation.

Current treatment regimens for immune disorders typically rely on immunosuppressive agents. The effectiveness of these agents can vary and their use is often accompanied by adverse side effects. Thus, improved therapeutic agents and methods for the treatment of autoimmune disorders are needed.

SUMMARY OF THE INVENTION

In one aspect, the invention provides a method of treating an immune disorder in a subject by administering a retinoic acid compound to the subject in an amount sufficient to treat the subject, wherein the subject is determined to have elevated levels of a Pin1 marker (e.g., Ser71 phosphorylation) prior to the administration.

In another aspect, the invention features a method of treating an immune disorder in a subject by determining Pin1 marker levels (e.g., reduced Ser71 phosphorylation) in a sample (e.g., tumor samples, blood, urine, biopsies, lymph, saliva, phlegm, and pus) from the subject and administering a retinoic acid compound to the subject if the sample is determined to have elevated Pin1 marker levels.

In any of the foregoing aspects, the method can also include the administration of a second therapeutic compound (e.g., at a low dosage). The second compound can be administered separately, or in a single formulation with the retinoic acid compound. The second compound can be, e.g., an anti-inflammatory, anti-microbial, or anti-viral compound. Additionally, or alternatively, any one of the foregoing methods can include determining Pin1 marker levels in the sample after the administration of a retinoic acid compound.

In any of the foregoing aspects, the retinoic acid compound may be selected from 13-cis-retinoic acid, all-trans-retinoic acid, retinol, retinol acetate, retinal, AC-55649, or any of the compounds listed in FIG. 9B.

The elevated Pin1 marker level of any of the foregoing methods can be due to, e.g., an inherited trait or a somatic mutation.

The immune disorder of any of the foregoing methods can, e.g., result from disregulation of Toll-like receptor signaling or type I interferon-mediated immunity, including acne vulgaris; acute respiratory distress syndrome; Addison's disease; adrenocortical insufficiency; adrenogenital ayndrome; allergic conjunctivitis; allergic rhinitis; allergic intraocular inflammatory diseases, ANCA-associated small-vessel vasculitis; angioedema; ankylosing spondylitis; aphthous stomatitis; arthritis, asthma; atherosclerosis; atopic dermatitis; autoimmune disease; autoimmune hemolytic anemia; autoimmune hepatitis; Behcet's disease; Bell's palsy; berylliosis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; epicondylitis; erythema nodosum; exfoliative dermatitis; fibromyalgia; focal glomerulosclerosis; giant cell arteritis; gout; gouty arthritis; graft-versus-host disease; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflammatory bowel or gastrointestinal disorders, inflammatory dermatoses; juvenile rheumatoid arthritis; laryngeal edema; lichen planus; Loeffler's syndrome; lupus nephritis; lupus vulgaris; lymphomatous tracheobronchitis; macular edema; multiple sclerosis; musculoskeletal and connective tissue disorder; myasthenia gravis; myositis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary billiary cirrhosis; pruritus scroti; pruritis/inflammation, psoriasis; psoriatic arthritis; Reiter's disease; relapsing polychondritis; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis.

By the term "immune disorder" is meant a disorder characterized by deregulation of Toll like receptor and/or type 1 interferon.

As used herein, the term "Pin1 marker" refers to a marker which is capable of being indicative of Pin1 activity levels in an organism or a sample of the invention. Pin1 markers include nucleic acid molecules (e.g., mRNA, DNA) which correspond to some or all of a Pin1 gene, peptide sequences (e.g., amino acid sequences) which correspond to some or all of a Pin1 protein, nucleic acid sequences which are homologous to Pin1 gene sequences, peptide sequences which are homologous to Pin1 peptide sequences, antibodies to Pin1 protein, substrates of Pin1 protein, binding partners of Pin1 protein, and activity of Pin1.

By "elevated levels of a Pin1 marker" is meant a level of Pin1 marker that is altered thereby indicating elevated Pin1 activity. "Elevated levels of a Pin1 marker" include levels at least 5%, 6%, 7%, 8%, 9%, 10%, 15%, 20%, 25%, 30%, 40%, 50%, 60%, 70%, 80%, 90%, 100%, 200%, 500%, 1000%, or greater than, or 5%, 6%, 7%, 8%, 9%, 10%, 15%, 20%, 25%, 30%, 40%, 50%, 60%, 70%, 80%, 90%, 100% less than the marker levels measured in a normal, disease fee subject or tissue.

By the term "retinoic acid compound" is meant a compound that is either (a) the diterpene retinoic acid, or a derivative thereof, or (b) a compound having the structure $R^1—Ar^1-L^1Ar^2-L^2-C(=O)R^3$ (Formula (I)). Exemplary retinoic acid compounds described herein include the compounds identified in FIGS. 9A-9C. The term "diterpene retinoic acid" encompasses any stereoisomer of retinoic acid (e.g., the retinoic acid may be in the all-trans configuration (ATRA) or one or more of the double bonds may be in the cis configuration (e.g., 13-cis retinoic acid (13cRA)). Derivatives of the diterpene retinoic acid include reduced forms such as retinal, retinol, and retinyl acetate. In Formula (I), each of $Ar^1$ and $Ar^2$ is, independently, optionally substituted aryl or an optionally substituted heteroaryl; $R^1$ is H, an optionally substituted alkyl group, an optionally substituted alkenyl group, or an optionally substituted alkynyl group; each of $L^1$ and $L^2$ is selected, independently from a covalent bond, an optionally substituted $C_{1-10}$ alkylene, an optionally substituted $C_{2-10}$ alkenylene (e.g., —CH=CH—, —COCH=CH—, —CH=CHCO—, a dienyl group, or a trienyl group), optionally substituted $C_{2-10}$ alkynylene (e.g., —C≡C—), or —(CHR$^4$)$_n$CONR$^5$—, —NR$^5$CO—, where n is 0 or 1, $R^4$ is H or OH, and $R^5$ is H or optionally substituted alkyl; and $R^3$ is H, OR$^4$ or N(R$^4$)$_2$, where each $R^4$ is selected, independently, from H, optionally substituted alkyl, or optionally substituted heteroalkyl.

The term "aryl," as used herein, represents a mono- or bicyclic $C_6$-$C_{14}$ group with [4n+2]π electrons in conjugation and where n is 1, 2, or 3. Aryl groups also include ring systems where the ring system having [4n+2]π electrons is fused to a non-aromatic cycloalkyl or a non-aromatic heterocyclyl. Phenyl is an aryl group where n is 1. Aryl groups may be unsubstituted or substituted with, e.g., 1, 2, 3, or 4 substituent groups as defined herein. Still other exemplary aryl groups include, but are not limited to, naphthyl, 1,2-dihydronaphthyl, 1,2,3,4-tetrahydronaphthyl, fluorenyl, indanyl, and indenyl.

The term "cycloalkyl," as used herein, represents a monovalent saturated or unsaturated non-aromatic cyclic hydrocarbon group from three to ten carbons, unless otherwise specified, and is exemplified by cyclopropyl, cyclobutyl, cyclopentyl, cyclohexyl, cycloheptyl, bicyclo[2.2.1.]heptyl, and the like. In some embodiments, the cycloalkyl is a polycyclic (e.g., adamantyl). Cycloalkyl groups may be unsubstituted or substituted with, e.g., 1, 2, 3, or 4 substituent groups as defined herein.

The term "heteroaryl," as used herein, represents an aromatic (i.e., containing 4n+2 pi electrons within the ring system) 5- or 6-membered ring containing one, two, three, or four heteroatoms independently selected from the group consisting of nitrogen, oxygen, and sulfur, as well as bicyclic, tricyclic, and tetracyclic groups in which any of the aromatic ring is fused to one, two, or three heterocyclic or carbocyclic rings (e.g., an aryl ring). Exemplary heteroaryls include, but are not limited to, furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, isoxazole, isothiazole, pyrazole, thiazole, triazole (e.g., 1,2,4-triazole or 1,2,3-triazole), pyridine, pyrimidine, pyrazine, pyrazine, triazine (e.g, 1,2,3-triazine 1,2,4-triazine, or 1,3,5-triazine), 1,2,4,5-tetrazine, indolyl, quinolinyl, isoquinolinyl, benzimidazolyl, benzothiazolyl, and benzoxazolyl. Heteroaryls may be unsubstituted or substituted with, e.g., 1, 2, 3, or 4 substituents groups as defined herein.

The term "heterocyclyl," as used herein represents a non-aromatic 5-, 6- or 7-membered ring, unless otherwise specified, containing one, two, three, or four heteroatoms independently selected from the group consisting of nitrogen, oxygen, and sulfur. Heterocyclyl groups may be unsubstituted or substituted with, e.g., 1, 2, 3, or 4 substituent groups as defined herein.

Where a group is substituted, the group may be substituted with 1, 2, 3, 4, 5, or 6 substituent groups. Optional substituent groups include, but are not limited to: $C_{1-6}$ alkyl, $C_{2-6}$ alkenyl, $C_{2-6}$ alkynyl, aryl, heteroaryl, cycloalkyl, heterocyclyl, halogen (—F, —Cl, —Br, or —I), azido (—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2H$), carboxylic ester (—$CO_2R'$), carbamoyl (—OC(=O)NR'R" or —NRC(=O)OR'), hydroxy (—OH), oxo (=O), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, aryl, or heteroaryl. In some embodiments, the substituent groups themselves may be further substituted with, for example, 1, 2, 3, 4, 5, or 6 substituents as defined herein. For example, a $C_{1-6}$ alkyl, aryl, or heteroaryl group may be further substituted with 1, 2, 3, 4, 5, or 6 substituents as described herein.

The retinoic acid compounds of the invention inhibit Pin1 activity (e.g., as determined by the fluorescence polarization-based displacement assay or PPIase assay as describe herein). This inhibition can be, e.g., greater than 20%, 30%, 40%, 50%, 60%, 70%, 80%, 90%, 95%, 99%, or greater.

By "corticosteroid" is meant any naturally occurring or synthetic steroid hormone which can be derived from cholesterol and is characterized by a hydrogenated cyclopentanoperhydrophenanthrene ring system. Naturally occurring corticosteroids are generally produced by the adrenal cortex. Synthetic corticosteroids may be halogenated. Functional groups required for activity include a double bond at Δ4, a C3 ketone, and a C20 ketone. Corticosteroids may have glucocorticoid and/or mineralocorticoid activity. In preferred embodiments, the corticosteroid is either fludrocortisone or prednisolone.

Exemplary corticosteroids include algestone, 6-alpha-fluoroprednisolone, 6-alpha-methylprednisolone, 6-alpha-methylprednisolone 21-acetate, 6-alpha-methylprednisolone 21-hemisuccinate sodium salt, 6-alpha,9-alpha-difluoroprednisolone 21-acetate 17-butyrate, amcinafal, beclomethasone, beclomethasone dipropionate, beclomethasone dipropionate monohydrate, 6-beta-hydroxycortisol, betamethasone, betamethasone-17-valerate, budesonide, clobetasol, clobetasol propionate, clobetasone, clocortolone, clocortolone pivalate, cortisone, cortisone acetate, cortodoxone, deflazacort, 21-deoxycortisol, deprodone, descinolone, desonide, desoximethasone, dexamethasone, dexamethasone-21-acetate, dichlorisone, diflorasone, diflorasone diacetate, diflucortolone, doxibetasol, fludrocortisone, flumethasone, flumethasone pivalate, flumoxonide, flunisolide, fluocinonide, fluocinolone acetonide, 9-fluorocortisone, fluorohydroxyandrostenedione, fluorometholone, fluorometholone acetate, fluoxymesterone, flupredidene, fluprednisolone, flurandrenolide, formocortal, halcinonide, halometasone, halopredone, hyrcanoside, hydrocortisone, hydrocortisone acetate, hydrocortisone butyrate, hydrocortisone cypionate, hydrocortisone sodium phosphate, hydrocortisone sodium succinate, hydrocortisone probutate, hydrocortisone valerate, 6-hydroxydexamethasone, isoflupredone, isoflupredone acetate, isoprednidene, meclorisone, methylprednisolone, methylprednisolone acetate, methylprednisolone sodium succinate, paramethasone, paramethasone acetate, prednisolone, prednisolone acetate, prednisolone metasulphobenzoate, prednisolone sodium phosphate, prednisolone tebutate, prednisolone-21-hemisuccinate free acid, prednisolone-21-acetate, prednisolone-21(beta-D-glucuronide), prednisone, prednylidene, procinonide, tralonide, triamcinolone, triamcinolone acetonide, triamcinolone acetonide 21-palmitate, triamcinolone diacetate, triamcinolone hexacetonide, and wortmannin. Desirably, the corticosteroid is fludrocortisone or prednisolone.

"Treatment," as used herein, refers to the application or administration of a therapeutic agent (e.g., a retinoic acid compound) to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease, or to slow the progression of the disease.

As used herein, the terms "sample" and "biological sample" include samples obtained from a mammal or a subject containing Pin1 which can be used within the methods described herein, e.g., tissues, cells and biological fluids isolated from a subject, as well as tissues, cells and fluids present within a subject. Typical samples from a subject include tissue samples, tumor samples, blood, urine, biopsies, lymph, saliva, phlegm, pus, and the like.

By a "low dosage" or "low concentration" is meant at least 5% less (e.g., at least 10%, 20%, 50%, 80%, 90%, or even 95%) than the lowest standard recommended dosage or lowest standard recommended concentration of a particular compound formulated for a given route of administration for treatment of any human disease or condition. For example, a low dosage of an anti-inflammatory, anti-microbial, or anti-viral compound formulated for oral administration will differ from a low dosage of an anti-inflammatory, anti-microbial, or anti-viral compound formulated for intravenous administration.

(a-c) Impaired TLR7/9-induced cytokine production from Pin1 KO mDCs. Bone-marrow-derived mDCs were stimulated with 100 ng/mL, LPS, 1 μg/mL Pam3CSK4, 0.1 μg/mL R848 or 0.1 μM CpG-B. Levels of IL-6 (a), IL-12p40 (b), TNFα (c) measured in cell-culture supernatants after 12 h are shown.

(d, e) IFN-α levels in supernatants after R848 and CpG-A treatment of purified splenic pDCs (B220$^+$/CD11c$^{int}$) (d) and Flt3L-induced bone-marrow-derived pDCs for 24 h (e).

(f, g) IFN-α levels in supernatants following stimulation of splenic (f) and Flt3L-induced bone-marrow-derived pDCs (g) for 24 h with Influenza A (H1N1) virus or MCMV. IFN-α concentrations were measured by ELISA. Bars indicate means±s.d. of triplicate determinations.

(h) Splenic pDCs were stimulated with PBS, R848 or CpG DNA for 6 h. Expression of IFN-α or β mRNAs was measured by quantitative real-time RT-PCR analysis. Data were normalized to the levels of GAPDH expression in means±s.d. of triplicates.

(i) Pin1 catalytic activity, but not protein level, is increased upon TLR7/9 stimulation. Purified human PBMC were treated for 30 min either with PBS (blue), R848 (black) or CpG DNA (red) and lysed, followed by protease-coupled isomerase activity assay for Pin1 activity. Results are representative of 3 independent experiments. Following the Pin1 protease coupled isomerase activity assay, fractions of lysates were subjected to immunoblotting analysis using Pin1 antibody with tubulin as a control (inset).

Figure 2:
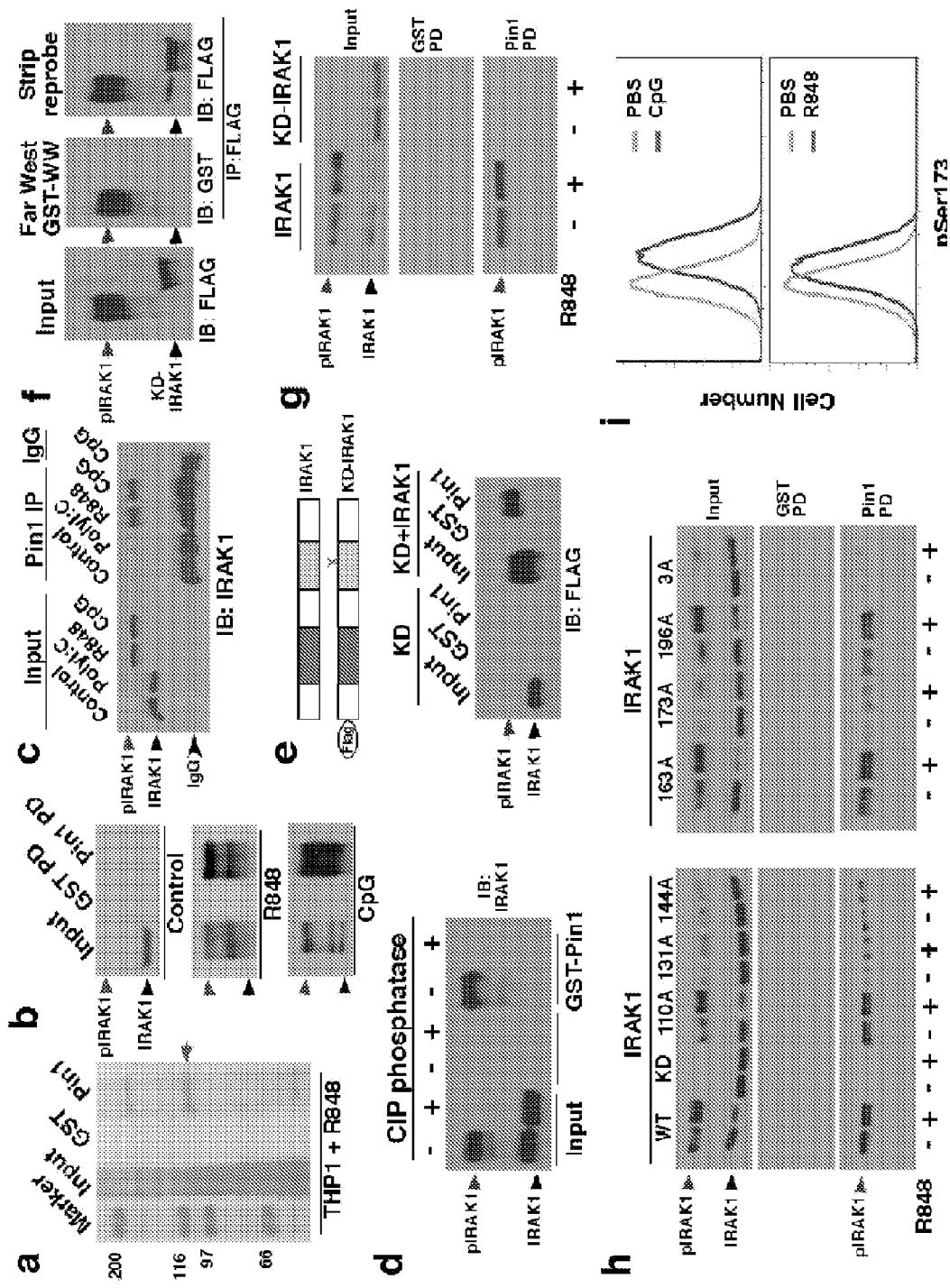

FIG. 2: Proteomic approach identifies IRAK1 as a major Pin1 substrate upon TLR stimulation.

(a) Proteomic identification of IRAK1 as a TLR-induced Pin1 binding protein. THP1 cells stimulated with R848 for 45 min were lysed and subjected to GST-Pin1 pulldown followed by SDS-PAGE and colloidal CBB staining Specific GST-Pin1 interacting bands were excised and 7 peptides were identified to IRAK1 by LC-MS (FIG. 12A).

(b) TLR-dependent interaction between Pin1 and IRAK1, assayed by GST-Pin1 pulldown. RAW264.7 cells stimulated with PBS or either R848 or CpG for 30 min were subjected to immunoblotting analysis using IRAK1 antibodies after pull down with GST or GST-Pin1.

(c) TLR-dependent interaction between endogenous Pin1 and TRAM, assayed by Co-IP. THP1 cells were stimulated with poly(I:C), R848 or CpG and subjected to immunoprecipitation with anti-Pin1 antibodies or control IgG, followed by immunoblotting with IRAK1 antibodies.

(d) The IRAK1-Pin1 interaction is sensitive to phosphatase treatment. TLR7-HEK293T cells were transfected with FLAG-IRAK1 and stimulated with R848 and lysates were untreated or treated with CIP phosphatase for 60 min at 30° C., followed by GST-Pin1 pulldown experiments.

(e) The Pin1-IRAK1 interaction is dependent on the intrinsic kinase activity of IRAK1. FLAG-KD-IRAK1, either alone or in combination with IRAK1 were expressed in IRAK1-deficient 293T cells, followed by GST pulldown experiments (f) Pin1 binds directly to phosphorylated WT IRAK1, but not KD IRAK1. FLAG-IRAK1 and FLAG-KD IRAK1 were expressed in IRAK1-deficient 293T cells and purified using FLAG-agarose, followed by Far-Western analysis using GST-Pin1 WW domain to detect Pin1 binding using anti-GST antibody. Membranes were re-probed with FLAG antibody as a control.

(g) Pin1 binds to activated WT IRAK1, but not KD IRAK1 in MEFs. FLAG-IRAK1 and its KD mutant were expressed in MEFs using retroviral infection and then treated with R848 or control buffer, followed by GST pulldown experiments.

(h) Multiple pSer-Pro motifs in the undetermined domain (UD) of IRAK1 are required for Pin1 binding. FLAG-IRAK1 and its mutants were expressed in MEFs using retroviral infection, and then treated with R848 or control buffer, followed by GST pull down experiments.

(i) S173 phosphorylation of IRAK1 is induced upon TLR7/9 stimulation.

Figure 3:
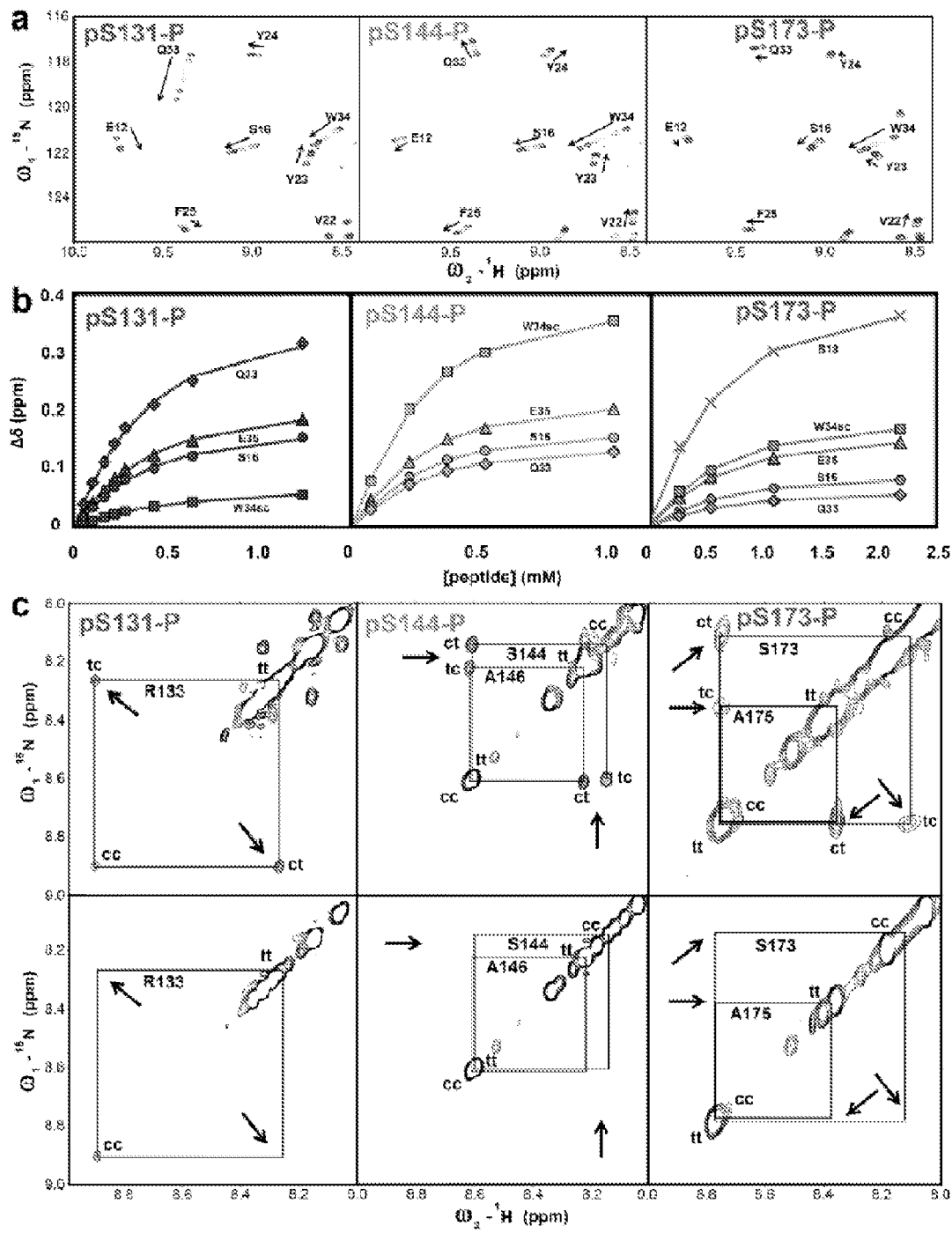

FIG. 3: Phosphorylated S131/S144/S173-Pro sites in the IRAK-1 UD bind and are isomerized by Pin1

(a) Representative chemical shift perturbations in $^{15}$N-WW detected using 2D $^{15}$N-$^{1}$H HSQC spectra resulting from titration with IRAK-1 peptides phosphorylated at Ser131. Ser144, and Ser173. Apo peaks are shown in red, and sequential colors represent increasing concentrations of peptides, purple being highest.

(b) Representative binding curves for WW domain residues, showing weighted chemical shift changes ($\Delta\delta$=sqrt $[\Delta\delta_{1H}^2+(0.154\Delta\delta_{15N})^2]$) as a function of total concentration of peptide. Residues plotted are Ser16 (●), Ser18 (x), Gln33 (♦), the sidechain of Trp34 (■), and Glu35 (▲). Lines represent global fits.

(c) 2D $^{1}$H-$^{1}$H ROESY spectra (mixing time of 100 ms) of IRAK-1 phosphopeptides in the presence (top panels) or absence (bottom panels) of a catalytic amount of Pin1. The appearance of exchange crosspeaks (arrows) between peaks corresponding to the cis and trans isomers confirms that Pin1 acts catalytically on these sequences.

Figure 4:
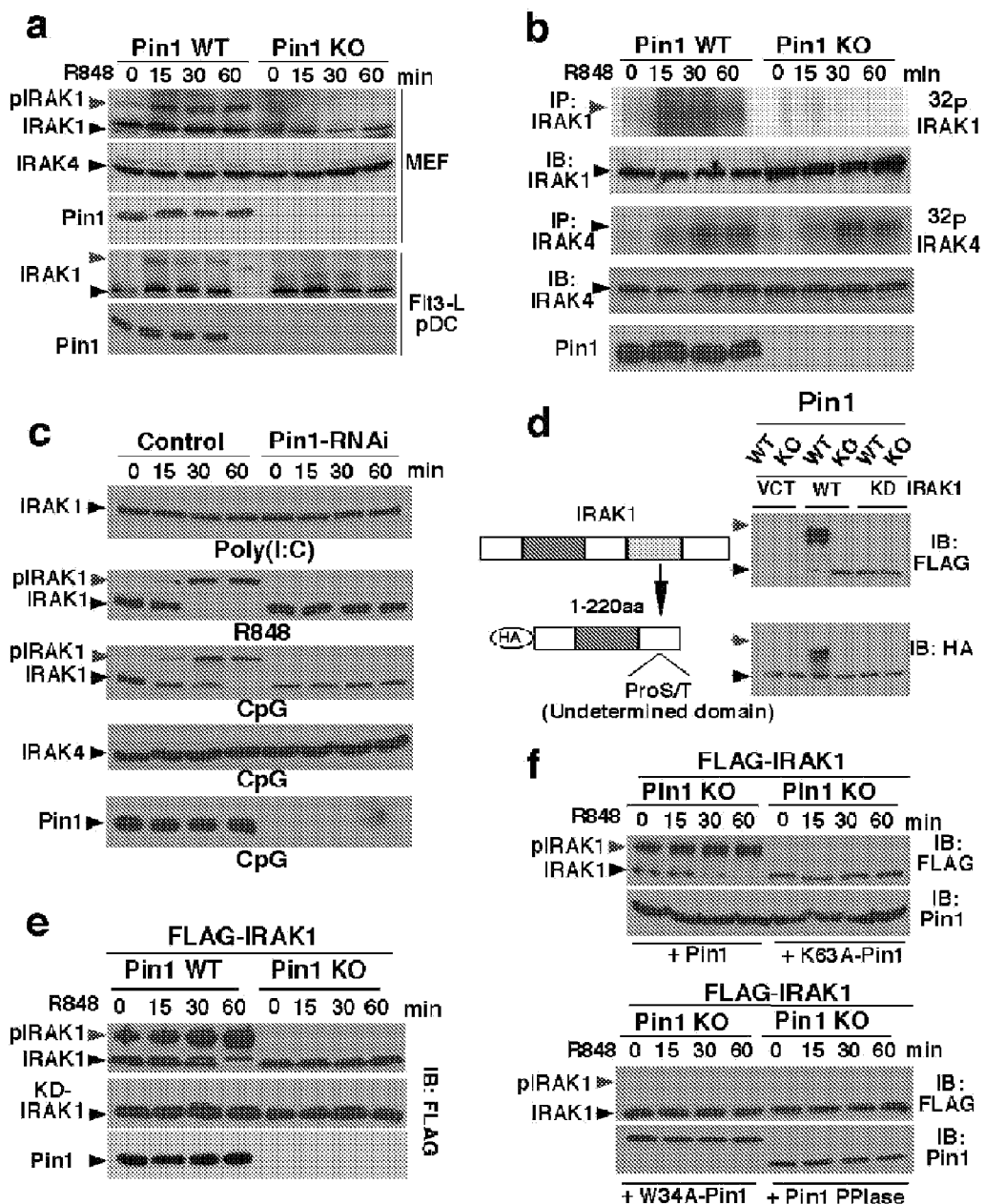

FIG. 4 Pin1 is essential for IRAK1 activation upon TLR ligation.

(a) Pin1 KO completely blocks IRAK1 activation in mouse cells following TLR7 stimulation. Pin1 WT and KO Flt3-derived pDCs (bottom) or TLR7-expressing MEF cells (top) were simulated with R848 for the indicated times and analyzed for the characteristic IRAK1 shift by immunoblotting with IRAK1 antibodies, with IRAK4 and Pin1 levels as controls.

(b) Pin1 KO completely blocks activation of IRAK1, but not IRAK4 following TLR7 stimulation. Peritoneal macrophage from Pin1 WT and KO mice were stimulated with R848 for the indicated times and kinase activity of IRAK1 and IRAK4 was assessed by IP kinase autophosphorylation assay. Protein levels of IRAK1, IRAK4 and Pin1 were assayed as controls.

(c) Pin1 knockdown blocks IRAK1 activation in human cells following TLR7 and TLR9, but not TLR3 stimulation. Human THPI monocytes were infected with viral control shRNA or shRNA targeting Pin1 and simulated with poly (I:C) (TLR3), R848 or CpG ligands for the indicated times, followed by analyzing the characteristic IRAK1 shift using immunoblotting.

(d) In vivo kinase assay demonstrates IRAK1 kinase activity in Pin1 WT, but not Pin1 KO cells. Retroviral FLAG-IRAK1, and KO-IRAK1 or vector (VCT) control were coexpressed with a HA-N-terminal 220 aa fragment of IRAK1 as a substrate in Pin1 WT and KO MEFs (schematic diagram). IRAK1 kinase activity was determined by immunoblotting with HA antibodies to assess the characteristic mobility shift in IRAK1 N-terminal 220aa due to trans-phosphorylation by co-expressed IRAK1 proteins.

(e) Pin1 KO abolishes TLR dependent activation of exogenous IRAK1 in vivo. FLAG-IRAK1 and its KO mutant were co-expressed with TLR7 in Pin1 WT and KO MEF cells using retroviral vectors and stimulated with R848 for the indicated times, followed by analyzing the characteristic IRAK1 mobility shift using immunoblotting.

(f) Pin1, but not its WW domain-binding mutant (W34A) or catalytically inactive PPIase domain mutant (K63A), fully rescues IRAK1 activation in Pin1 KO cells. Pin1 KO cells stably expressing FLAG-IRAK1 were transfected with either WT-Pin1, K63A-Pin1, W34A-Pin1 or PPIase domain of Pin1 and TLR7 and stimulated for the indicated times, followed by analyzing the characteristic IRAK1 mobility shift using immunoblotting.

Figure 5:
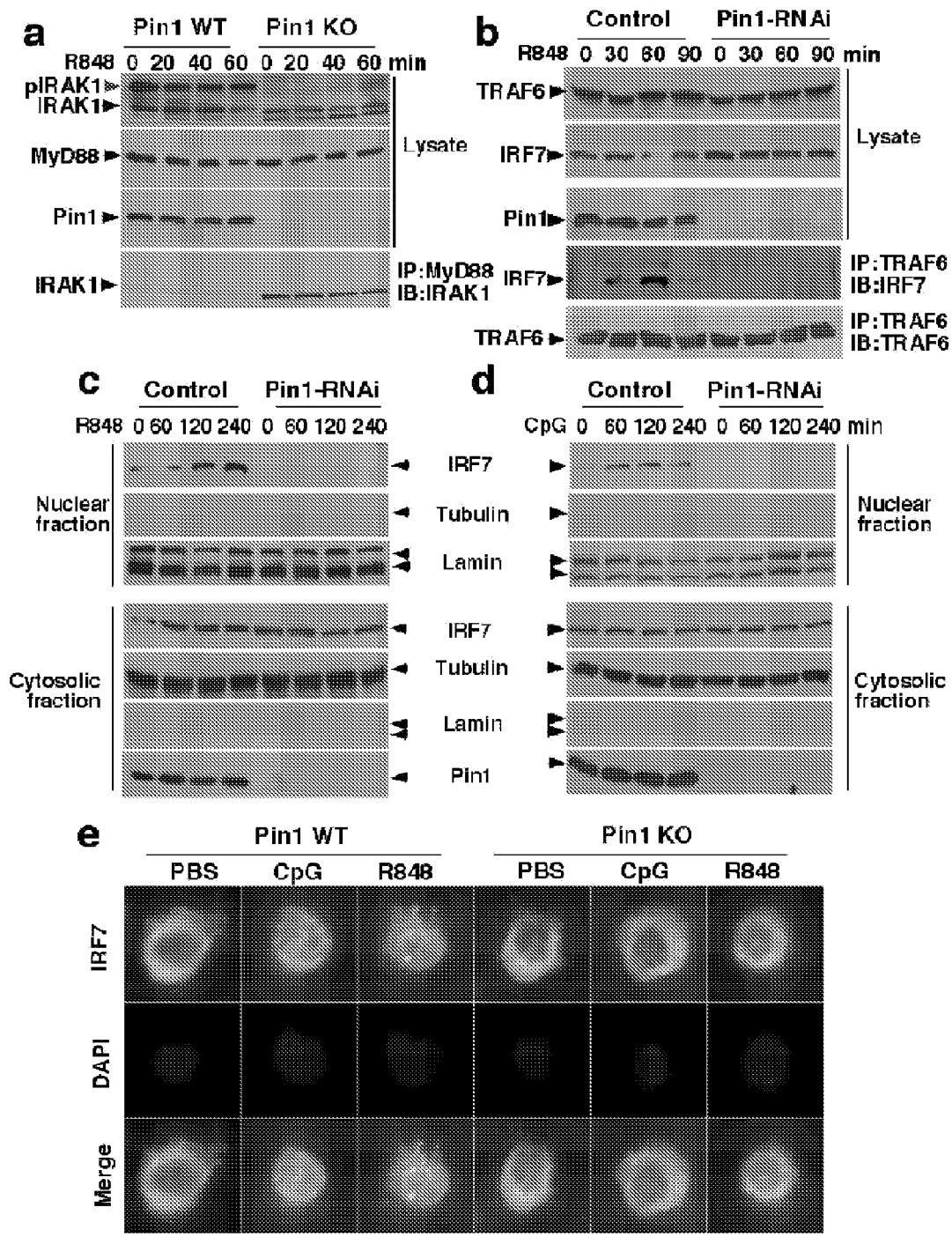

FIG. 5 Pin1 facilitates IRAK1 release from the receptor complex to activate IRF7 following TLR ligation.

(a) Activated and phosphorylated IRAK1 is released from MyD88 in Pin1 WT cells, but inactive IRAK1 is not in Pin1 KO cells. HA-MyD88 and FLAG-IRAK1 were co-expressed in Pin1 WT and KO MEF using retroviral expression vectors, followed by immunoprecipitation with anti-HA antibody and then immunoblotting with anti-FLAG antibody.

(b) Pin1 knockdown inhibits the interaction of IRF7 with TRAF6. THPI cells expressing Pin1-RNAi or control RNAi were stimulated with CpG for the indicated times and the interaction of IRF7 and TRAF6 was examined by Co-IP.

(c, d) Pin1 knockdown prevents IRF7 nuclear translocation in human THPI cells. Following TLR7 (c) or TLR9 (d) ligation for the indicated times, nuclear and cytoplasmic fractions of THPI cells were prepared, followed by immunoblotting with IRF7 antibody. The purity of nuclear and cytosolic fractions was evaluated by immunoblotting with tubulin or lamin A/C antibodies, respectively.

(e) Pin1 KO prevents IRF7 nuclear translocation after TLR7 or TLR9 ligation in pDCs. After R484 or CpG stimulation, Pin1 WT and KO pDCs were immunostained with IRF7 antibodies and counter-stained with DAPI, followed by confocal microscopy.

Figure 6:
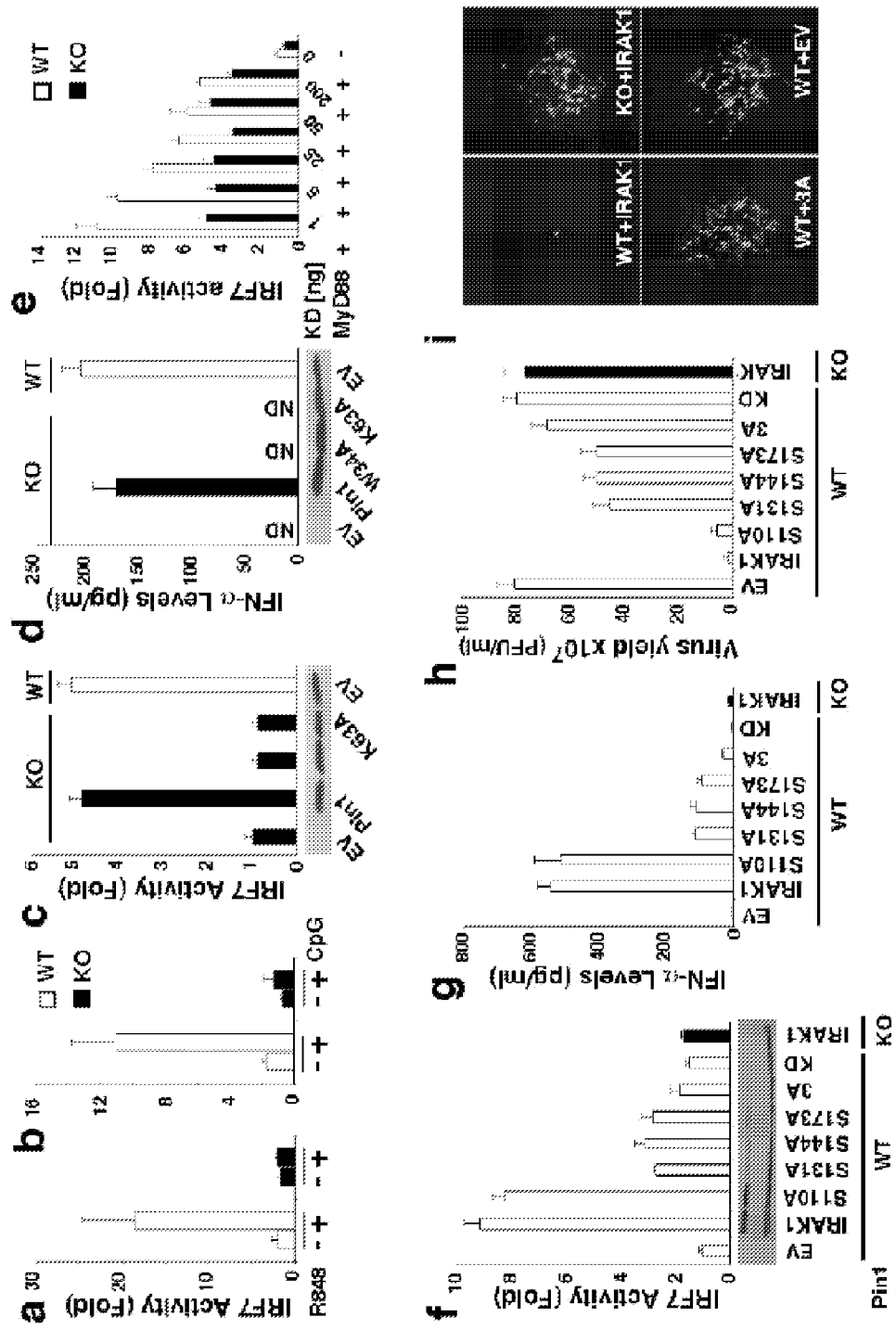

FIG. 6 Pin1 is required for IRF7 activation and IFN-α production upon TLR ligation in vitro.

(a, b) Pin1 is required for IRF7 activation in response to TLR7/9 activation. Pin1 WT and KO cells transiently co-expressing a $UAS_{(GAL)}$-reporter plasmid, Gal4-IRF7 and TLR7 (a) or TLR9 (b) were stimulated with R848 or CpG, respectively, followed by luciferase assay 12 h later using renilla luciferase to normalize for transfection efficiency.

(c, d) Re-expression of Pin1, but not its mutants, fully rescues impaired IRF7 activation and IFN-α production in Pin1 KO cells. Pin1 WT and KO MEFs stably expressing IRAK1 were transiently co-transfected with $UAS_{(GAL)}$ and Gal4-IRF7 and empty vector (EV), Pin1, WW domain mutant (W34A) or PPIase domain mutant (K63A), followed by luciferase assay (c) and IFN-α ELISA (d), with Pin1 WT MEFs stably expressing IRAK1 transfected with EV as a control. Expression levels of WT, W34A and K63A Pin1 proteins are shown below graphs in (c) and (d). ND, not detectable.

(e) Overexpression of KD IRAK1 inhibits IRF7 activity in Pin1 WT, but does not affect basal IRF7 activity in Pin1 KO MEFs. Pin1 WT and KO MEFs were transiently transfected with Gal4-IRF7, $UAS_{(Gal)}$, MyD88 (20 ng) and various amounts of KD IRAK1 or control vector, as indicated, followed by assaying IRF7 activity using Renilla as a control for normalization.

(f, g) Pin1 KO or IRAK1 mutations that prevent IRAK1 from being a Pin1 substrate abolish IRF7 activation and IFN-α production. Pin1 WT and KO cells stably expressing empty vector (EV), IRAK1 or IRAK1 mutants S110A, S131, S144, S173A, 3A (S131+S144+S173A) or KD were co-transfected with $UAS_{(GAL)}$ and Gal4-IRF7 to assess IRF7 reporter activity (f) or with IRF7 to measure IFN-α production (g). Expression levels of IRAK1 and its various mutants are shown below the graph (t).

(h, i) Pin1 KO or IRAK1 mutations that prevent IRAK1 from being a Pin1 substrate abolish antiviral activity. VSV production in plaque-forming units (PFU) per mL 24 h after infection of monolayer L cells (0.1 PFU/cell) previously treated with supernatants from Pin1 WT and KO cells stably expressing EV, IRAK1 or IRAK1 mutants S110A, S131, S144, S173A, 3A or KD (h), with representative pictures of VSV plaques shown in (i). All samples were measured in triplicates. Vertical bars represent S.D.

Figure 7:
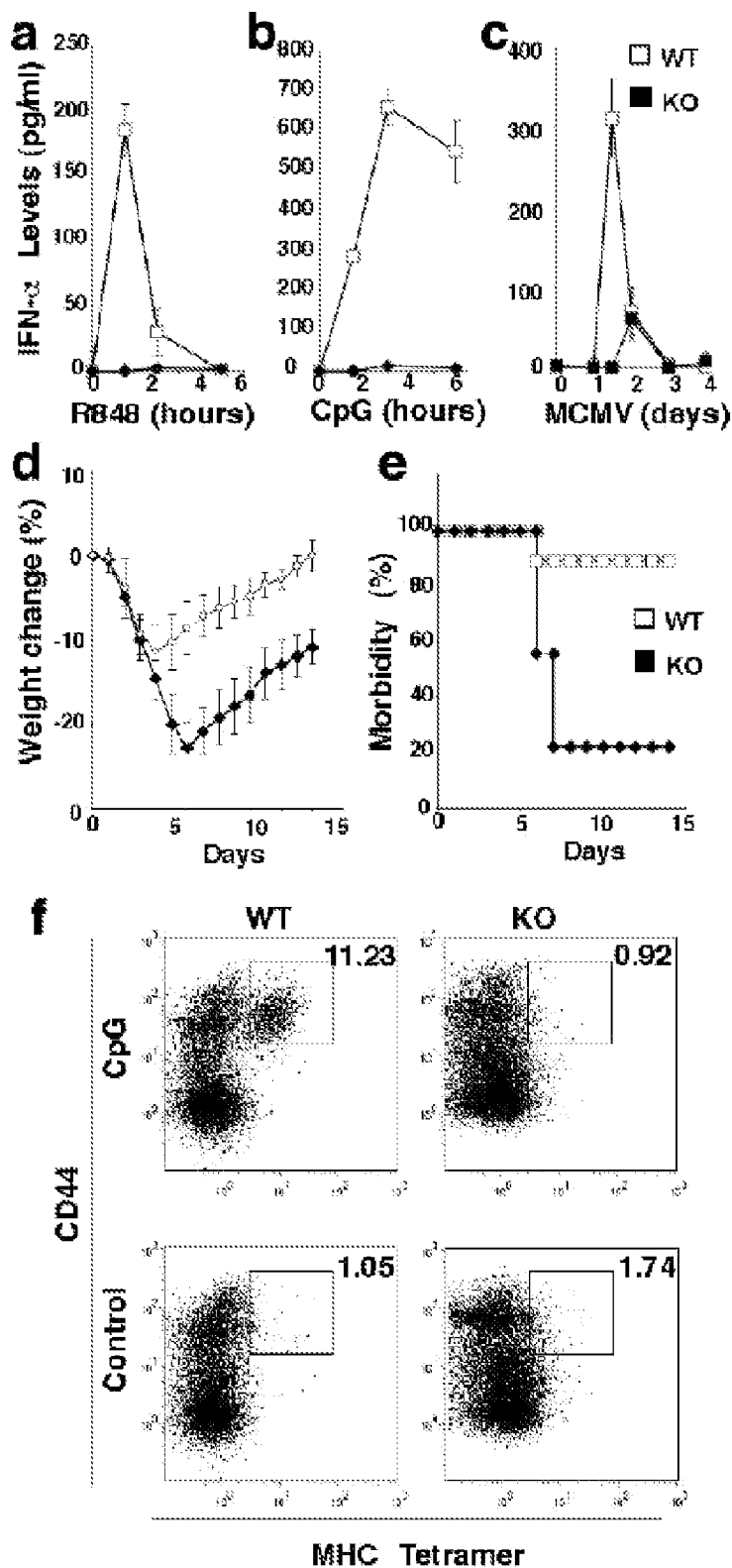

FIG. 7 Pin1 is required for TLR-mediated, type I interferon-dependent innate and adaptive immunity in vivo.

(a-c) Pin1 KO mice completely fail to mount robust IFN-α response upon TLR7/9 activation. Pin1 WT and KO mice were injected with 50 nmol of R-848 (i.v.) (a), 5 μg CpG-A complexed to DOTAP (i.v.) (b), or MCMV $5 \times 10^4$ PFU (i.p.) (c), followed by assaying serum IFN-α levels at different time points. (n=3)

(d, e) Pin1 KO mice are highly vulnerable to viral infection. Pin1 WT and KO mice were injected with $2.5 \times 10^4$ PFU MCMV, followed by monitoring changes in body weights over time (d) or with $10^5$ PFU MCMV, followed by monitoring morbidity daily for 14 days (n=6) (e).

(f) Pin1 KO mice are severely defective in triggering the TLR-mediated, IFN-dependent adaptive immunity. Pin1 WT and KO mice were immunized with ovalbumin, anti-CD40 and CpG-A complexed to DOTAP and six days later, splenocytes were isolated and subjected to FACS analysis using antibodies against CD8a and CD44 antibody and a MHC tetramer. The data shown were gated on CD8a-positive events and are representative of three independent experiments. The numbers indicate the percentage of tetramer-positive cells relative to the total number of $CD8a^+$ T cells.

Figure 8:
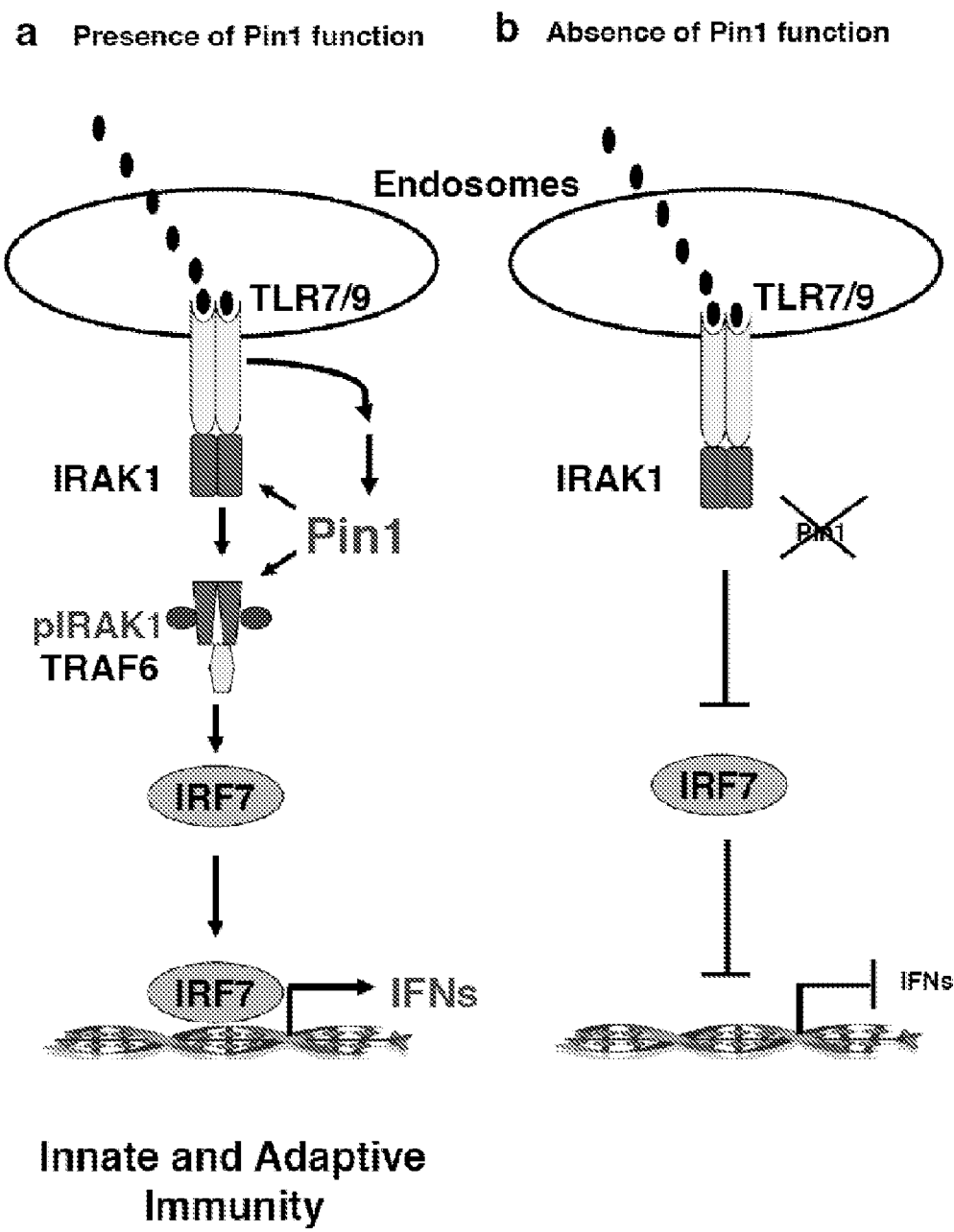

FIG. 8 Essential Role for Pin1 in TLR-IRAK1-IRF-IFN signaling events in innate and adaptive immunity.

(a) Upon activation of TLRs, especially TLR7/9, Pin1 activity is upregulated and IRAK1 is autophosphorylated in the UD, which allows Pin1 to bind to and isomerize phosphorylated IRAK. Such Pin1-catalyzed conformational change facilitates the dissociation of IRAK1 from the receptor complex and recruitment of TRAF6, which combines with IRAK1 to activate IRF7 by promoting nuclear translocation for the induction of type I interferon to mediate innate and adaptive immunity.

(b) Although Pin1 KO neither affects the recruitment of IRAK1 to the TLR complex, nor the activation of other TLR activated kinases such as IRAK4 and MAP kinases, it specifically prevents IRAK1 activation and release from the receptor complex so that TRAF6 is not recruited and IRF7 activated, leading to loss of type I interferon production and its mediated innate and adaptive immunity.

Figure 9A:
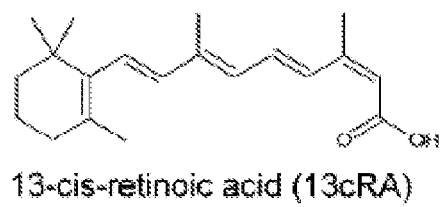
Figure 9A:

FIG. 9A is a schematic of the chemical structure of 13-cis-retinoic acid and all-trans retinoic acid.

Figure 9B:
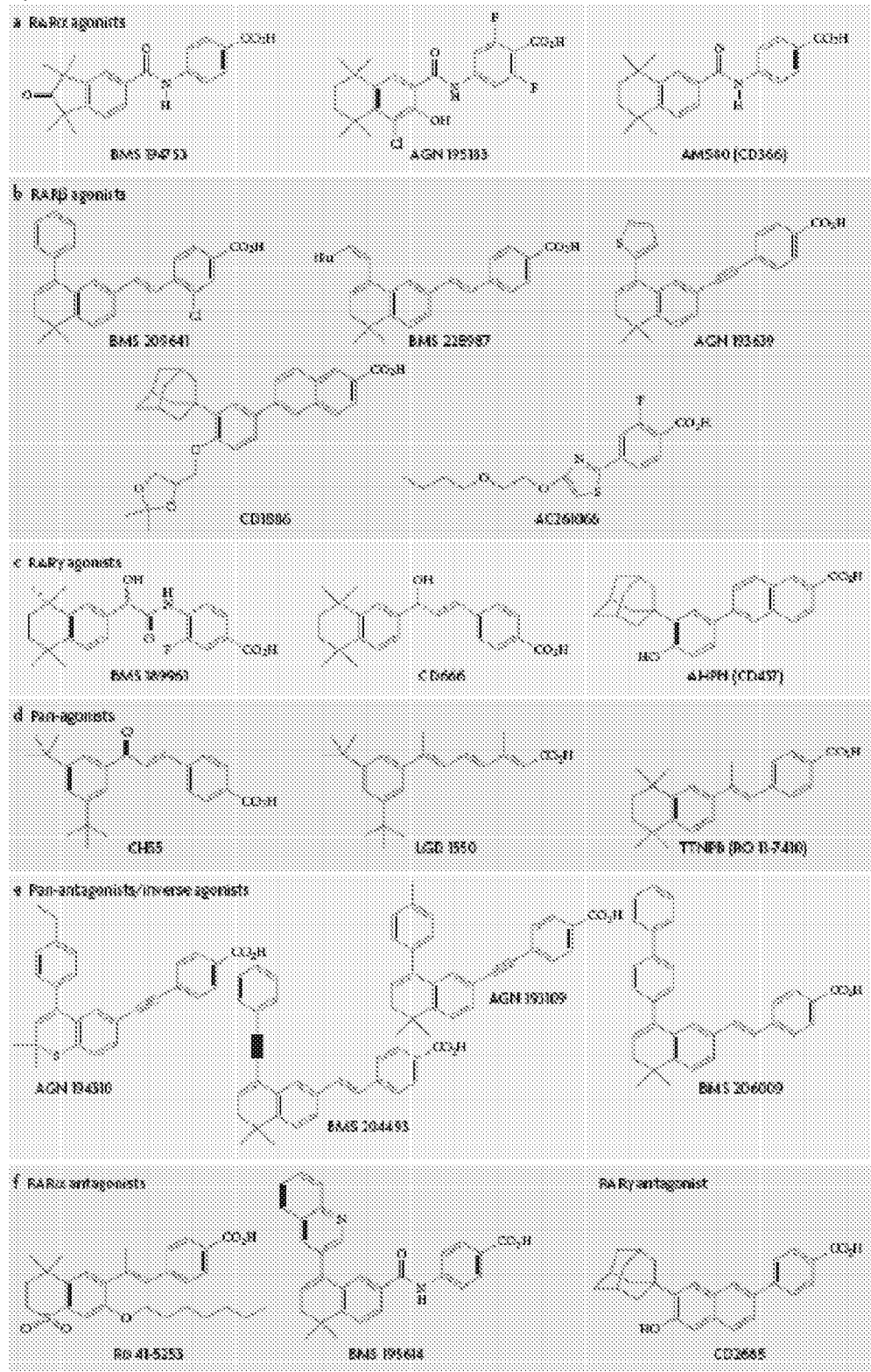

FIG. 9B is a schematic showing additional retinoic acid compounds.

Figure 9C:
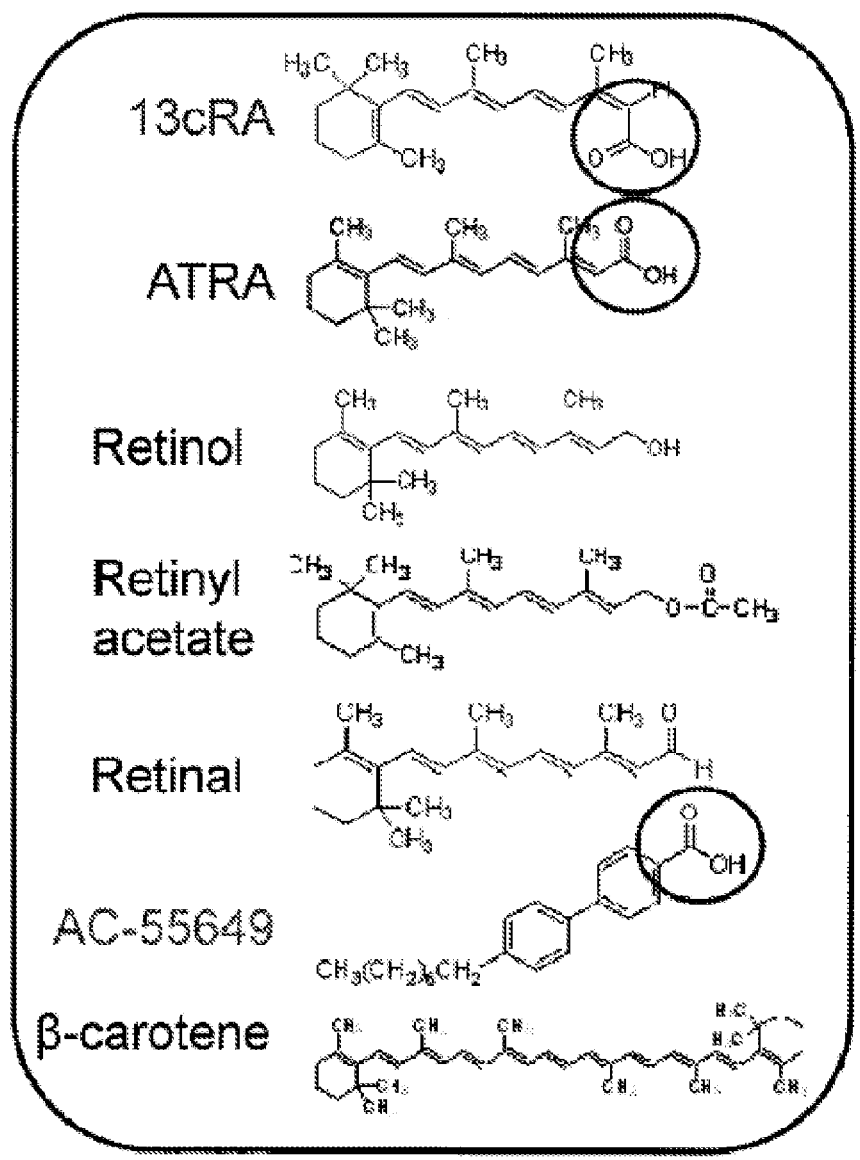

FIG. 9C is a series of schematics showing the indicated retinoic acid compounds and β-carotene.

Figure 10:
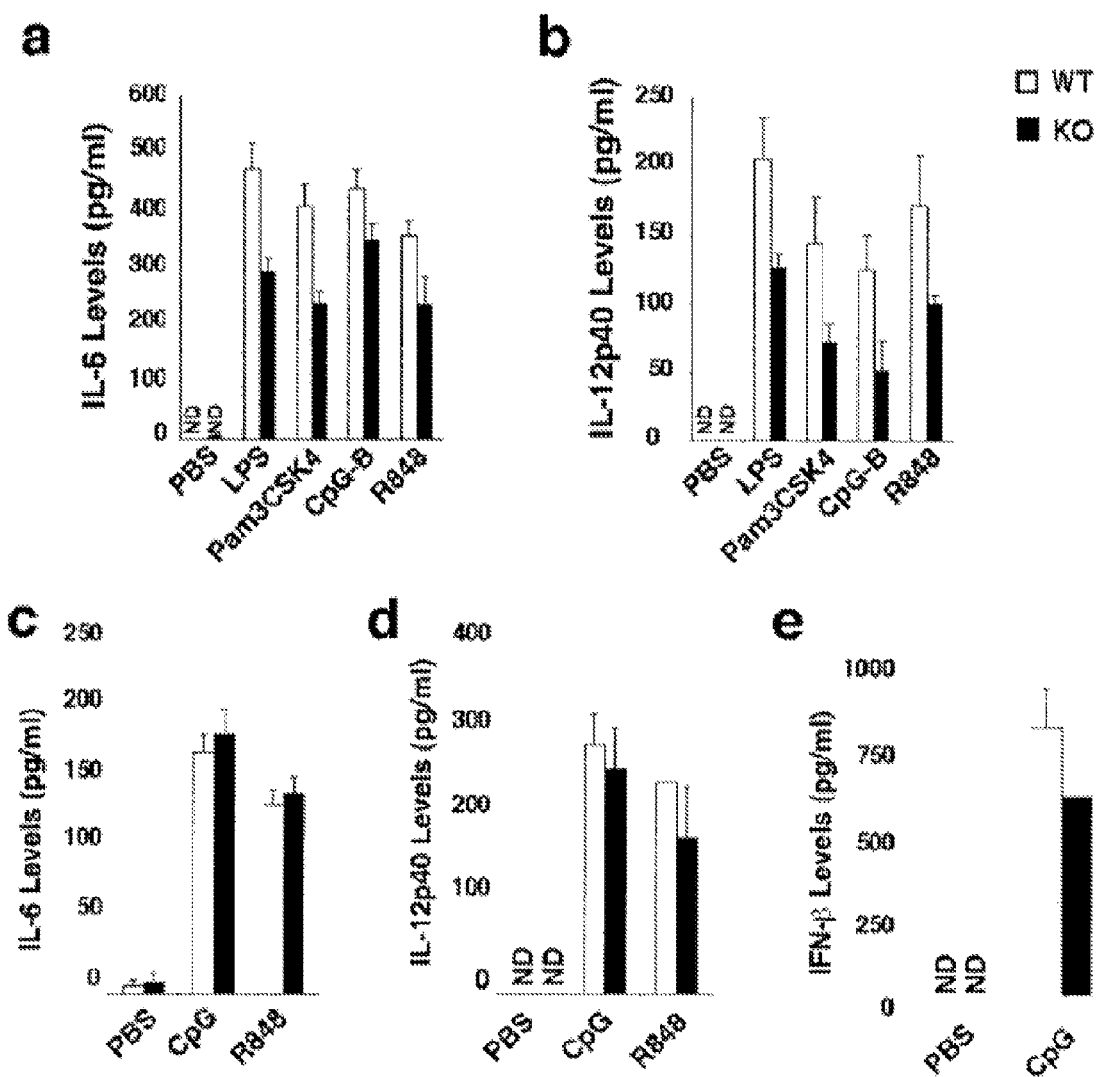

FIG. 10 shows Pin1 deficiency moderately inhibits inflammatory cytokine production in macrophages but does not affect proinflammatory cytokines in the pDCs and IFN-β in mDCs.

(a, b) Bone marrow derived macrophages were stimulated with various THL ligands over night. IL-6 (a) and IL-12p40 (b) levels in supernatants was measured by ELISA. Splenic pDCs were isolated by negative selection sing MACS beads according to the manufacturer's guidelines and stimulated with CpG or R848 for 24 h.

(c, d) IL-6 and IL-12p40 concentrations were measured in supernatants by ELISA. Purity of isolated pDCs was >95% as assessed by flow cytometry using antibodies against PDCA1, B220 and CD11c.

(e) Bone marrow derived mDC were stimulated with CpG for 24 h and IFN-β levels were measured in the supernatants by ELISA. Results represent mean values of three independent experiments.

Figure 11:
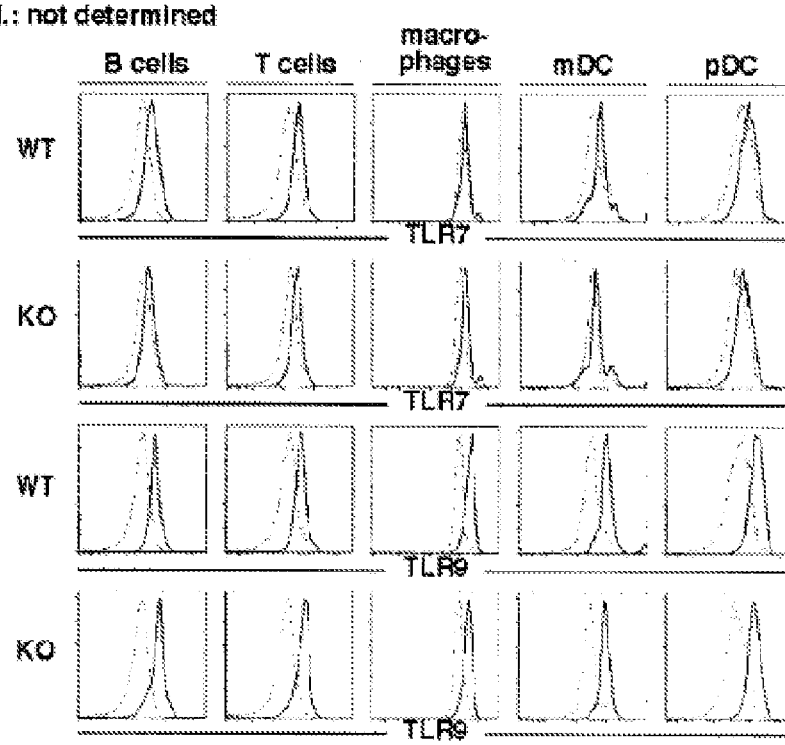
Figure 11:
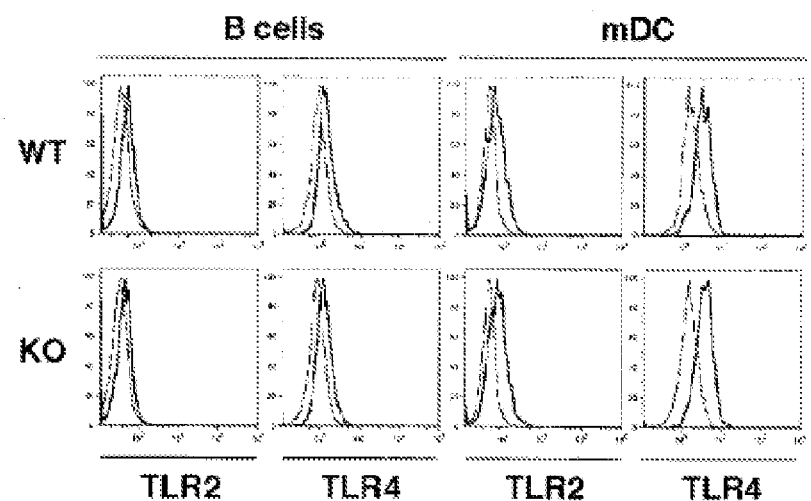

FIG. 11 shows Pin1 KO has no effects on overall population of immune cells and their TLR expression.

(a) CD4+ T cells, CD8+ T cells, B cells, mDCs and pDCs isolated form spleens and lymph nodes of Pin1 WT and KO mice were determined by FACS analysis using various cell markers.

(b) TLR7 and TLR9 expression in T cells, B cells, macrophages, mDCs and pDCs isolated from Pin1 WT and KO mice were analyzed using FACS analysis.

(c) TLR2 and TLR4 expression in Pin1 WT and KO splenic B cells and mDCs isolated from Pin1 WT and KO mice were analyzed using FACS analysis.

Figure 12:
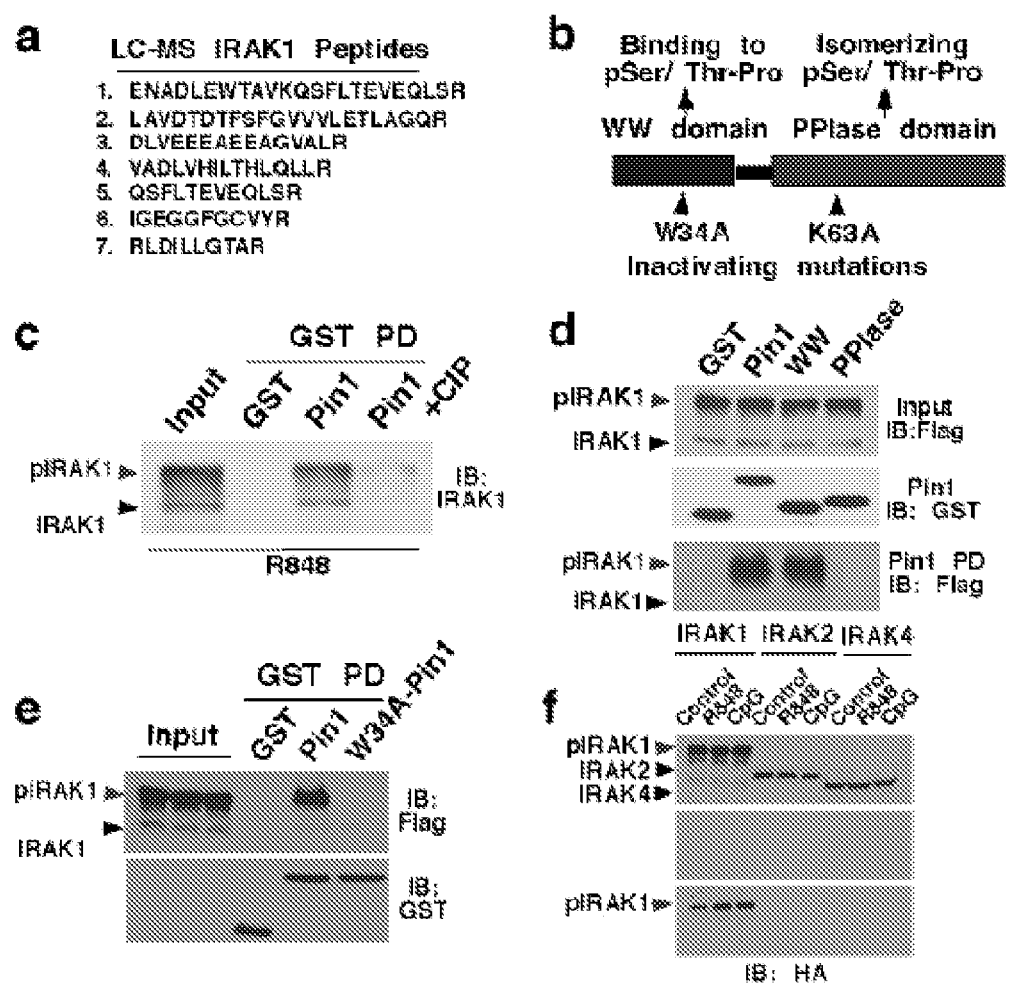

FIG. 12 shows that the Pin1-IRAK1 interaction is mediated by IRAK1 phosphorylation and Pin1 WW domain.

(a) Peptides matching IRAK1 form LC-MS identification of TLR7 dependent Pin1 binding partners.

(b) Schematic diagram of Pin1 illustrating the modular domains (WW domain and PPIase domain), their respective function and inactivating point mutations in key functional residues.

(c) The Pin1-IRAK1 interaction is sensitive to phosphatase treatment. Raw264.7 cells were stimulated with R848 and extracts were untreated or treated with CIP phosphatase, followed by GST-Pin1 pulldown (PD).

(d) The WW domain of IRAK1 mediates the Pin1-IRAK1 interaction. FLAG-IRAK1 was expressed in IRAK1-null HEK293T cells, followed by GST pulldown using GST, GST-Pin1, GST-WW or GST-PPIase domain.

(e) The Pin-IRAK1 interaction is blocked by inactivating the Pin1 WW domain function using the W34A mutation. FLAG-IRAK1 was expressed in IRAK1-null HEK293T cells, followed by GST pulldown using GST, GST-Pin1 or W34A-Pin1 protein.

(f) Pin1 binds specifically to IRAK1 but not IRAK2 or IRAK4. HA tagged human IRAK1, IRAK2, and IRAk4 were transfected into RAW 264.5 cells followed by treatment with PBS, R848 (TLR7) or CpG ODN (TLR9). Interaction with Pin1 was determined by GST-Pin1 PD was immunoblotting with anti-HA antibodies.

Figure 13:
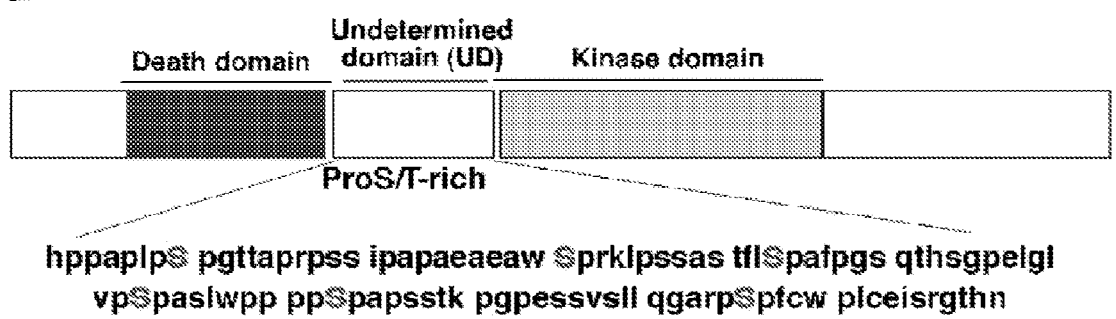
Figure 13:
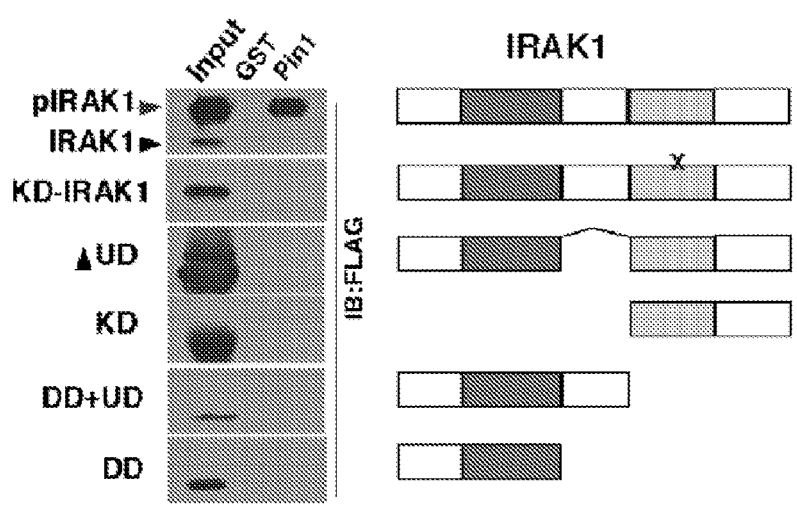

FIG. 13 shows that the Pin1-IRAK1 interaction is mediated by ProS/T-rich undetermined domain (UD).

(a) Schematic diagram of IRAK1 illustrating the functional domains including death domain, ProS/T-rich UD, and the kinase domain. Amino acid sequence of the ProS/T-rich UD highlighting the potential Pin1 binding sites (dark gray).

(b) Mapping IRAK1 domains for binding to Pin1 shows that deletion of the hUD or kinase-dead K239S mutation abolished Pin1 binding. FLAG-IRAK1 deletion mutants were expressed in IRAK1 deficient 293T cells, followed by GST-Pin1 pulldown.

Figure 14:
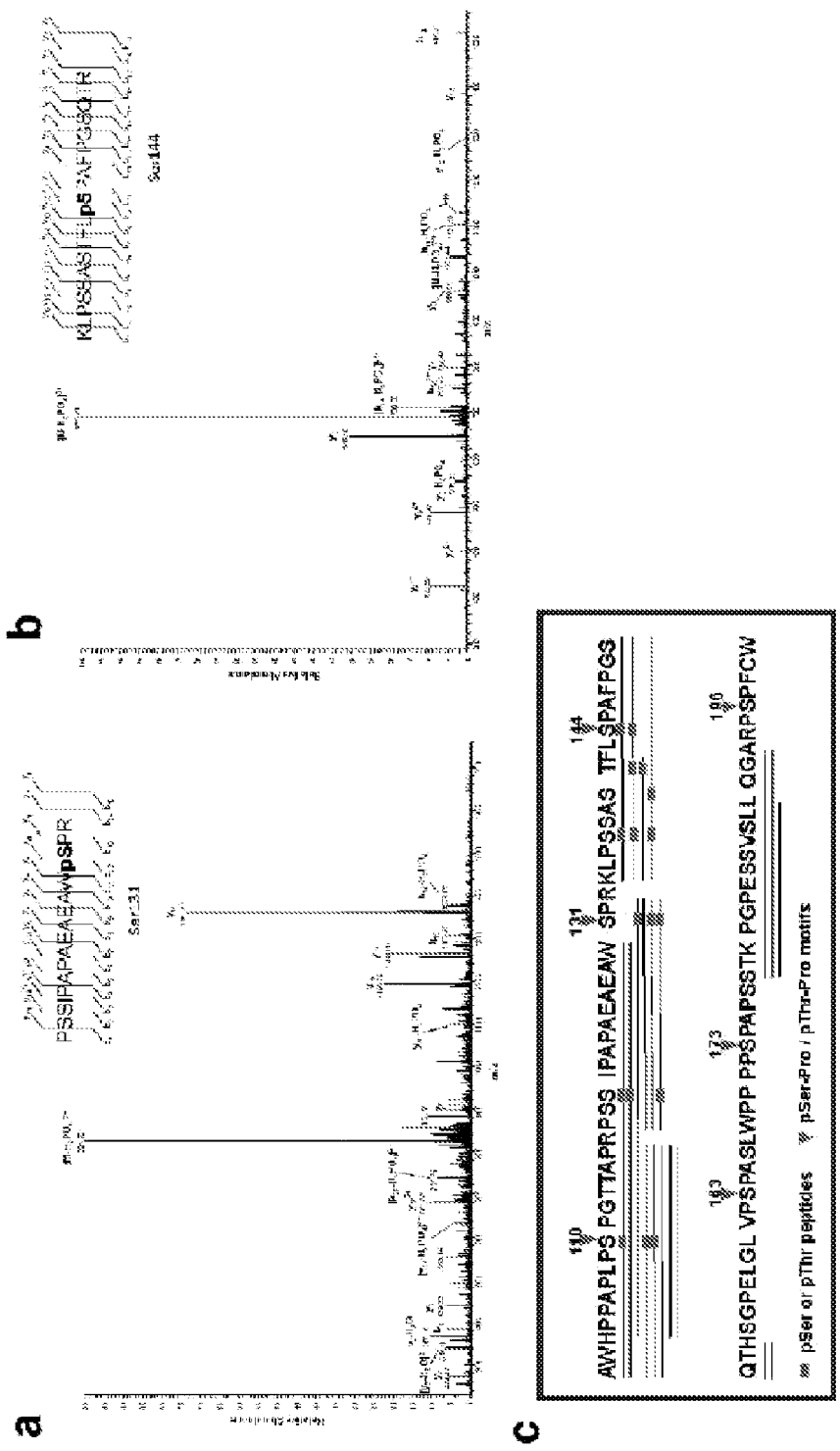

FIG. 14 shows the identification of IRAK1 phosphorylation sites by LC-MS.

(a,b) LC-MS chromatograms demonstrating phosphorylation of S131 and S144 in IRAK1. FLAG IRAK1 was purified using anti-FLAG agarose and eluted followed by purification using GST-Pin1. Following separation by SDS-PAGE and CBB staining bands were digested with trypsin and analyzed by LC-MS.

(c) Schematic diagram of the peptides detected by LC-MS from tryptic digests and highlighting potential Pin1 binding sites in the UD of IRAK1. Squares on peptides indicate phospho-serine/threonine residues. Note: no peptides were detected for the region spanning S173.

Figure 15:
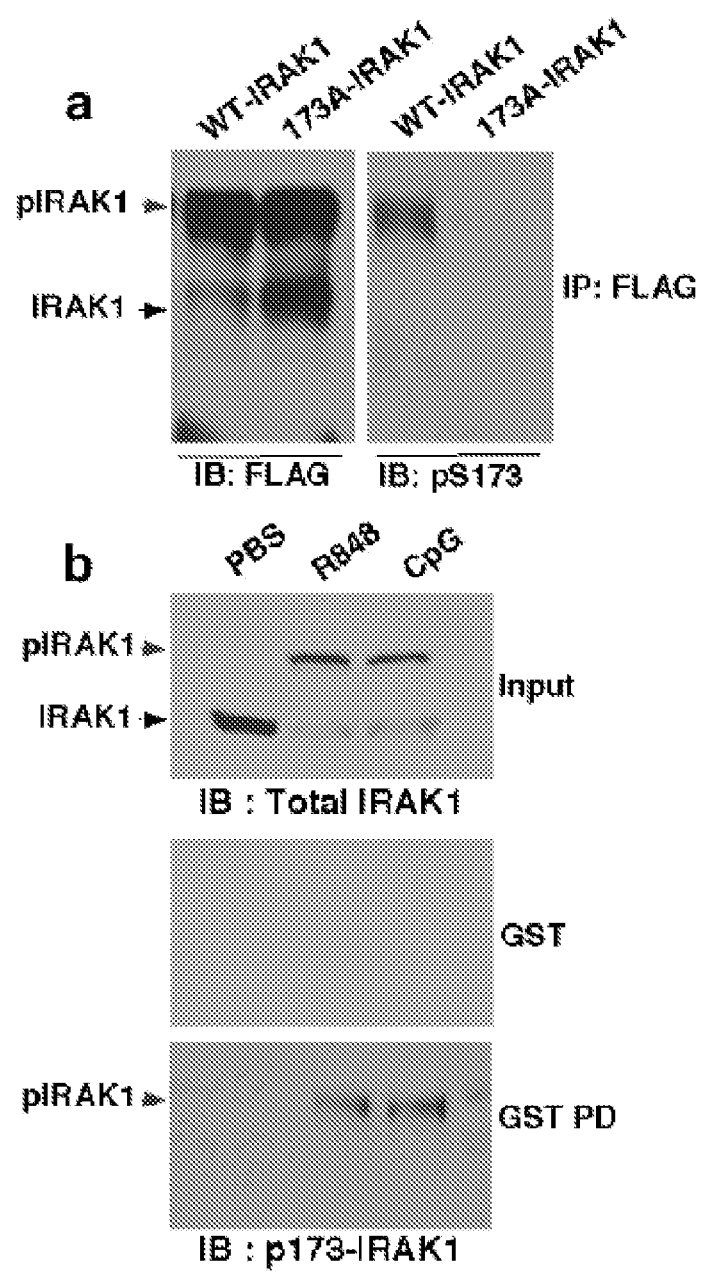

FIG. 15 shows the detection of phosphorylation of endogenous and exogenous IRAK1 on S173.

(a) Anti-pSer173 antibodies specifically recognize the WT IRAK1 but not the S173A mutant. FLAG WT and S173A IRAK1 were highly overexpressed in IRAK null 293 cells and purified using FLAG beads. Immunoblotting was performed using anti-FLAG or anti-phospho-Ser173 antibodies.

(b) THP1 cells were stimulated with PBS, R848 (TLR7) and GST-Pin1 PD was performed followed by immunoblotting with anti-pSer173 IRAK1 antibody. Total cell lysates were immunoblotted with total IRAK1 antibodies.

Figure 16:
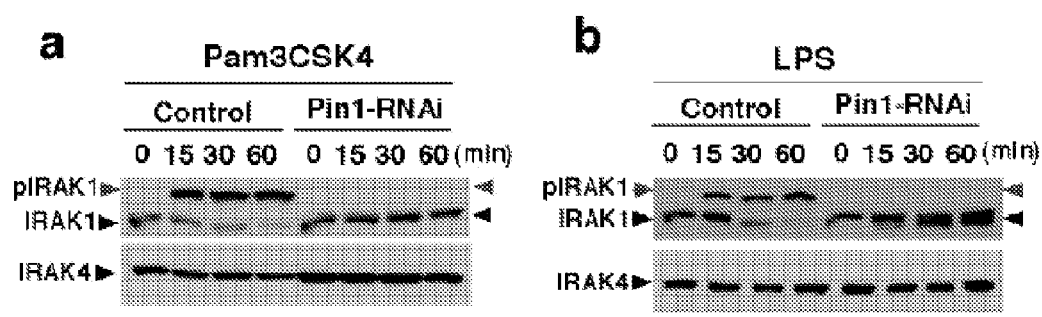

FIG. 16 shows Pin1 knockdown completely blocks IRAK1 activation in response to activation in response to activation of TRL2 and TLR4 in human monocytes.

(a) Human THP1 monocytes were stably infected with control shRNA or shRNA targeting Pin1 and then stimulated with Pam3CSK4 (TLR2 ligand) for the indicated times, followed by analyzing the characteristic IRAK1 mobility shift associated with IRAK1 full activation by immunoblotting with IRAK1 antibody. IRAK4 levels were used as a loading control.

(b) Human THP1 monocytes were stably infected with control shRNA or shRNA targeting Pin1 and then stimulated with LPS (TLR4 ligand) for the indicated times, followed by analyzing the characteristic IRAK1 mobility shift associated with IRAK1 full activation by immunoblotting with IRAK1 antibody. IRAK4 levels were used as a loading control.

Figure 17:
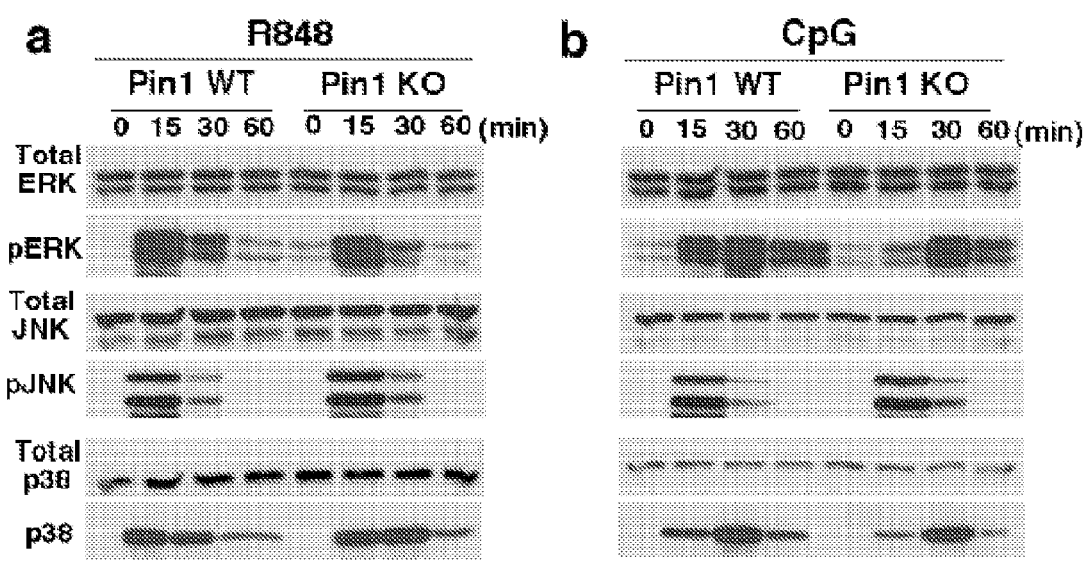

FIG. 17 shows Pin1 knockout does not affect activation of MAPKs in response to activation of TLR7/9 in pDCs.

(a) Following stimulation with R848 for the indicated times, activation of ERKs, JNKs and p38 MAPK in Pin1+/+ and Pin1−/− Flt3 ligand derived pDCs was determined by immunoblotting with phospho-specific antibodies, with total ERKs, JNK and p38 MAPL antibodies as loading controls.

(b) Following stimulation with CpG for the indicated times, activation of ERKs, JNKs and p38 MAPK in Pin1+/+ and Pin1−/− Flt3 ligand derived pDCs was determined by immunoblotting with phospho-specific antibodies, with total ERKs, JNK and p38 MAPL antibodies as loading controls.

Figure 18:
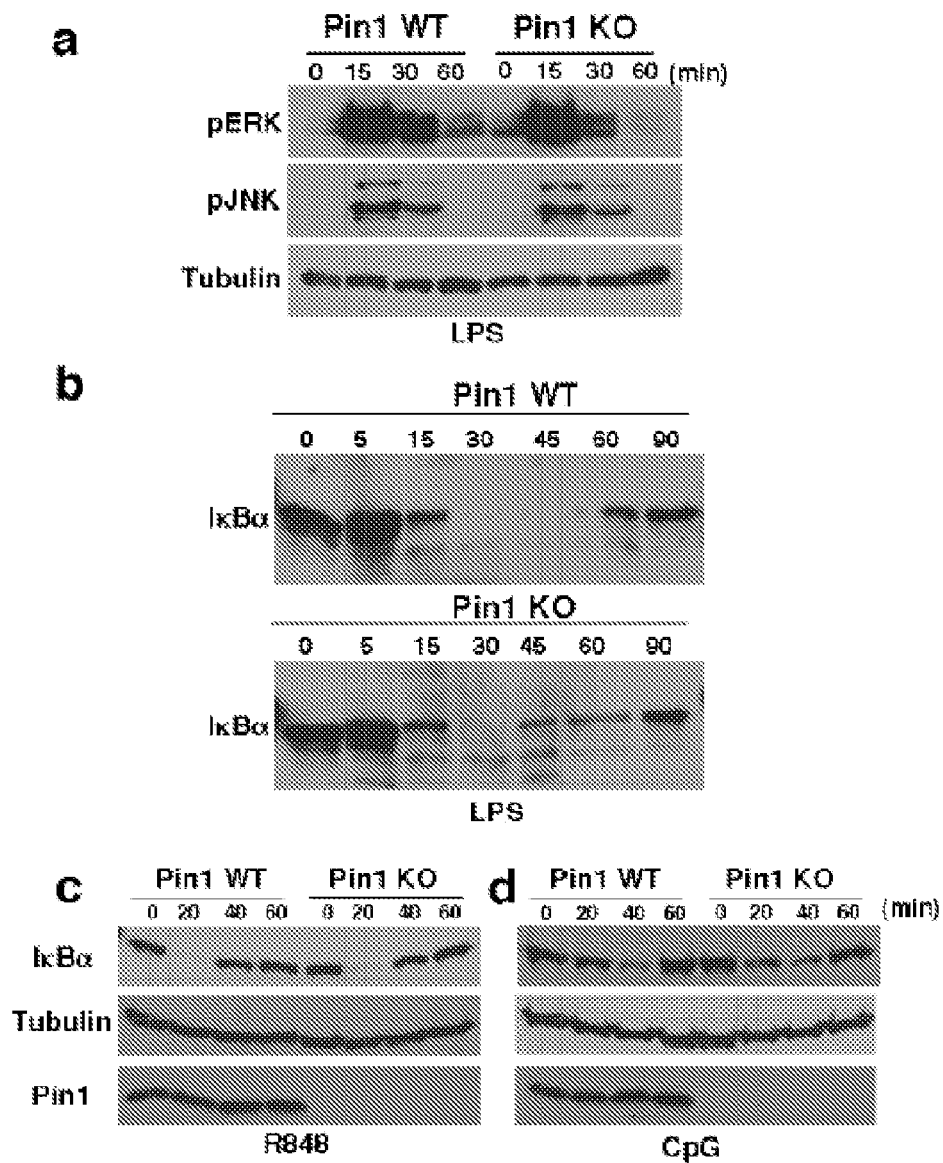

FIG. 18 shows that genetic deletion of Pin1 does not affect activation of NF-κB or MAPK in TLR4 stimulating macrophage or activation of NF-κB in TLR7 or TLR9 stimulated pDC.

(a, b) Bone marrow derived macrophages form Pin1 WT and Pin1 KO mice were stimulated with LPS for the indicated times. The levels of pERK or pJNK (a) or IκBα (b) were determined by immunoblotting with phospho-specific MAPK antibodies or anti-IκBα antibodies, with tubulin levels being used as a control and Pin1 levels were confirmed by immunoblotting with anti-Pin1 antibodies.

(c, d) Bone marrow derived Flt3-pDC from Pin1 WT and Pin1 KO mice were stimulated with R848 or CpG-ODN for the indicated times, followed by immunoblotting with anti-IκBα antibodies.

Figure 19:
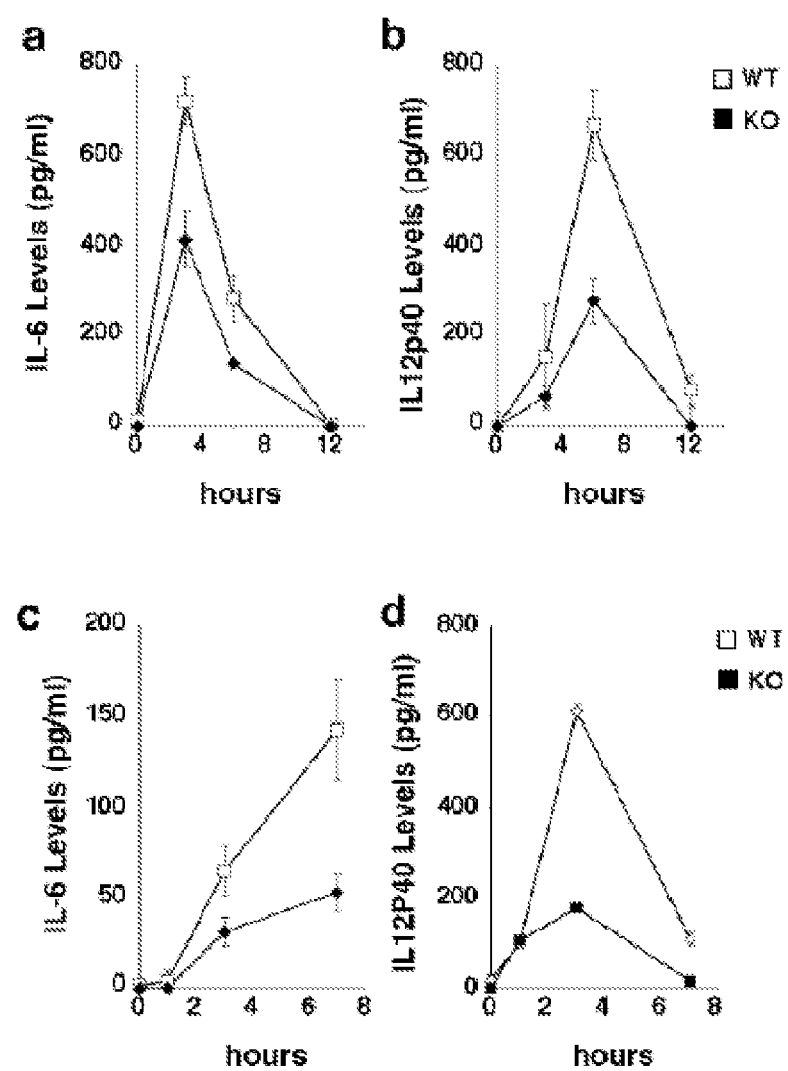

FIG. 19 shows that Pin1 deficiency inhibits TLR4 and TLR7 induction of proinflammatory cytokine production in vivo.

(a,b) IL-6 and IL-12p40 serum levels following i.p. injection of Pin1 WT and Pin1 KO mice with LPS were measured by ELISA at indicated times.

(c,d) IL-6 and IL-12p40 serum levels following i.p. injection of Pin1 WT and Pin1 KO mice with R848 were measured by ELISA at indicated times.

Figure 20:
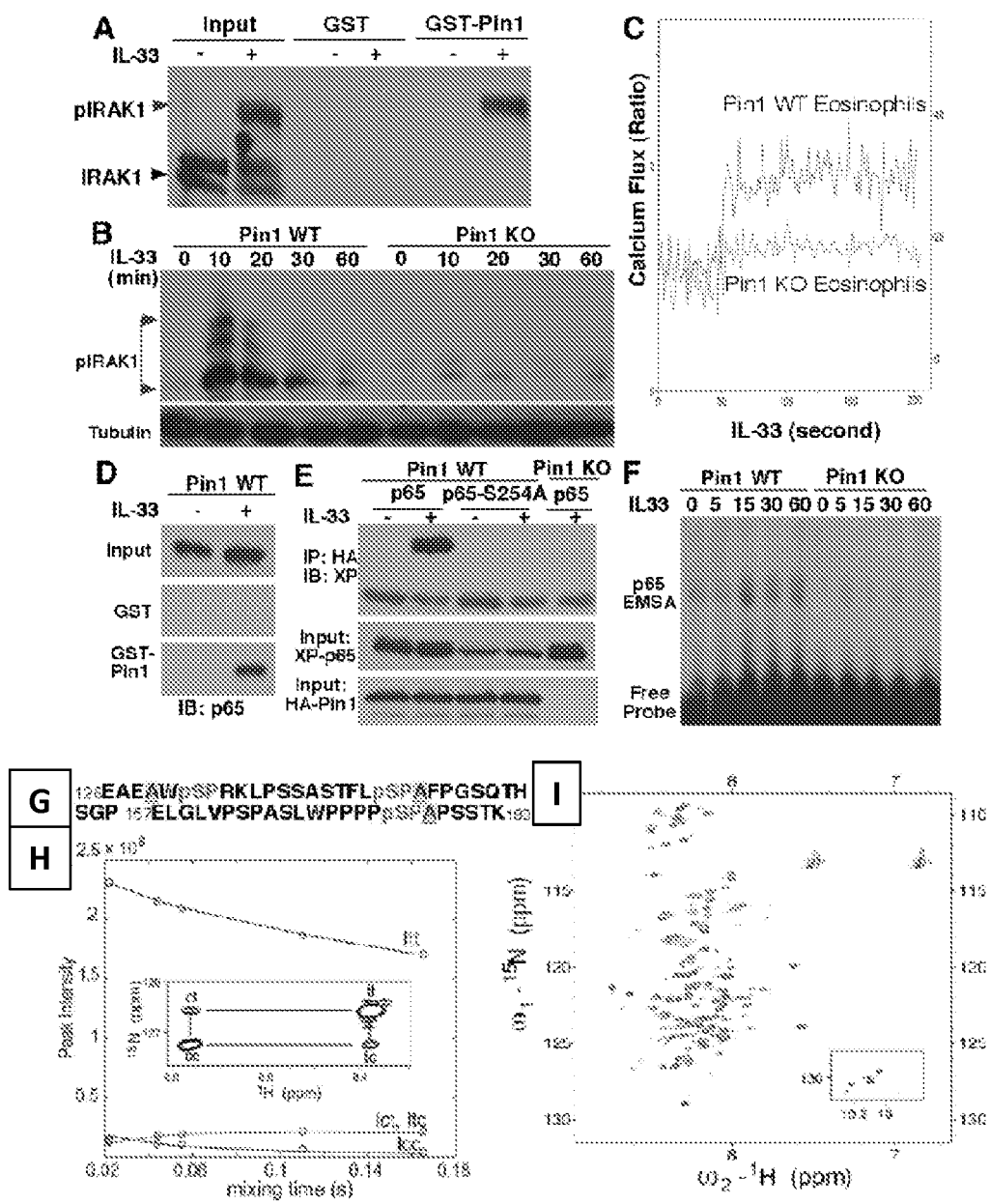

FIG. 20 shows Pin1 bound to IRAK1 and NF-κB upon IL-33 stimulation and Pin1 KO abolished IL-33 induced IRAK1 activation, calcium influx and NF-κB activation.

(A) GST-Pin1 pulldown showed Pin1 binding to activated form of IRAK1 in THP monocytes after stimulation with IL-33 (100 mg/ml).

(B) IL-33 activated IRAK1 in Pin1 WT, but not KO MEFs in a time-dependent manner.

(C) IL-33 induced calcium influx in eosinophils derived from Pin1 WT, but not KO bone marrows, as measured by Fura 2-AM.

(D, E) GST-Pin1 pulldown (D) And Co-IP (E) Showed Pin1 binding to p65 NF-κB in Pin1 WT, but not KO MEFs after IL-33 stimulation.

(F) IL-33 activated NF-κB in Pin1 WT, but nor KO MEFs, as shown by p65 gel-shift assay (EMSA).

(G) Preliminary NMR results showing region of IRAK1-UD sequence containing the three pSP sites implicated in Pin1 activation.

(H) NMR measurement (inset, Nzz spectrum of [15N-Ala175] UD157-180 peptide) and data fitting to yield Pin1-catalysis rate at pS173P.

(I) 15N-1HfHSQC spectrum of recombinant 15N-IRAK1-UD (residues 85-212) indicates disorder and the presence of various cis isomers (minor populations).

Figure 21:
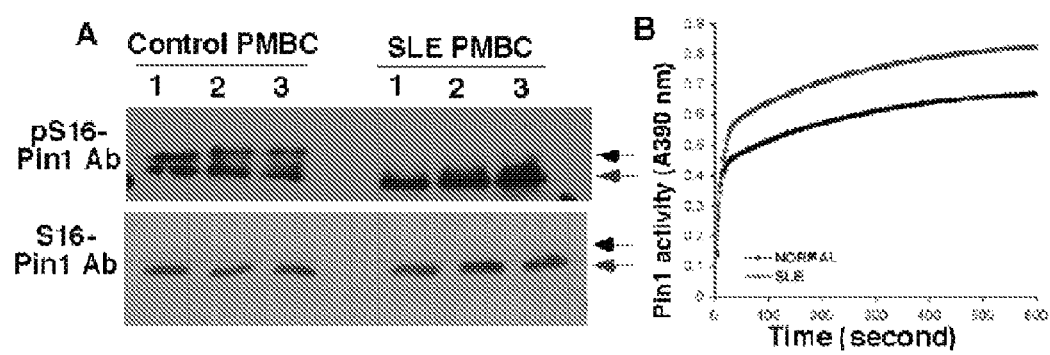

FIG. 21 shows Pin1 might be hyperphosphorylated and activated in SLE.

(A) PBMCs were isolated from normal and SLE patients and immunoblotted with Pin1 antibodies specific to pS16 (top) or S16 (bottom) of the WW domain.

(B) PBMCs were isolated from normal and SLE patients and were subjected to Pin1 PPIase assays.

Figure 22:
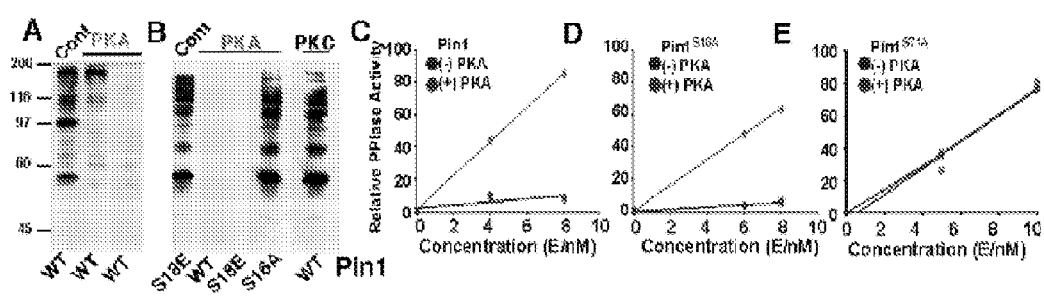

FIG. 22 shows phosphorylation of Pin1 by PKA inhibits its function.

(A, B) S16 phosphorylation of Pin1 in the WW domain abolishes its substrate binding activity.

(C-E) S71 phosphorylation of Pin1 on PPIase domain abolishes its catalytic activity.

Figure 23:
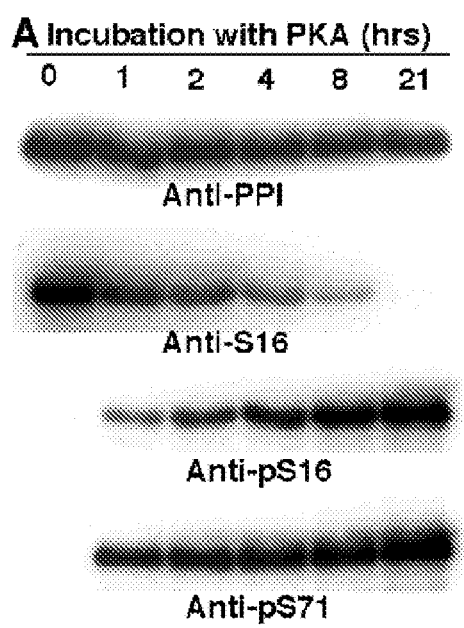
Figure 23:
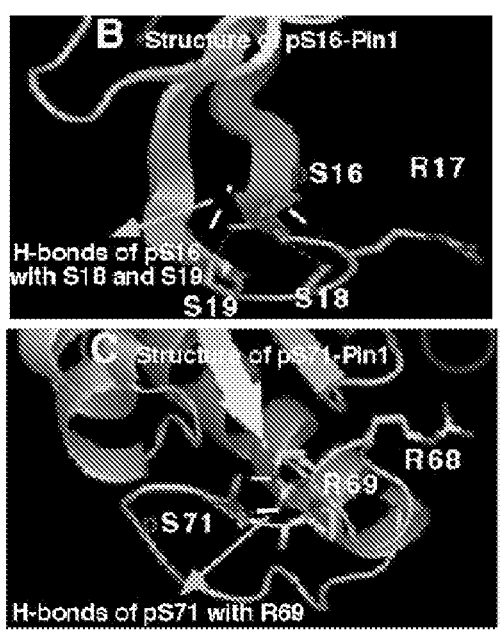

FIG. 23 shows phosphorylation of Pin1 by PKA on S16 and S71 prevents Pin1 from binding to and isomerizing its substrates.

(A) Phosphorylation of Pin1 by PKA on S16 and S71, as detected by our antibodies that recognized Ser16-Pin1, pS16-Pin1, or pS71-Pin1.

(B) S16 phosphorylation formed H-bonds with S18 & S19, preventing substrates from entering the binding site.

(C) S71 phosphorylation formed H-bonds with R69, preventing substrates from entering the catalytic active site.

Figure 24:
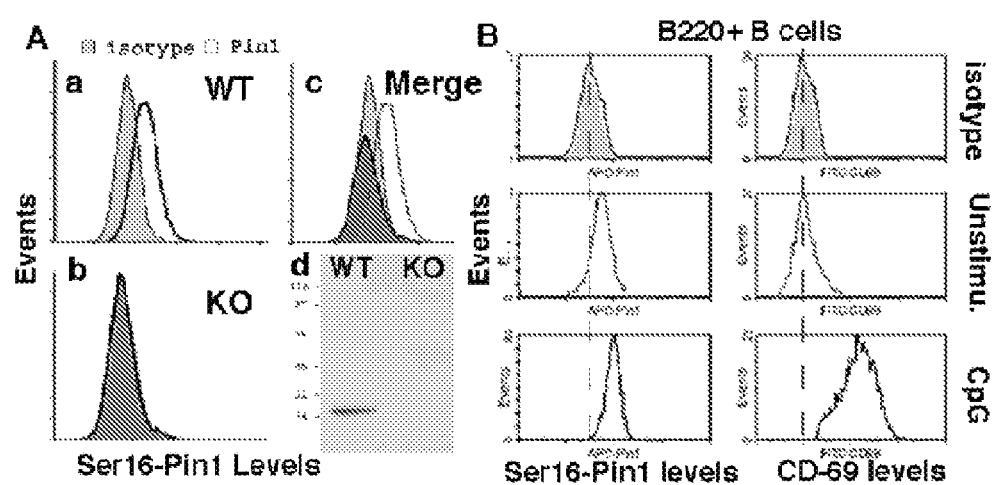

FIG. 24 shows activation of Pin1 in B cells by TLR9.

(A) Detection of Pin1 in Pin1 WT but not Pin1 KO MEFs by icFACS using APC-labeled Pin1 mAb, which recognized a non-phosphorylated active Pin1.

(B) Splenocytes were stimulated for 48 hours with 1 umol CpG, followed by detecting activation of Pin1 and B cells using APC-Pin1 and PE-CD69 in B220 positive cells.

Figure 25:
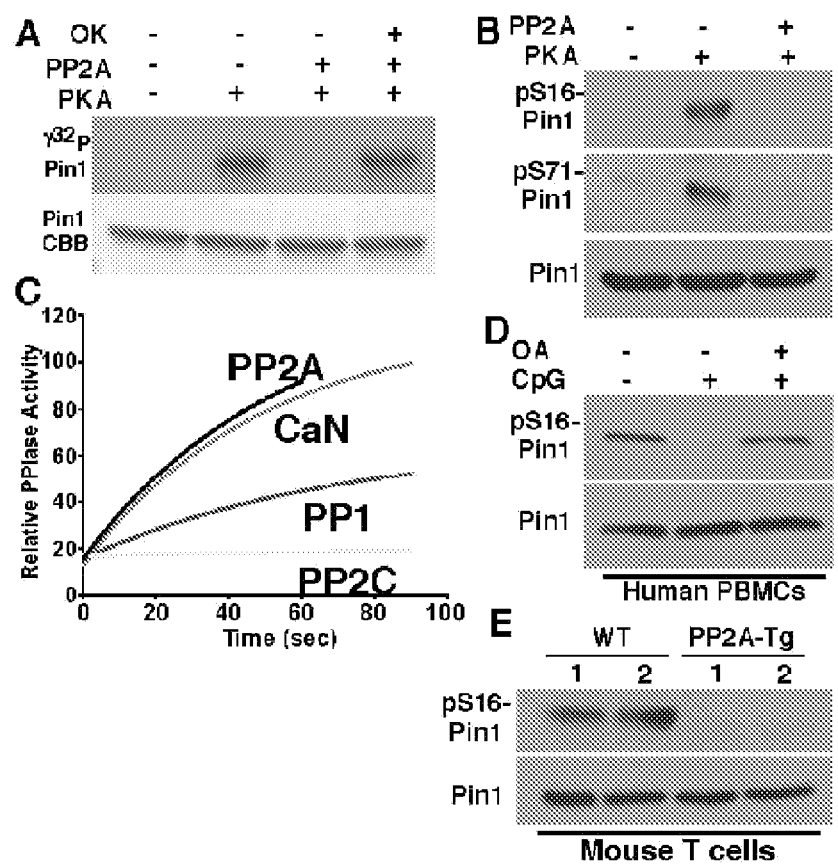

FIG. 25 shows activation of Pin1 by PP2A in vitro and in vivo.

(A) PP2A dephosphorylated Pin1 that was phosphorylated by PKA, as detected by $^{32}P$-labeling.

(B) PP2A dephosphorylated Pin1 that was phosphorylated by PKA, as detected by phospho-specific antibodies.

(C) PP2A fully restored the PPIase activity of Pin1 that was inhibited by PKA phosphorylation.

(D) Pin1 became dephosphorylated in human PBMCs after TLR9 stimulation with CpG, which was reversed by a pretreatment with 5 nM PP2A inhibitor okadaic acid (OA).

(E) Pin1 became dephosphorylated in T cells isolated from PP2A transgenic mice, but not wild-type controls.

Figure 26:
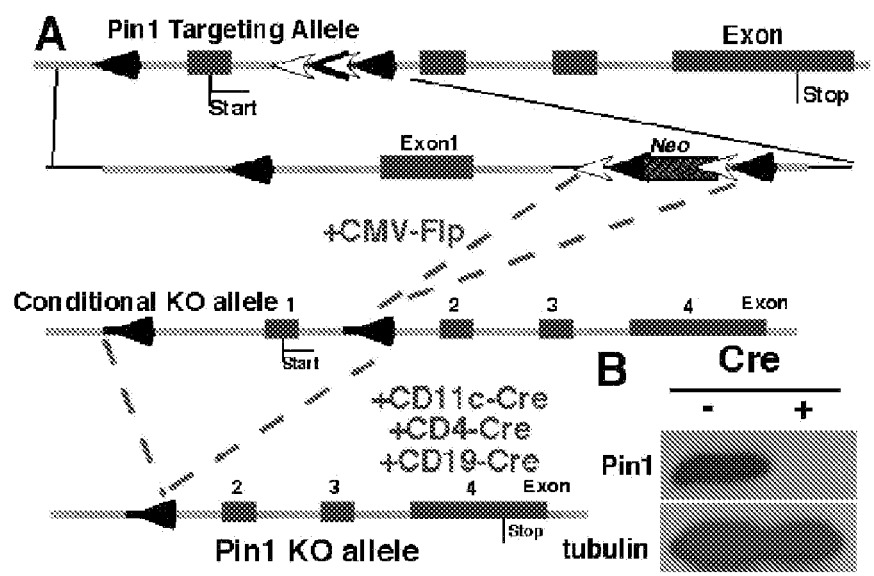

FIG. 26 shows generation of Pin1 conditional knockout in immune cells.

(A) Pin1 CO targeting mice were crossed with CMV-Flp mice of delete the Neo cassette and produce Pin1 Co allele (Pin1fl). Pin1fl/fl mice will be crossed with various lupus prone mice and then with CD11c-Cre, CD4-Cre, or CD19-Cre mice to generate Pin1 CO specifically in DCs, T, or B cells.

(B) Pin1 CO in neurons confirmed by immunoblot.

Figure 27:
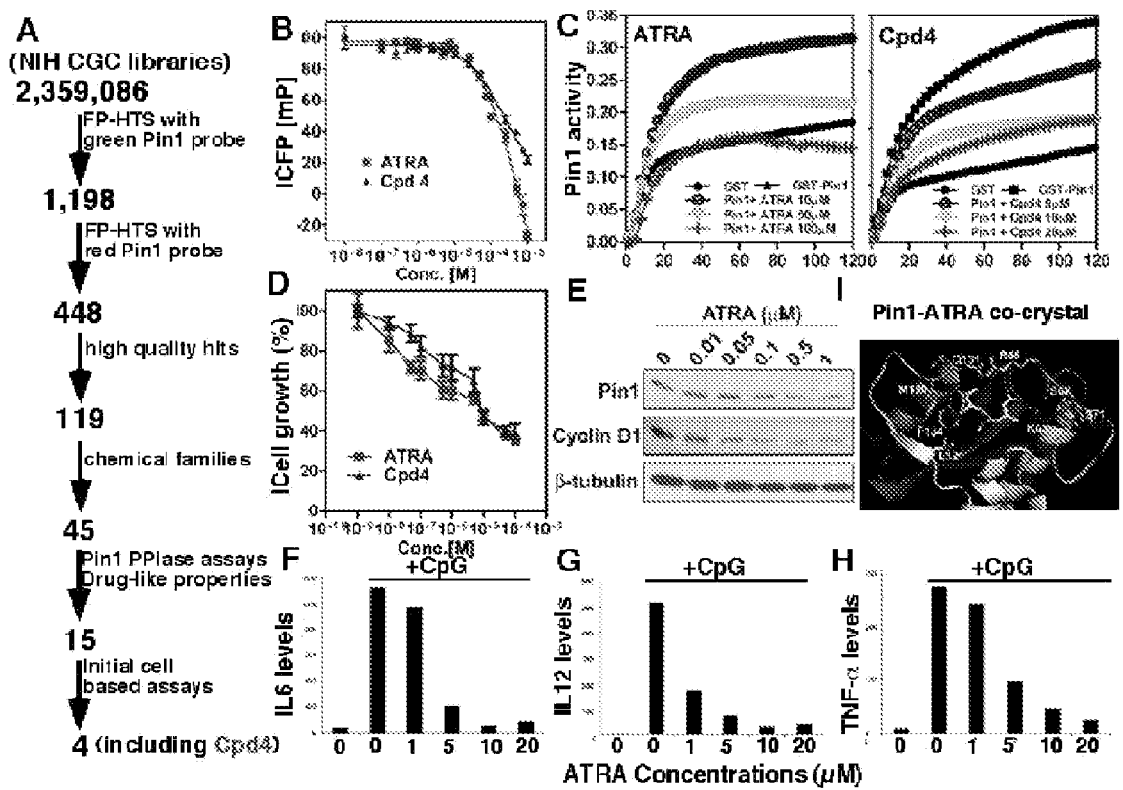

FIG. 27 shows HTS identified novel Pin1 inhibitors that blocked cytokine production induced by TLR9.

(A) Using a FP-based HTS, we identified ATRA and Cpd4 ad new Pin1 inhibitors.

(B) Both ATRA and Cpd4 are confirmed to compete with a peptide inhibitor from binding Pin1.

(C) Both ATRA and Cpd4 are confirmed to compete with a peptide inhibitor to inhibit Pin1 catalytic activity.

(D) Both ATRA and Cpd4 are confirmed to compete with a peptide inhibitor from binding Pin1 to inhibit Pin1-dependent cancer cell growth.

(E) ATRA induced the degradation of Pin1 and its substrate D1 in cancer cells.

(F-H) ATRA inhibited cytokine production (pg/ml) of pDCs in response to TLR activation.

(I) ATRA bound to Pin1 active site, as shown by the co-crystal structure.

Figure 28:
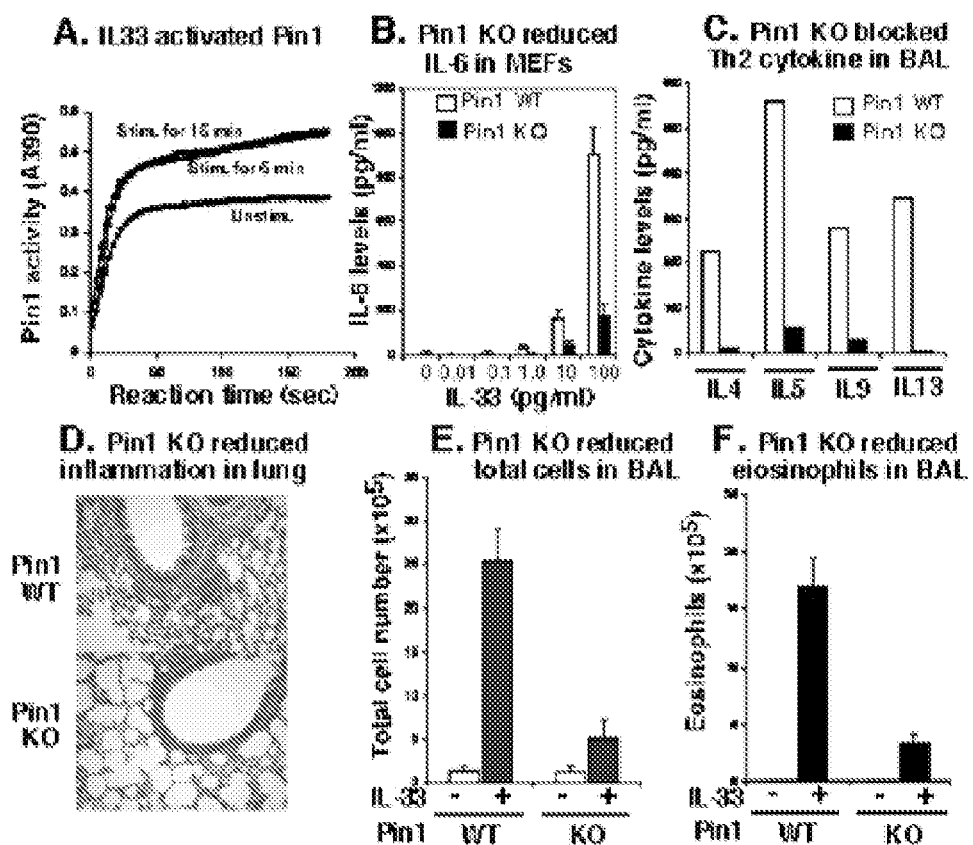

FIG. 28 shows Pin1 is activated by IL-33 and its KO fully suppressed Th2 response and asthma induced by IL-33 in mice and in vitro.

(A) Pin1 isomerase activity in THP monocytes was increased by 5 ng/ml of IL-33.

(B) Pin1 KO completely suppressed IL-6 secretion induced by IL-33 in MEFs.

(C) Pin1 KO fully blocked Th2 response in mouse BAL fluid after intranasal IL-33.

(D-F) Pin1 KO effectively inhibited intranasal IL-33 induced asthma, as shown by histological examination (D), and number of total cells (E) or eosinophils (F). (n=4).

Figure 29:
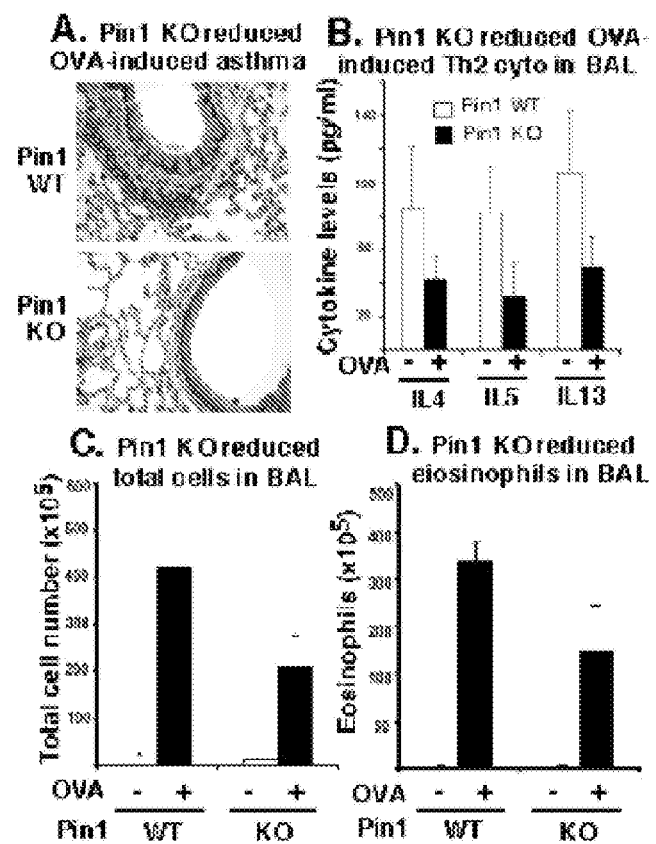

FIG. 29 shows Pin1 KO reduced Th2 response and asthma after OVA allergen challenge in mice.

(A) Pin1 KO reduced OVA-induced asthma in mice, as shown by histological examination.

(B) Pin1 KO reduced OVA-induced asthma in mice, as shown by Th2 response in mouse BAL fluid.

(C) Pin1 KO reduced OVA-induced asthma in mice, as shown by number of total cells.

(D) Pin1 KO reduced OVA-induced asthma in mice, as shown by eosinophils. (n=4).

Figure 30:
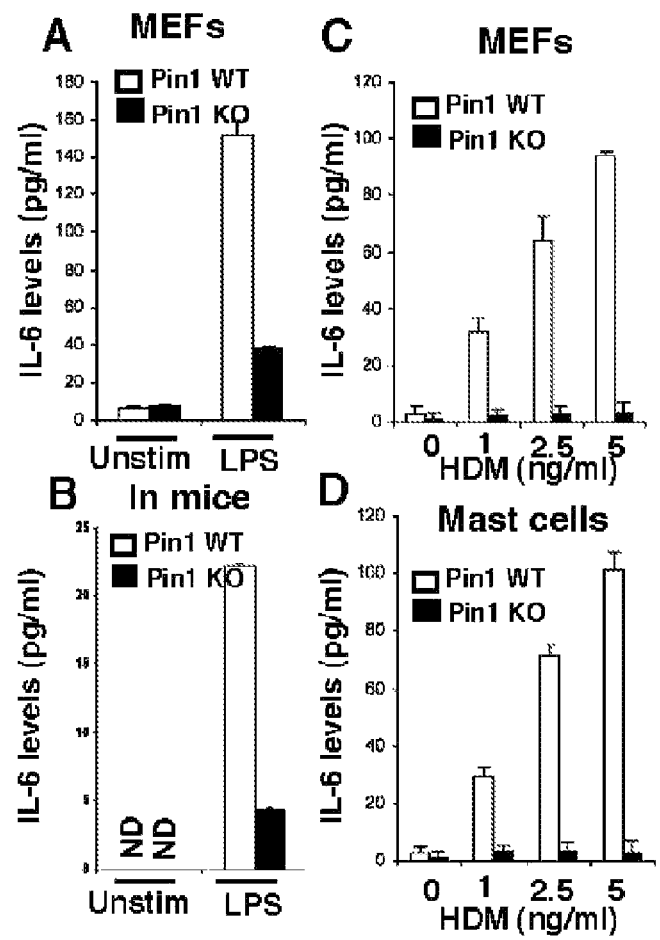

FIG. 30 shows Pin1 KO suppressed proinflammatory cytokine secretion induced by LPS or HDM.

(A) Pin1 KO suppressed IL-6 secretion from MEFs after overnight treatment with 0.1 ug/ml LPS.

(B) Pin1 KO suppressed IL-6 secretion from MEFs after 90 min after injection of mice with 4 mg/ml LPS (B).

(C) Pin1 KO blocked IL-6 secretion induced by various concentrations of HDM in MEFs.

(D) Pin1 KO blocked IL-6 secretion induced by various concentrations of HDM in mast cells.

Figure 31:
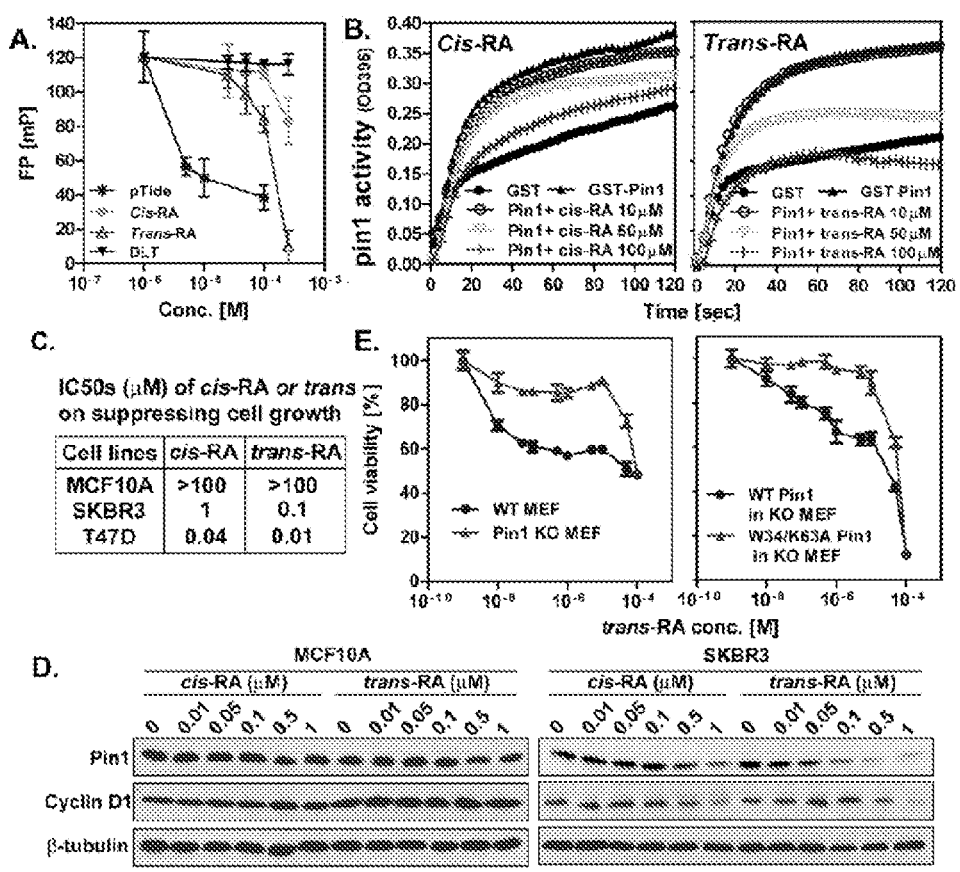

FIG. 31 shows identification of retinoic acids as potential Pin1 inhibitors.

(A) trans-RA bound to Pin1 more efficiently that cis-RA.

(B) Dose-dependant Pin1 inhibition by cis-RA (left) or trans-RA (right).

(C) SKBR3 and T47D cancer cells were more sensitive to RAs than normal MCF-10A cells.

(D) RAs degraded Pin1 in drug-responsive SKBR3 cells (right), but nor in drug-irresponsive MCF 10A (left).

(E) Pin1 KO MEFs were resistant to trans-RA antiproliferative effects (left), but expression of WT Pin1, but not its mutant, restored sensitivity of Pin1 KO MEFs to trans-RA.

Figure 32:

FIG. 32 shows essential moiety of trans-RA for Pin1 inhibition.

(A) Retinoids only with carboxylic acid, but not other groups potently inhibit Pin1.

(B) Crystal structure confirms trans-RA in the Pin1 active site, with the carboxylic acid forming H-bonds with key R68 and K63.

Figure 33:
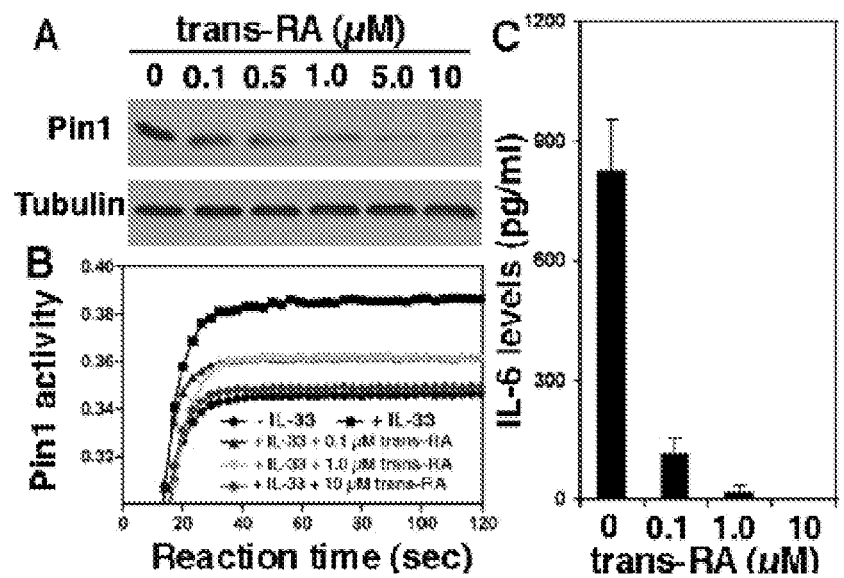

FIG. 33 shows trans-RA inhibited Pin1 activation and IL-6 production in eosinophils induced by IL-33.

(A) BM-derived eosinophils were stimulated without or with 100 ng/ml IL-33 and different levels of trans-RA, followed by Pin1 western.

(B) BM-derived eosinophils were stimulated without or with 100 ng/ml IL-33 and different levels of trans-RA, followed by PPIase assay.

(C) BM-derived eosionophils were stimulated without or with 100 ng/ml IL-33 and different levels of trans-RA, followed by IL-6 ELISA.

Figure 34:
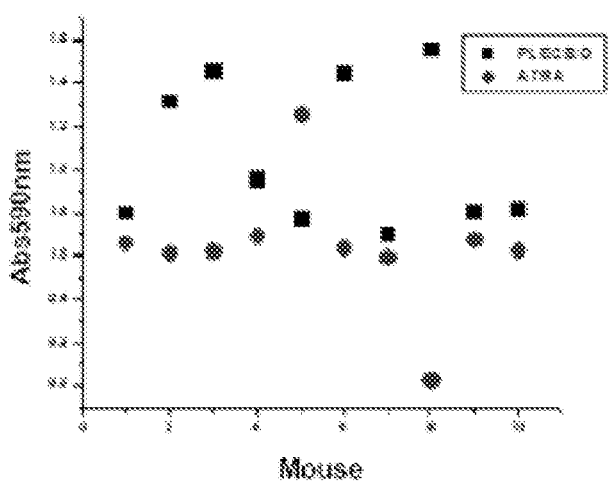

FIG. 34 shows Proteinuria in NZBWF1 mice is significantly reduced by Pin1 inhibitor ATRA. Female lupus-prone NZBWF1 mice were treated with placebo or ATRA for 3.5 months and proteinuria was evaluated by Bio-Rad assay.

Figure 35:
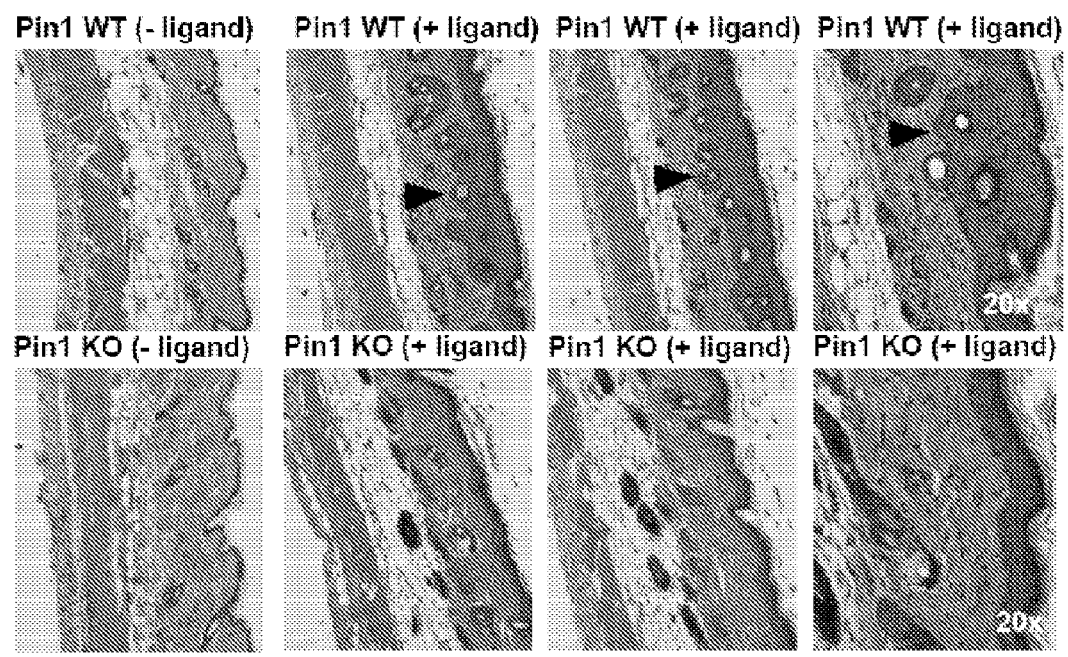

FIG. 35 shows cutaneous inflammation is reduced in Pin1 KO mice. Female Pin1 WT and KO mice were shaved and left untreated or treated dermally with TLR ligands to induce skin inflammation followed by analysis of skin sections by H&E staining. Arrows indicate thickening of the keratinocyte layer (hyperkeratosis).

DETAILED DESCRIPTION OF THE INVENTION

In general, the invention features methods of treating an immune disorder characterized by elevated Pin1 marker levels in a subject by administering a retinoic acid compound. Additionally, the invention features methods of treating an immune disorder (e.g., an immune disorder characterized by elevated Pin1 marker levels), by administering a retinoic acid compound in combination with one or more additional anti-inflammatory, anti-microbial, or anti-viral compounds.

Inhibitors of Pin1 (e.g., retinoic acid compounds) are useful for treating immune disorders (e.g., disorders characterized by increased Pin1 activity or resulting from disregulation of Toll-like receptor signaling or type I interferon-mediated immunity). Furthermore, because Pin1 associated aberrant IRAK1 activation and type I IFN overproduction occurs in various immune diseases, Pin1 inhibition would be expected to behave synergistically with many anti-inflammatory compounds

I. Pin1

Phosphorylation on serine/threonine-proline motifs restrains cis/trans prolyl isomerization, and also creates a binding site for the essential protein Pin1. Pin1 binds and regulates the activity of a defined subset of phosphoproteins, as well as participating in the timing of mitotic progression. Both structural and functional analyses have indicated that Pin1 contains a phosphoserine/threonine-binding module that binds phosphoproteins, and a catalytic activity that specifically isomerizes the phosphorylated phosphoserinelthreonine-proline. Both of these Pin1 activities are essential for Pin1 to carry out its function in vivo.

Pin1 has previously been shown to act on IRF3 to affect IFN-β production upon TLR3 or RIG-I activation. However, recent results have shown that unlike IRF3- or TLR3-deficient mice, IRF7 or IRAK1-deficient mice completely fail to mount a type I IFN antiviral responses due to loss of type I IFN secretion from pDCs. Our results have uncovered an essential role for Pin1 as a novel regulator of IRAK1 activation in TLR signaling and type I IFN-mediated innate and adaptive immunity and revealed that Pin1 inhibitors, which are under active development, may represent a novel therapeutic approach that would allow selective inhibition of the type I IFN response while leaving proinflammatory cytokine production unaffected.

Pin1 is highly conserved and contains a protein-interacting module, called WW domain, and a catalytically active peptidyl-prolyl isomerase (PPIase). Pin1 is structurally and functionally distinct from members of two other well-characterized families of PPIases, the cyclophilins and the FKBPs. PPIases are ubiquitous enzymes that catalyze the typically slow prolyl isomerization of proteins, allowing relaxation of local energetically unfavorable conformational states. Phosphorylation on Ser/Thr residues immediately preceding Pro not only alters the prolyl isomerization rate, but also creates a binding site for the WW domain of Pin1. The WW domain acts a novel phosphoserine-binding module targeting Pin1 to a highly conserved subset of phosphoproteins. Furthermore, Pin1 displays a unique phosphorylation-dependent PPIase that specifically isomerizes phosphorylated Ser/Thr-Pro bonds and regulates the function of phosphoproteins.

II. Measurement of PIN1 Marker Levels

The present invention pertains to the treatment of immune disorders identified as coinciding with elevated Pin1 marker levels with retinoic acid compounds. In some aspects, the invention features the determination of Pin1 marker levels in a subject; where retinoic acid is administered in subjects where Pin1 marker levels are determined to be elevated. In other aspects, the invention can also feature the measurement of Pin1 marker levels subsequent to the administration of retinoic acid compounds in order to evaluate the progress of therapy in treating the immune disorder.

Accordingly, one aspect of the present invention relates to diagnostic assays for measuring levels of Pin1 marker, as well as Pin1 activity, in the context of a biological sample (e.g., blood, urine, biopsies, lymph, saliva, phlegm, and pus) to thereby determine whether an individual is a candidate for treatment with a retinoic acid compound. The invention features both treatment of subjects exhibiting symptoms of an immune disorder and individuals at risk for developing an immune disorder.

Diagnostic Assays

An exemplary method for detecting the presence or absence of Pin1 protein or nucleic acid in a biological sample involves obtaining a biological sample from a test subject and contacting the biological sample with a compound or an agent capable of detecting Pin1 protein or a nucleic acid (e.g., mRNA, genomic DNA) that encodes Pin1 protein such that the presence of Pin1 protein or nucleic acid is detected in the biological sample. A preferred agent for detecting Pin1 mRNA or genomic DNA is a labeled nucleic acid probe capable of hybridizing to Pin1 mRNA or DNA. The nucleic acid probe can be, for example, a Pin1 nucleic acid or a corresponding nucleic acid such as an oligonucleotide of at least 15, 30, 50, 100, 250 or 500 nucleotides in length which is capable of specifically hybridizing under stringent conditions to Pin1 mRNA or genomic DNA. Other suitable probes for use in the diagnostic assays of the invention are described herein.

A preferred agent for detecting Pin1 marker is an antibody capable of binding to Pin1 protein, preferably an antibody with a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

With respect to antibody-based detection techniques, one of skill in the art can raise anti-Pin1 antibodies against an appropriate immunogen, such as isolated and/or recombinant Pin1 or a portion or fragment thereof (including synthetic molecules, such as synthetic peptides) using no more than routine experimentation. Synthetic peptides can be designed and used to immunize animals, such as rabbits and mice, for antibody production. The nucleic and amino acid sequence of Pin1 is known (Hunter et al., WO 97/17986 (1997); Hunter et al., U.S. Pat. Nos. 5,952,467 and 5,972, 697, the teachings of all of which are hereby incorporated by reference in their entirety) and can be used to design nucleic acid constructs for producing proteins for immunization or in nucleic acid detection methods or for the synthesis of peptides for immunization.

Conditions for incubating an antibody with a test sample can vary depending upon the tissue or cellular type. Incubation conditions can depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques," Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of enzyme Immunoassays: Laboratory Techniques in Biochemistry and Molecular Biology," is Elsevier Science Publishers, Amsterdam, The Netherlands (1985).

The detection method of the invention can be used to detect Pin1 mRNA, protein, or genomic DNA in a biological sample in vitro as well as in vivo. For example, in vitro techniques for detection of Pin1 mRNA include northern blot hybridizations and in situ hybridizations. In vitro techniques for detection of Pin1 protein include enzyme linked immunosorbent assays (ELISAs), Western blots, immunoprecipitations, immunofluorescence, or quantitative sequencing reactions. In vitro techniques for detection of Pin1 genomic DNA include Southern hybridizations. The detection of genomic mutations in Pin1 (or other genes that effect Pin1 marker levels) can be used to identify inherited or somatic mutations. Furthermore, in vivo techniques for detection of Pin1 protein include introducing into a subject a labeled anti-Pin1 antibody. For example, the antibody can be labeled with a radioactive marker whose presence and location in a subject can be detected by standard imaging techniques.

In another embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Pin1 marker such that the presence of Pin1 marker is detected in the biological sample, and comparing the presence of Pin1 marker in the control sample with the presence of Pin1 marker in the test sample.

The immunological assay test samples of the present invention may include cells, protein or membrane extracts of cells, blood or biological fluids such as ascites fluid or cerebrospinal fluid. The test sample used in the above-described method is based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized. The invention also encompasses kits for detecting the presence of Pin1 in a biological sample. For example, the kit can comprise a labeled compound or agent capable of detecting Pin1 protein or mRNA in a biological sample; means for determining the amount of Pin1 in the sample; and means for comparing the amount of Pin1 in the sample with a known standard. The compound or agent can be packaged in a suitable container. The kit can further comprise instructions for using the kit to detect Pin1 protein or nucleic acid.

Pin1 marker levels can also be measured in an assay designed to evaluate a panel of target genes, e.g., a microarray or multiplex sequencing reaction. In the embodiments of the invention described herein, well known biochemical methods such as northern blot analysis, RNase protection assays, southern blot analysis, western blot analysis, in situ hybridization, immunocytochemical procedures of tissue sections or cellular spreads, and nucleic acid amplification reactions (e.g., polymerase chain reactions) may be used interchangeably. One of skill in the art would be capable of performing these well-established protocols for the methods of the invention. (See, for example, Ausubel, et al., "Current Protocols in Molecular Biology," John Wiley & Sons, NY, N.Y. (1999)).

Diagnostic assays can be carried out in, e.g., subjects diagnosed or at risk of an immune disorder. Such disorders include, without limitation, acne vulgaris; acute respiratory distress syndrome; Addison's disease; adrenocortical insufficiency; adrenogenital syndrome; allergic conjunctivitis; allergic rhinitis; allergic intraocular inflammatory diseases, ANCA-associated small-vessel vasculitis; angioedema; ankylosing spondylitis; aphthous stomatitis; arthritis, asthma; atherosclerosis; atopic dermatitis; autoimmune disease; autoimmune hemolytic anemia; autoimmune hepatitis; Behcet's disease; Bell's palsy; berylliosis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; epicondylitis; erythema nodosum; exfoliative dermatitis; fibromyalgia; focal glomerulosclerosis; giant cell arteritis; gout; gouty arthritis; graft-versus-host disease; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflammatory bowel or gastrointestinal disorders, inflammatory dermatoses; juvenile rheumatoid arthritis; laryngeal edema; lichen planus; Loeffler's syndrome; lupus nephritis; lupus vulgaris; lymphomatous tracheobronchitis; macular edema; multiple sclerosis; musculoskeletal and connective tissue disorder; myasthenia gravis; myositis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary biliary cirrhosis; pruritus scroti; pruritus/inflammation, psoriasis; psoriatic arthritis; Reiter's disease; relapsing polychondritis; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis. The invention also features the treatment of immune disorders that increase susceptibility to microbial or viral infection, including HIV.

Prognostic Assays

The diagnostic methods described herein can furthermore be utilized to identify subjects having or at risk of developing a disease or disorder associated with aberrant Pin1 expression or activity. For example, the assays described herein, such as the preceding diagnostic assays or the following assays, can be utilized to identify a subject having or at risk of developing a disorder associated with Pin1 marker (e.g., an immune disorder). Thus, the present invention provides a method for identifying a disease or disorder associated with aberrant Pin1 expression or activity in which a test sample is obtained from a subject and Pin1 protein or nucleic acid (e.g., mRNA, genomic DNA) is detected, wherein the presence of Pin1 protein or nucleic acid is diagnostic for a subject having or at risk of developing a Pin1-associated disorder and are, therefore, susceptible to treatment with a retinoic acid compound.

Furthermore, the present invention provides methods for determining whether a subject can be effectively treated with a retinoic acid compound for a disorder associated with aberrant Pin1 expression or activity in which a test sample is obtained and Pin1 protein or nucleic acid expression or activity is detected (e.g., wherein the abundance of Pin1 protein or nucleic acid expression or activity is diagnostic for a subject that can be administered the agent to treat a disorder Pin1-associated disorder).

In one embodiment, the present invention provides methods for determining Pin1 post-translational modifications. More importantly, phosphorylation of Pin1 on Ser71 in the catalytic active site also prevents retinoic acid compounds from binding to Pin1 active site and induce Pin1 degradation and to inhibit Pin1 function. Therefore, by detecting reduced Ser71 phosphorylation using phospho-specific Pin1 antibodies that we have generated can be a method to select patients for RA treatments and to explain some patients may not respond to RA.

The methods of the invention can also be used to detect genetic alterations in a Pin1 gene, thereby determining if a subject with the altered gene is at risk for a disorder associated with the Pin1 gene and, consequently, a candidate for retinoic acid therapy. In preferred embodiments, the methods include detecting, in a sample of cells from the subject, the presence or absence of a genetic alteration characterized by at least one of an alteration affecting the integrity of a gene encoding a Pin1-protein, or the misexpression of the Pin1 gene. For example, such genetic alterations can be detected by ascertaining the existence of at least one of 1) a deletion of one or more nucleotides from a Pin1 gene; 2) an addition of one or more nucleotides to a Pin1 gene; 3) a substitution of one or more nucleotides of a Pin1 gene, 4) a chromosomal rearrangement of a Pin1 gene; 5) an alteration in the level of a messenger RNA transcript of a Pin1 gene, 6) aberrant modification of a Pin1 gene, such as of the methylation pattern of the genomic DNA, 7) the presence of a non-wild type splicing pattern of a messenger RNA transcript of a Pin1 gene, 8) a non-wild type level of a Pin1-protein, 9) allelic loss of a Pin1 gene, and 10) inappropriate post-translational modification of a Pin1-protein. As described herein, there are a large number of assay techniques known in the art which can be used for detecting alterations in a Pin1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the Pin1-gene (see Abravaya et al. (1995) Nucleic Acids Res 0.23:675-682). This method can include the steps of collecting a sample from a patient, isolating nucleic acid (e.g., genomic, mRNA or both) from the sample, contacting the nucleic acid sample with one or more primers which specifically hybridize to a Pin1 gene under conditions such that hybridization and amplification of the Pin1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874-1878), transcriptional amplification system (Kwoh, D. Y. et al, (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Pin1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531; hereby incorporated by reference) can be used to score for the presence of specific mutations by development or loss of a ribozyme cleavage site.

In other embodiments, genetic mutations in Pin1 can be identified by hybridizing a sample and control nucleic acids, e.g., DNA or RNA, to high density arrays containing hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in Pin1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Pin1 gene and detect mutations by comparing the sequence of the sample Pin1 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the Pin1 gene include methods in which protection from cleavage agents is used to detect mismatched bases in RNA/RNA or RNA/DNA heteroduplexes (Myers et al. (1985) Science 230: 1242). In general, the art technique of "mismatch cleavage" starts by providing heteroduplexes formed by hybridizing (labeled) RNA or DNA containing the wild-type Pin1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Nat Acad Sci USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Pin1 cDNAs obtained from samples of cells. For example, the mutY enzyme of $E.\ coli$ cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a Pin1 sequence, e.g., a wild-type Pin1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039; hereby incorporated by reference.

In other embodiments, alterations in electrophoretic mobility will be used to identify mutations in Pin1 genes. For example, single strand conformation polymorphism (SSCP) may be used to detect differences in electrophoretic mobility between mutant and wild type nucleic acids (Orita et al. (1989) Proc Natl. Acad. Sci. USA: 86:2766, see also Cotton (1993) Mutat Res 285:125-144; and Hayashi (1992) Genet Anal Tech Appl 9:73-79). Single-stranded DNA fragments of sample and control Pin1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner et al. (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Pin1 gene.

Furthermore, any cell type or tissue in which Pin1 is expressed may be utilized in the prognostic assays described herein.

As with the diagnostic assay described above, prognostic assays of Pin1 activity can be included as part of a panel of target genes.

Additional methods of detecting Pin1 activity and diagnosing Pin1 related disorders are disclosed in U.S. Patent Application Publication Nos.: 2009/0258352, 2008/0214470, 2006/0074222, 2005/0239095, US2002/0025521, U.S. Pat. No. 6,495,376, and PCT Application Publication No. WO02/065091, each of which is hereby incorporated by reference in its entirety.

Monitoring the Effects of Retinoic Acid Treatment

In one embodiment, the present invention features a method for monitoring the effectiveness of treatment of a subject with a retinoic acid compound comprising the steps of (i) obtaining a pre-administration sample from a subject prior to administration of the compound; (ii) detecting the level of expression or activity of a Pin1 protein, Pin1 phosphorylation on Ser71, mRNA, or genomic DNA in the pre-administration sample; (iii) obtaining one or more post-administration samples from the subject; (iv) detecting the level of expression or activity of the Pin1 protein, mRNA, or genomic DNA in the post-administration samples; (v) comparing the level of expression or activity of the Pin1 protein, mRNA, or genomic DNA in the pre-administration sample with the Pin1 protein, mRNA, or genomic DNA in the post administration sample or samples; and (vi) altering the administration of the retinoic acid compound to the subject accordingly. According to such an embodiment, Pin1 expression, phosphorylation or activity may be used as an indicator of the effectiveness of the retinoic acid compound, even in the absence of an observable response.

III. Methods of Treatment

The present invention provides for both prophylactic and therapeutic methods of treating a subject at risk of (or susceptible to) or afflicted with an immune disorder (e.g., a disorder associated with increased Pin1 expression or activity) with a retinoic acid compound.

Prophylactic Methods

In one aspect, the invention provides a method for preventing an immune disorder in a subject by administering to the subject a retinoic acid compound. Subjects at risk for a disease which is caused or contributed to by aberrant Pin1 expression or activity can be identified by, for example, any or a combination of diagnostic or prognostic assays as described herein. Administration of a retinoic acid compound can occur prior to the manifestation of symptoms characteristic of the Pin1 aberrancy, such that a disease or disorder is prevented and/or its progression delayed.

Combination Therapies

Anti-inflammatory agents are useful for treating immune disorders in combination with the retinoic acid compounds of the invention. Anti-inflammatory agents that can be used in combination with a retinoic acid compound include, without limitation, corticosteroids, NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin), COX-2 inhibitors (e.g., rofecoxib, celecoxib, valdecoxib, and lumiracoxib), biologics (e.g., inflixamab, adelimumab, etanercept, CDP-870, rituximab, and atlizumab), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate, leflunomide, minocycline, auranofin, gold sodium thiomalate, aurothioglucose, and azathioprine), hydroxychloroquine sulfate, and penicillamine.

In cases where there is a viral or microbial infection, the retinoic acid compounds of the invention can be administered with an antimicrobial agent, e.g., the penicillins (e.g., penicillin G, ampicillin, methicillin, oxacillin, and amoxicillin), the cephalosporins (e.g., cefadroxil, ceforanid, cefotaxime, and ceftriaxone), the tetracyclines (e.g., doxycycline, minocycline, and tetracycline), the aminoglycosides (e.g., amikacin, gentamycin, kanamycin, neomycin, streptomycin, and tobramycin), the macrolides (e.g., azithromycin, clarithromycin, and erythromycin), the fluoroquinolones (e.g., ciprofloxacin, lomefloxacin, and norfloxacin), and other antibiotics including chloramphenicol, clindamycin, cycloserine, isoniazid, rifampin, and vancomycin. Particularly useful formulations contain aminoglycosides, including for example amikacin, gentamicin, kanamycin, neomycin, netilmicin, paromomycin, streptomycin, and tobramycin, or an antiviral agent, e.g., 1-D-ribofuranosyl-1,2,4-triazole-3 carboxamide, 9→2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Such compounds can act synergistically with a retinoic acid compound. Additionally, co-administration with a retinoic acid compound may result in the efficacy of the anti-inflammatory compound at lower (and thus safer) doses (e.g., at least 5% less (e.g., at least 10%, 20%, 50%, 80%, 90%, or even 95%) less than when the anti-inflammatory compound is administered alone.

Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the patient, the stage and type of the patient's disease, and how the patient responds to the treatment. Additionally, a person having a greater risk of developing an immune disease may receive treatment to inhibit or delay the onset of symptoms.

Routes of administration for the various embodiments include, but are not limited to, topical, transdermal, nasal, and systemic administration (such as, intravenous, intramuscular, subcutaneous, inhalation, rectal, buccal, vaginal, intraperitoneal, intraarticular, ophthalmic, otic, or oral administration). As used herein, "systemic administration" refers to all nondermal routes of administration, and specifically excludes topical and transdermal routes of administration.

In combination therapy (e.g., a retinoic acid compound with a second therapeutic agent), the dosage and frequency of administration of each component of the combination can be controlled independently. For example, one compound may be administered three times per day, while the second compound may be administered once per day. Combination therapy may be given in on-and-off cycles that include rest periods so that the patient's body has a chance to recover from any as yet unforeseen side effects. The compounds may also be formulated together such that one administration delivers both compounds.

Each compound of the combination may be formulated in a variety of ways that are known in the art. For example, the first and second agents may be formulated together or separately. Desirably, the first and second agents are formulated together for the simultaneous or near simultaneous administration of the agents. Such co-formulated compositions can include the two drugs together in the same pill, ointment, cream, foam, capsule, liquid, etc. It is to be understood that, when referring to the formulation of combinations of the invention, the formulation technology employed is also useful for the formulation of the individual agents of the combination, as well as other combinations of the invention. By using different formulation strategies for different agents, the pharmacokinetic profiles for each agent can be suitably matched.

The individually or separately formulated agents can be packaged together as a kit. Non-limiting examples include kits that contain, e.g., two pills, a pill and a powder, a suppository and a liquid in a vial, two topical creams, ointments, foams etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

IV. Experimental Results

Pin1 is Activated and Specifically Required for Type I IFN Secretion Following TLR Ligation To examine the role of Pin1 in TLR signaling, we first compared cytokine production in response to various TLR ligands using DC subsets derived from Pin1 wild-type (WT, +/+) and Pin1 knockout (KO, −/−) mice. When stimulated with LPS (TLR4 ligand), Pam3 CSK4 (TLR2), R848 (TLR7) or CpG DNA (TLR9), Pin1 KO myeloid DCs (mDCs) produced moderately less proinflammatory cytokines than Pin1 WT controls (Fig. a-c). Consistently, reduced proinflammatory cytokine secretion was also detected following stimulation of Pin1 KO macrophages with each of the TLR ligands (FIG. 10a, b). Stimulation of splenic plasmacytoid DCs (pDC) or Flt3 ligand-induced bone marrow pDCs with purified TLR7 or TLR9 ligand or with the influenza A virus (H1N1) (TLR7) or MCMV (TLR9) showed robust IFN-α secretion in Pin1 WT cells (FIG. 1d-g), as shown. However, Pin1 KO cells almost completely failed to produce IFN-α or IFN-β, as assayed by ELISA (FIG. 1d-g) and qRT-PCR analyses (FIG. 1h). These effects of Pin1 deficiency on IFN-α production were highly specific because Pin1 KO neither affected the population of immune cells nor their TLR expression (FIG. 1l). Moreover, Pin1 enzymatic activity, although not its protein level, was significantly elevated in R848- or CpG-stimulated human peripheral blood mononuclear cells (FIG. 1i), which is consistent with the findings that Pin1 is kept inactivated until cellular cues are engaged. Thus, Pin1 plays a moderate role in proinflammatory cytokine production in mDCs in response to various TLR ligands, but unexpectedly, is essential and specific for the type I IFN response in pDCs following TLR 7/9 ligation.

Proteomic Approach Identifies IRAK1 as a Major Pin1 Substrate Upon TLR Stimulation.

Figure 1:
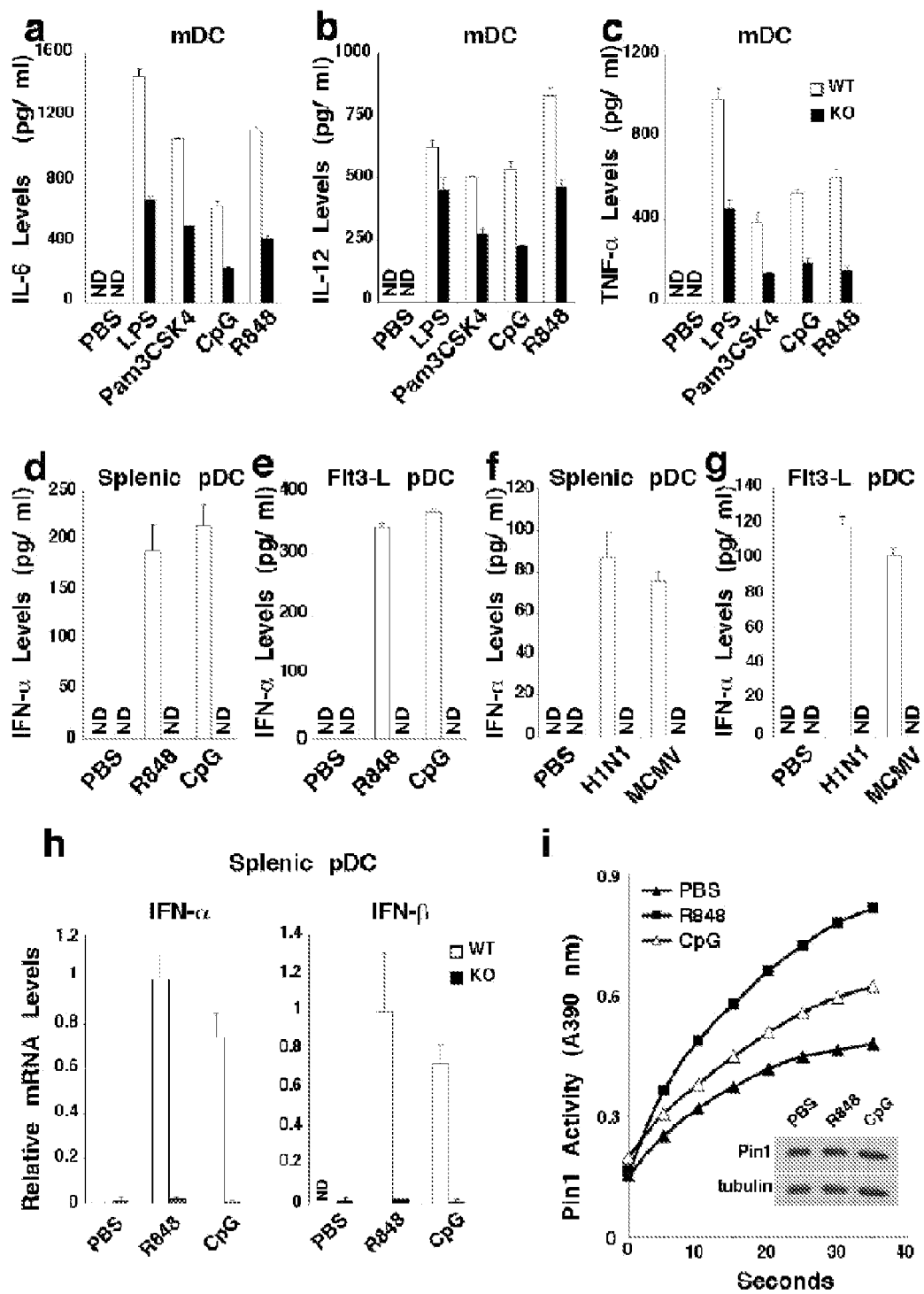
FIG. 1: Pin1 is activated and required for cytokine and especially type I IFN secretion following TLR stimulation.

To elucidate the molecular mechanism underlying the impact of Pin1 on type I IFN secretion, we used a proteomic approach to identify Pin1 substrates using a GST-Pin1 affinity purification procedure under high-salt and -detergent conditions, a procedure that has been used to identify almost all known Pin1 substrates. We used R848-stimulated human THP1 cells, a monocytic cell line that has a functional IFN response to TLR 7/9 ligands and can be cultured in sufficient volumes. Following SDS-PAGE and mass spectrometry, one prominent and reproducible Pin1-binding protein at 100 kDa was identified to be IRAK1 (FIG. 2a and FIG. 12a). Notably, the Pin1 KO phenotypes shown in FIG. 1 are strikingly similar to those observed in IRAK1 KO cells and mice. Furthermore, similar to IRAK1 KO, no obvious effect of Pin1 deficiency on IL-6 and IL-12p40 levels could be detected following pDCs stimulated with R848 or CpG (FIG. 10c, d). Moreover, no difference was observed for IFN-β section from Pin1 WT and KO mDCs stimulated with CpG (FIG. 10e), which is consistent with the previous results that CpG stimulation of mDCs induces IFN-β production in a MyD88- and IKKα-dependent but IRAK1-independent manner. These results prompted us to examine the role of Pin1 in regulating IRAK1 function in TLR signaling. We confirmed the TLR7/9-dependent interaction between IRAK1 and Pin1 in THP1 monocytes and Raw264.7 macrophages by GST-Pin1 binding assay (FIG. 2b) or co-immunoprecipitation (Co-IP) (FIG. 2c). Pin1 predominantly bound to the activated form of IRAK1, which displayed a characteristic mobility shift on SDS gels after TLR ligation (FIG. 2b, c, arrows), suggesting that Pin1 might bind specifically to phosphorylated IRAK1. Indeed, this binding was mediated by the Pin1 WW domain (FIG. 12b, d), a known pSer/Thr-Pro-binding module, but was abolished either by IRAK1 dephosphorylation prior to Pin1 binding assay (FIG. 2d, 12c) or mutating a key functional residue in the WW domain (FIG. 12b, e). In addition, Pin1 did not bind to the related kinases IRAK2 and IRAK4 following TLR7 and TLR9 stimulation (FIG. 12f). Thus, following TLR 7/9 ligation, Pin1 is activated and IRAK1 is phosphorylated, which allows Pin1 to interact specifically with IRAK1.

The binding of Pin1 to IRAK1 was somewhat surprising because Pin1 interacts only with specific pSer/Thr-Pro motifs and there is little known about Pro-directed phosphorylation of IRAK1 in TLR signaling. Consequently, we decided to define the Pin1 binding region and site(s) in IRAK1. Structurally, IRAK1 consists of an N-terminal death domain, a ProST-rich undetermined domain (UD) and a central kinase domain, with a C-terminal tail (FIG. 13a). To avoid interference of endogenous IRAK1, we expressed FLAG-IRAK1 or its mutants in IRAK1 null (I1A) 293 cells, followed by Pin1 binding assay. Under overexpression conditions, IRAK1, but not its K239S kinase-dead (KD) mutant, was auto-activated independently of TLR stimulation, as indicated by the characteristic mobility shift (FIG. 2d, f, 13b), as shown previously. Importantly, IRAK1, but not its KD mutant, interacted with Pin1 (FIG. 2f, g, 13b). Furthermore, deletion of the UD, abolished Pin1 binding (FIG. 13b). Thus, Pin1 binds to kinase active IRAK1, possibly through autophosphorylation sites in the UD.

To directly examine this possibility in vivo, we co-expressed FLAG tagged KD-IRAK1 with or without WT-IRAK1 in IRAK1-deficient cells, followed by analyzing Pin1 binding specifically to KD-IRAK1. As shown previously, KD-IRAK1 did not show the characteristic mobility shift and failed to interact with Pin1 when it was expressed alone (FIG. 2e left). However, when co-expressed with WT-IRAK1, KD-IRAK1 showed the mobility shift and, importantly, also bound to Pin1 (FIG. 2e right), suggesting that Pin1 binds to autophosphorylated IRAK1. To confirm that Pin1 directly binds to IRAK1, we performed Far-Western blotting analysis using WT and KD IRAK1 and GST-Pin1 WW domain. Indeed, Pin1 bound only to the slower mobility shifted and presumably activated form of WT IRAK1, but there was no binding between Pin1 and KD IRAK1 (FIG. 2f). Finally, to confirm the binding of Pin1 to the active form of IRAK1, we performed Pin1 binding assay using mouse embryonic fibroblasts (MEFs) stably infected with WT and KD IRAK1 in the presence or absence of TLR7 activation. Pin1 bound to the active form of WT IRAK1, but not KD IRAK1 confirming that Pin1 predominately binds to activated IRAK1 (FIG. 2g). Taken together, these results indicate that upon TLR ligation, IRAK1 is activated by receptor recruitment and autophosphorylates on the pSer-Pro motifs, which in turn recruits Pin1 to act on IRAK1.

To identify the IRAK1 phosphorylation site(s) responsible for Pin1 binding, we mutated each of the six possible Pin1 binding pSer/Thr-Pro motifs in the UD of IRAK1 to Ala, and assessed their binding to Pin1 from retrovirally infected cells. Although the mutation of S110, S163 or S196 had little effect on Pin1 binding, the mutation of S131, S144 or S173 alone to Ala considerably reduced IRAK1 activation and Pin1 binding, which was further reduced when all three sites were mutated together (FIG. 2h), indicating that phosphorylation of these sites participate in regulating IRAK1 activation and Pin1 binding. To confirm the phosphorylation status of these three sites, we used a two-step purification procedure to isolate IRAK1 using sequential FLAG immunoprecipitation and GST-Pin1 pulldown, followed by LC-MS analysis. Both S131 and S144 were indeed phosphorylated (FIG. 14a, b). However, both typsin and chymotrypsin digestions repeatedly failed to produce any peptides covering the region surrounding S173 (FIG. 14e), possibly due to the numerous proline and hydrophobic residues in this region. This prompted us to generate phospho-specific antibodies against phosphorylated S173 of IRAK1. The resulting anti-pS173 antibodies specifically recognized activated WT IRAK1, but not its S173A point mutant, even when it was highly overexpressed and activated using transient transfection, confirming that S173 in the UD of IRAK1 is indeed phosphorylated (FIG. 15a). Moreover, S173 phosphorylation of IRAK1 was significantly induced in R848- or CpG-stimulated human peripheral blood mononuclear cells, as determined by flow cytometric (FIG. 2i) and Western blot (FIG. 15b) analysis using pS173-specific IRAK1 antibodies. Taken together, these results indicate that upon TLR activation, S131/144/173-Pro motifs in the UD of IRAK1 are not only phosphorylated in cells, but also are largely responsible for Pin1 binding.

Pin1 Binds and Isomerizes Each of the Phosphorylated-S13/S144/S173-Pro Motifs in the UD of IRAK1.

The Pin1 WW domain and PPIase domains have been shown to bind and isomerize specific pSer/Thr-Pro motifs in its substrates, respectively. To measure the Pin1 interaction with each of the implicated pSer-Pro motifs in IRAK1, we employed two-dimensional (2D) NMR spectroscopy to monitor the changes in the $^{15}$N-WW domain induced by titration with phosphopeptide ligands. In a 2d $^{15}$N-$^{1}$H HSQC spectrum of a protein (FIG. 3a), each backbone NH group is represented by a peak, whose position reflects the chemical environment of that NH bond. Ligand binding to the protein is detected by changes in peak positions (fast exchange) or by the appearance of new peaks (slow exchange) as ligand is added. WW binding at each distinct IRAK1 site was measured using phosphopeptides containing residues 126-136 (pSer131-P132), 140-150 (pSer131-P132), and 157-180 (pSer173-P174) of IRAK1. The WW domain bound to each phosphopeptide and exhibited fast exchange kinetics, as demonstrated by changes in peak position, in each of the three titration experiments (FIG. 3a). Quantitative analysis of the change in chemical shift as a function of peptide concentration (FIG. 3b) yielded dissociation constants ($K_D$) of 220±15 µM, 120±12 µM, and 260±75 µM for the 126-136 (pSer131-P132), 140-150 (pSer131-P132), and 157-180 (pSer173-P174) phosphopeptides, respectively. The IRAK1-Pin1 interaction in the cell occurs as part of a multi-protein membrane-associated complex, suggesting the potential for significant binding enhancement due to avidity.

In order to determine whether Pin1 catalysis occurs at each of these sites, the homonuclear 20 ROESY NMR experiment was used as we have previously reported. In the presence of a catalytic amount of Pin1, exchange crosspeaks between the cis and trans isomers of the pSer-Pro peptide bond were clearly observed for each peptide (FIG. 3c, top panels). Conversely, in the absence of Pin1, exchange crosspeaks were missing (FIG. 3c, bottom panels). These results demonstrate that Pin1 accelerates the cis-trans isomerization at each pSer-Pro motif, thereby confirming these sites as Pin1 substrates.

Pin1 is Essential for IRAK1 Activation Upon TLR Ligation.

Given that Pin1 binds to and isomerizes multiple pSer-Pro motifs in IRAK1 upon TLR activation, a key question is whether Pin1 regulates IRAK1 function in TLR signaling. Therefore, we examined the effects of Pin1 KO on IRAK1 activation in response to activation of various TLRs using Pin1 WT and KO MEFs and pDCs. Although TLR7/9 ligation activated IRAK1 in a time dependent fashion in both Pin1 WT cells (FIG. 4a), as indicated by the mobility shift and increased kinase activity (FIG. 4b), as previously described, there was no evidence for IRAK1 activation in either assay in Pin1 KO MEFs or pDCs (FIG. 4a, b) or in Pin1-silenced THPI cells using RNAi (FIG. 4c). Moreover, Pin1 KO also completely abolished IRAK1 activation in response to ligation of other TLRs including TLR2 and TLR4 (FIG. 16a, b). These effects were highly specific because Pin1 KO did not affect activation of the IRAK1 upstream kinase IRAK4 (FIG. 4b), or MAP kinases including ERKs, JNKs and p38 MAPKs upon TLR activation (FIG. 17). Similar observations were made following LPS stimulation of macrophages (FIG. 18a). We also assessed the effects of Pin1 deficiency on IKB degradation following pDC stimulation with R848 and CpG or treatment of macrophages with LPS and did not see any obvious difference between Pin1 WT and KO cells (FIG. 18b, c). To further confirm this effect of Pin1 on IRAK1 activation, we developed an assay to measure the kinase activity of IRAK1 in cells utilizing the fact that IRAK1 can phosphorylate the N-terminal 220 aa IRAK1 fragment containing the UO in trans, as shown by the characteristic mobility shift after co-expression with WT IRAK1 (FIG. 4d), as shown previously. As expected, exogenously expressed IRAK1 in Pin1 WT MEFs efficiently phosphorylated the IRAK1 N-terminal fragment, inducing the characteristic mobility shift (FIG. 4D). However, like KD IRAK1, WT IRAK1 in Pin KO MEFs completely failed to induce any mobility shift of the N-terminal IRAK1 (FIG. 4d). These results together indicate that Pin1 is required for IRAK1 activation.

To further demonstrate the importance of Pin1 for the time dependent activation of IRAK1 following TLR ligation, we overexpressed WT IRAK1 and KD IRAK1 in Pin1 WT and KO MEFs using a retroviral expression system. Under overexpression conditions, WT-IRAK1 was partially activated, which was further activated upon TLR7 ligation in Pin1 WT cells, as shown by the characteristic mobility shift (FIG. 4e), consistent with the findings that IRAK1 activation is sensitive to IRAK protein levels. However, no IRAK1 activation was observed in Pin1 KO cells, even after stimulation (FIG. 4e), further confirming the role of Pin 1 in IRAK1 activation. Importantly, KD IRAK1 did not show any evidence of activation following TLR ligation both in Pin1 WT and KO cells (FIG. 4e). These results indicate that IRAK1 fails to be activated in Pin1 KO cells. To confirm that defective IRAK1 activation in Pin1-null cells is specifically due to loss of Pin1 and to examine the importance of Pin1 binding and isomerase activities for IRAK1 activation, we performed rescue experiments by re-expressing WT Pin1 or its point mutants, W34A mutant (in the WW domain) or K63A mutant (in the catalytic domain), which fail to bind to or isomerase Pin1 substrates, respectively. Re-expression of Pin 1, but neither of its WW domain (W34A) nor catalytic domain (K63A) point mutants completely restored IRAK1 activation in Pin1 KO cells expressing IRAK1 (FIG. 4f), reminiscent of IRAK1 activation found in Pin1 WT cells (FIG. 4e). Taken together, these results demonstrate an essential role for Pin1 in IRAK1 activation in TLR signaling.

Pin1 Bound to IRAK1 and NF-κB, and Pin1 KO Abolished IRAK1 Activation, $Ca^{2+}$ Flux and NF-κB Activation by IL-33.

GST-Pin1 pulldown showed that Pin1 bound only to activated IRAK1 in monocytes after IL-33 stimulation (FIG. 20A), similar to TLR ligation. IL-33 induced IRAK1 activation in Pin1 WT, but not KO MEFs (FIG. 20B). IL-33 induced $Ca^{2+}$ flux in eosinophils derived from Pin1 WT, but not KO BM (FIG. 20C), as described. Pin1 also bound only to activated p65 NF-κB via the Ser254-Pro motif after IL-33 stimulation (FIG. 20D, E), as we have shown after cytokine stimulation. Moreover, IL-33 induced NF-κB activation in Pin1 WT, but not Pin1 KO cells (FIG. 20F), consistent with the fact that $Ca^{2+}$ flux activates NF-κB.

Preliminary NMR Results.

To demonstrate feasibility of Pin1 rate measurements, a single $^{15}N$ label was incorporated at $Ala_{175}$ in $UD_{157-180}$ (FIG. 20G) to monitor the nearby $pS_{173}P$ motif using NMR studies. Because uncatalyzed cis-trans isomerization is a generally slow process (time constant minutes), the equilibrium between cis and trans isomers yields two distinct peaks for residues (such as $A_{175}$) whose chemical environment differs in the two isomer states. To investigate Pin1 catalysis of the $pS_{173}P$ motif, the two-dimensional $^{15}N$-$^{1}H$ $N_{zz}$ exchange spectroscopy of [$^{15}N$-$Ala_{175}$]$UD_{157-180}$ (1 mM) in the presence of Pin1 (17 μM) was used, as we have describe, revealing cis and trans conformations of the $pS_{173}P$ bond (peaks labeled cc and tt) whose exchange is catalyzed by Pin1 (FIG. 20H, inset). Cross-peaks (labeled ct and tc) demonstrate Pin1-catalyzed exchange between cis and trans isomers. The dependence of peak intensities on $N_{zz}$ mixing time yields the cis-trans exchange rate. An example fitting of the $N_{zz}$ data for $^{15}N$-$Ala_{175}$-$UD_{157-180}$ demonstrates the high quality of the data and fit (FIG. 20H), yielding a Pin1-catalyzed isomerization rate for the $pS_{173}P$ peptide bond of $k_{ex}=27\ s^{-1}$. Based on peak intensities in the absence of Pin1, the $pS_{173}P$ trans:cis ratio is 85:15. Additionally, to demonstrate the feasibility of NMR studies on the intact IRAK1-UD, the $^{15}N$-$^{1}H$ fHSQC spectrum of recombinant $^{15}N$-labeled IRAK1-$UD_{101-222}$ (IRAK1 residues 101-222) (FIG. 20I) showed limited peak dispersion, characteristic of a disordered sequence, and will allow detection of conformational changes in the IRAK1-UD. This spectrum displays several minor peaks that are attributed to the cis isomers of the various X-Pro peptide bonds, allowing residue-specific detection of changes in populations of cis and trans states.

Pin1 is Essential for IRAK1-Dependent IRF7- and IFN-α-Mediated Antiviral Response in Vitro.

Given that Pin1 was required for activation of IRAK1 we wondered whether Pin1 regulates IRAK1 mediated downstream signaling. Following TLR activation, IRAK1 is recruited to the receptor complex via MyD88IRAK4, where it is activated and released from the receptor complex. This allows transcription factors such as IRF7, the master regulator of IFN-α. to translocate into the nucleus where it activates IFN-α transcription, making IRAK1 activation a key step in the TLR7/9 signaling cascade. Therefore, we examined whether Pin1 KO affects the ability of IRAK1 to transduce TLR signals.

To address whether IRAK1 is still recruited to the TLR receptor complex in Pin1 KO cells, we transfected HA-MyD88 into both Pin1 WT and KO cells retrovirally expressing FLAGIRAK1, followed by immunoprecipitation with anti-HA antibodies and then immunoblotting with anti-FLAG antibodies. As shown previously, the activated form of IRAK1 in Pin1 WT cells was not readily found in the MyD88 immune complexes (FIG. 5a). However, IRAK1 in Pin1 KO cells formed a stable interaction with HA-MyD88 (FIG. 5a), presumably due to the fact that IRAK1 is not fully activated in these cells (FIG. 4a, Thus it appears that IRAK1 in Pin1 KO cells is unable to dissociate from the receptor complex due to its lack of autophosphorylation, presumably retaining IRAK1 at the receptor complex.

Given that Pin1 is required for IRAK1 activation and dissociation from the receptor complex, we examined whether Pin1 affects IRF7 activation using Pin1 knockdown and knockout. Pin1 knockdown in THP1 cells using Pin1-RNAi not only abolished the IRF7 and TRAF6 interaction, as shown by Co-IP experiments (FIG. 5b), but also blocked IRF7 nuclear translocation in response to TLR 7/9 activation, as determined by subcellular fractionation followed by immunoblotting analysis (FIG. 5c, d). To further confirm these results, we immunostained for IRF7 in primary Pin1 WT and KO pDCs after TLR7/9 ligation. Upon TLR activation, IRF7 translated to the nucleus in Pin1 WT. but not Pin1 KO pDCs (FIG. 5e). These results suggest that Pin1 activates IRAK1 to cause IRF7 nuclear translocation in response to TLR 7/9 stimulation.

This suggestion was further supported by our findings from IRAK1-mediated IRF7 functional assays. Specifically, Pin1 KO abolished IRF7 reporter activity following TLR7/9 stimulation (FIG. 6a, b), and these defects were fully rescued by Pin1, but not its binding-inactive- or isomerase-defective mutant, as measured by IRF7 reporter activity and IFN-α production (FIG. 6c, d). To further investigate the role of Pin1 and IRAK1 kinase activity in IRF7 activation, we co-expressed MyD88, a Gal4-IRF7 reporter construct and various amounts of KD IRAK1 in Pin1 WT and KO MEFs. IRF7 activation in WT cells decreased as the amount of transfected KD IRAK1 was increased. In contrast. IRF7 activation was consistently lower in Pin1 KO cells and unaffected by the amount of KD IRAK1 transfected (FIG. 6e). These results demonstrate that both Pin1 and IRAK1 kinase activity are necessary for activation of IRF7. These findings are consistent with the previous findings 1) that IRAK1, but not its KD mutant, phosphorylates IRF7, 2) that IRAK1 kinase activity is necessary for the transcriptional activity of IRF7, but not NF-κB, 3) that KD IRAK1 inhibits MyD88-induced IRF7 activation in a dominant-negative manner, and 4) that inhibition of IRAK kinase activity with a synthetic inhibitor prevents IRF7 phosphorylation, but not NF-κB phosphorylation in CpG stimulated pDCs.

Moreover, the IRAK1 mutations that prevented Pin1 binding in retrovirally infected MEFs including S131A, S144A and S173A alone or together also decreased IRF7 promoter activation and IFN-α secretion similar to kinase-inactivating IRAK1 mutation or Pin1 KO (FIG. 6f, g). To confirm the importance of Pin1 in IRAK1- and IFN-α-mediated antiviral activity, we performed plaque formation assays using GFP-expressing vesicular stomatitis virus (VSV). Specifically, L929 cells were infected with GFP-VSV and incubated with supernatants from Pin1 WT and KO MEFs expressing IRF7 and IRAK1 or its mutants, followed by GFP-positive plaque quantification. While supernatants from Pin1 WT MEFs expressing WT IRAK1 had potent antiviral activity, those from Pin1 WT MEF expressing Pin1 binding IRAK1 mutants or KD IRAK1 had little activity, similar to Pin1 KO MEFs (FIG. 6h, i), consistent with IRF7 activity and IFNα production in these cells (FIG. 6f, g). Thus, disrupting the IRAK1 activation by inhibiting Pin1 or by preventing IRAK1 from acting as a Pin1 substrate drastically abrogates IRF7 activation, subsequent IFN-α production and antiviral response in vitro.

Pin1 is Required for Type I Interferon-Mediated Innate and Adaptive Immunity In Vivo.

Given the essential role for Pin1 on IRAK1-dependent antiviral cellular responses in vitro, we next examined the effects of Pin1 KO in vivo using Pin1 WT and KO mice. Following injection with R848 or CpG, robust IFN-α production could be observed in Pin1 WT mice (FIG. 7a, b), as shown. In contrast, serum IFN-α levels in Pin1 KO littermates were significantly reduced (FIG. 7a, b). When injecting mice with LPS or R848, the serum levels of IL-6 and IL-12p40 were significantly lower in Pin1 KO mice, compared to WT controls, albeit not as dramatically as IFN-α levels (FIG. 19a-c). As the MyD88-IRF7 pathway has been shown to be essential for IFN-α production during MCMV infection, we next examined the effects of Pin1 KO on systemic MCMV infection. Whereas IFN-α levels in Pin1 WT animals peaked after 36 hours following MCMV infection, IFN-α induction was entirely suppressed in Pin1 KO mice (FIG. 7c). Moreover, Pin1 KO mice were much more vulnerable to systemic MCMV infection than their WT littermates, resulting in increased weight loss (FIG. 7d) and morbidity (FIG. 7e). These phenotypes are similar to those observed in IRF7 or MyD88 KO mice and further highlight the contribution of Pin1 to the antiviral immune response in vivo.

Co-stimulation of TLR9 and CD40 induces CD8 T-cell expansion in a pDC, IRF7 and IFN-α dependent manner, thereby playing a major role in regulation of adaptive immune responses. To study the effects of Pin1 deficiency on adaptive immunity, we next investigated the effects of Pin1 KO on the induction of antigen-specific CD8$^+$ T-cell responses. As reported, treatment with ovalbumin and anti-CD40 alone did not induce specific CD8$^+$ T-cell expansion, whereas co-inoculation of CpG-A complexed to DOTAP, a CD40 agonistic antibody and ovalbumin induced a strong expansion of antigen-specific CD8$^+$ T-cells in Pin1 WT mice (FIG. 7f, left). In contrast, the ovalbumin-specific CD8$^+$ T-cell response was greatly impaired in Pin1-deficient mice (FIG. 7f, right). Taken together, these results demonstrate a crucial role for Pin1 in mediating both adaptive and innate immunity.

Pin1 regulates upstream and downstream targets in TLR/IL-1R signal pathways in multiple cells in asthma based on our following results. 1) TLR7/9 activates Pin1, which in turn is critical for activation of IRAK1 in TLR7/9 signaling in vitro and in vivo. 2) IL-33 activated Pin1 and IRAK1, similarly to TLR stimulation. 3) Pin1 KO almost fully abrogated Th2 cytokine production induced by IL-33 in mice and in vitro. 4) Pin1 KO effectively suppressed asthma-like pathologies in mice induced by IL-33. 5) Pin1 KO suppressed cytokine production induced by HDM or LPS.

Pin1 is Activated by IL-33 and Pin1 KO Suppressed IL-33-Induced Th2 Cytokine Production and Asthma-Like Phenotypes in Mice.

We found that IL-33 stimulation activated Pin1 catalytic activity in THP-1 monocytes (FIG. 28A) and BM-derived eosinophils (FIG. 35B), with the extent of the activation being similar to that found in eosinophils in asthmatic airways. Importantly, Pin1 KO abolished the ability of IL-33 to induce IL-6 production in mouse embryonic fibroblasts (MEFs) (FIG. 28B), which have been shown to express ST2. Moreover, Pin1 KO significantly inhibited Th2 cytokine secretion in BAL fluids, lung inflammation and mucus hypersecretion induced by IL-33 (FIG. 28C-F). This phenotype is similar to what is observed in animals treated with soluble ST2 or IL-33 neutralizing antibody to inhibit IL-33 signaling in mouse asthma models.

Pin1 KO Reduced Th2 Cytokine Production and Asthma-Like Phenotypes in Mice after OVA Challenge.

To examine the role of Pin1 on allergic asthma, we examined the effects of Pin1 KO on OVA-induced mouse model of allergic asthma, as described. We found that Pin1 KO significantly inhibited Th2 cytokine secretion, lung inflammation and eosinophilia in BAL fluids after allergen challenge (FIG. 29), which is consistent with the previous findings showing the requirement of Pin1 for pulmonary eosinophilia and bronchiolar remodeling after allergen challenge. Of note, the effects of Pin1 KO in the OVA asthma model (FIG. 29) were not as comprehensive as the i.n. IL-33 model (FIG. 28), which might be due to possibilities that OVA might be a broader allergen model than IL-33, that KO of ST2 has been shown to have more obvious effects in a short-term priming model of asthma and/or that Pin1 might affect other pathways.

Pin1 KO Inhibited Proinflammatory Cytokine Production Induced by HDM or LPS.

We found that Pin1 KO potently suppressed LPS or HDM-induced IL-6 production in MEFs (FIG. 30A, C) and BM-derived mast cells generated using rmIL-3 (FIG. 30D).

Pin1 KO also significantly decreased TLR-induced IL-6 secretion from BM derived macrophages and myeloid dendritic cells (mDCs). Finally, Pin1 KO reduced serum proinflammatory cytokine levels in mice after LPS i.p. (FIG. 30B).

Pin1 is Activated in Patients with Systemic Lupus Erythematosus (SLE).

We asked whether Pin1 is activated in immune cells from patients with SLE and we performed Pin1 immunoblot analysis of lysates of peripheral blood mononuclear cells (PBMC) isolated from six active SLE patients (SLE Disease activity score (SLEDAI)>6) and six normal controls using antibodies recognizing specifically S16 or pS16 in the Pin1 WW domain. We found that Pin1 in PBMC from all healthy individuals examined existed in two forms with different mobility on SDS gels (FIG. 21A). What has attracted our attention is that the slower mobility form was absent in lysates from six SLE patients (FIG. 21A), suggesting that Pin1 might be hypophosphorylated in SLE. Importantly we have previously shown that phosphorylation of Pin1 on S16 in the WW domain (FIG. 22A, B) and S71 in the PPIase domain (FIG. 22C-E) inhibits its ability to bind and isomerizes its substrates, respectively (FIG. 22). To distinguish these phosphorylated forms of Pin1, especially in cells and tissues, we have generated phospho-specific antibodies that recognize pS16 or pS71 form of Pin1 (FIG. 23A). Moreover, our X-ray structure of PKA phosphorylated Pin1 has clearly revealed why phosphorylation of S16 and S71 inhibits its function. S16 is located at the center of the pSer/Thr-binding pocket of the WW domain and pS16 phosphate of formed H-bonds with Ser18 and Ser19, preventing the WW domain from interacting with Pin1 substrates (FIG. 23B). S71 is located at the middle of the pSer/Thr-binding pocket of the PPIase domain and pS71 phosphate formed H-bonds with Arg69, preventing the substrate from entering the catalytic active site (FIG. 23C). To examine whether Pin1 activity is inhibited in patients with SLE, we directly measured Pin1 PPIase activity in PBMC lysates, as described. Pin1 activity was significantly higher in SLE PBMC than normal PBMC (FIG. 21B), consistent with our immunoblot data (FIG. 21A). These results together, albeit preliminary, suggest that Pin1 is activated in SLE patients.

Pin1 Activity May be Determined Genetically.

Previously a leader in human SLE genetics, and we established an association between PPP2CA polymorphisms and susceptibility to SLE in multiple ethnic groups (183) after we had established that PP2Ac is abnormally expressed in SLE T cells and contributed to abnormal T cell function. Pin1 expression has been shown to be controlled by Pin1 promoter SNPs (reduced by SNP rs2233678 (110-112, 181), increased by SNP rs2287839 (182) (Table 1)).

TABLE 1

Frequency of Pin1 SNPs rs2233678 (G > C) and rs2287839 (G > C) in the normal population

|  |  | GG | GC |
|---|---|---|---|
| rs2233678 | Count | 794 | 213 |
|  | (%) | (78.8%) | (21.2%) |
| rs2287839 | Count | 110 | 17 |
|  | (%) | (86.6%) | (13.4%) |

Besides Monocytes and DCs, B Cells and Major T Cell Subsets Also Express Pin1.

Pin1 enzymatic activity, but not Pin1 protein levels, increases in human PBMCs following stimulation with R-848 (TLR7) or CpG (TLR9). Since the number of different cell types in human blood samples is limited, we have now successfully established a highly sensitive icFACS-based method to quantify Pin1 levels in cells using the non-phosphorylated Ser16-specific Pin1 monoclonal antibody (mAb) that was conjugated with APC (Allophycocyanin) The labeled antibody was then used to immunostain splenic B cells with Pin1 wild type (WT) and Pin1 deficient (KO) mouse embryonic fibroblasts (MEFs) as controls, followed by detecting Pin1 levels using a flow cytometer. Pin1 mAb and isotype control mAb generated almost identical signals in Pin1 KO MEFs or B cells (FIG. 24A). However, clear Pin1 staining signals were detected in Pin1 WT MEFs and B cells (FIG. 24Aa). Using this FACS-based quantitative method, we examined whether Pin1 levels change upon stimulation with CpG. Indeed, Pin1 levels in splenic B cells were dramatically increased upon activation of TLR9, which also led to activation of B cells (FIG. 24B) further supporting Pin1 activation upon TLR activation as shown. To detect Pin1 expression in various immune cells, we immunostained unstimulated splenocytes with labeled Pin1 mAb and various immune cell markers, followed by FACS analysis. Pin1 was detected in $CD4^+$ and $CD8^+$ T cells, dendritic cells (DC), macrophages, B cells and granulocytes (data not shown). Thus we have established quantitative approaches to detect Pin1 in immune cell subsets, which we will apply to ask whether Pin1 expression is comparable or altered in T (CD4+, CD8+, CD3+CD4−CD8−, CD69+), B (and subsets), pDCs and monocytes in patients with SLE. Flow cytometry requires fewer cells and we should be able to answer this question without any problems. We expect that at least several types of cells will have altered (increased) levels of non-phosphorylated Pin1. We have shown that besides monocytes and DCs, B cells and major T cell subsets also express Pin.

Activation of Pin1 by PP2A in SLE.

We have shown that in SLE T cells the message, protein and activity of PP2Ac is increased and is involved in their abnormal function. First, PP2Ac dephosphorylates pCREB and accounts for the decreased IL-2 production. Second, PP2Ac dephosphorylates the transcription factor Elf1 and decreases its ability to bind to the promoters of CD3zeta and FcRgamma genes causing suppression of the first and derepression of the second with significant repercussions in the composition of the CD3 complex in SLE T cells. Third, PP2Ac dephosphorylates (and activates) SP1, which binds to the promoter of IL-17A and promotes its expression. Our results show that PP2A not only efficiently dephosphorylated Pin1 that was phosphorylated by PKA (FIG. 25A, B) but also fully restored its PPIase activity (FIG. 25C) in vitro. Furthermore, Pin1 became dephosphorylated in human PMBCs after TLR9 activation by CpG, which was reversed in cells pretreated with okadaic acid at a low concentration that selectively inhibits PP2A (5 nM) (FIG. 25D). Moreover, Pin1 also was dephosphorylated in T cells isolated from CD2:PP2A transgenic mice that overexpresses PP2Ac in T cells developed in Dr. Tsokos laboratory, but not wild-type littermates (FIG. 25E). Therefore, it is reasonable to predict that increased PP2Ac activity may contribute to the dephosphorylation and activation of Pin1 in SLE. Alternatively, because calcineurin (CaN) can also dephosphorylate Pin1 in vitro (FIG. 25) and CaN inhibitors may have a place in the treatment of SLE, we will consider it as a viable alternative to PP2Ac.

Pin1 Conditional Knockout in Immune Cells.

To address if Pin1 in specific cell types contributes to the expression of autoimmunity in lupus prone mice, we recently generated Pin1 conditional knockout (Pin1-CO) mice in B6 background that we have recently generated using the Cre- and loxP-mediated system (FIG. 26A) and confirmed conditional KO by crossing them with Nestin-Cre mice (FIG. 26B).

HTS Identification of Novel Pin1 Inhibitors that Blocked Cytokine Production Induced Using TLR9.

One of the challenges arising from the recent wealth of knowledge on TLR signaling is how to develop a strategy to inhibit specific arms of TLR mediated immune regulation while leaving other critical defensive nodes untouched. Significantly, we have uncovered that Pin1 inhibition completely abrogates activation of IRAK1 kinase, and fully suppresses type 1 IFN production, but with only a moderate effects on pro-inflammatory cytokine production in response to TLR7/9 activation. In addition, hydroxychloroquine, one of the most common used and effective drugs for treating SLE, inhibits stimulation of TLR9. These results suggest that inhibiting Pin1 activity might allow selective inhibition of the type 1 IFN response while leaving other arms of the immune defense proficient. Such Pin1 inhibitory approach might have advantages over conventional immunosuppressing strategies.

In this regard, recently, we identified specific and potent Pin1 catalytic peptidic inhibitors and used them to establish a robust and sensitive FP-based HTS to screen approved drugs and NIH Chemical and Genomics Center, which led us to successfully identify all trans retinoic acid (ATRA) and four other Pin1 inhibitors active in cells for further optimization including Cpd4 (FIG. 27A). Notably, ATRA has been shown to suppress SLE-related phenotypes in some lupus prone mouse models. Our preliminary results showed that ATRA and Cpd4 effectively competed Pin1 catalytic peptidic inhibitors for binding to the Pin1 active site (FIG. 27B) and inhibited its catalytic activity in vitro (FIG. 27C) and inhibited Pin1-dependent cancer cell growth (FIG. 27D) with a similar potency. Furthermore, ATRA also suppressed production of cytokines including IL6, IL12 and TNF-α from pDCs upon TLR9 activation by CpG (FIG. 27F-H). To confirm ATRA as a Pin1 inhibitor, we also solved co-crystal structures of Pin1 and ATRA and found that the carboxylic acid of ATRA formed H-bonds with R68 and K63, residues essential for Pin1 to recognize the substrate phosphate group, while the other end of the molecule formed many hydrophobic interactions with residues critical for recognizing Pro in the substrate (FIG. 27I).

Identification of Trans-RA as a Pin1 Inhibitor.

We developed a fluorescence polarization (FP)-based HTS using fluorescence labeled Pin1 peptidic inhibitor, pTide to identify Pin1 inhibitors. Our screening of selected compounds at the Harvard ICCB-L libraries identified the strongest hit to be cis-RA according to the Z-score (FIG. 31A). To confirm that RAs target Pin1, we examined cis-RA and trans-RA in vitro and in cells. Surprisingly, trans-RA displayed even more potent Pin1 inhibition than cis-RA in FP assays (FIG. 31A), inhibiting Pin1 PPIase assays (FIG. 31B), inhibiting cell growth (FIG. 31C) and reducing Pin1 levels (FIG. 31D) in breast cancer cell lines SKBR3 and T47D, without any effects on normal breast cells (MCF-10A), as expected from Pin1 KD. Cellular Pin1 activity was also reflected by cyclin D1 levels (FIG. 31D), a known Pin1 biomarker. RAs did not alter Pin1 mRNA levels, but increased Pin1 protein turnover in cells, as determined by cycloheximide chase, which might explain their much higher potency in cells than in vitro. Finally, Pin1 KO MEFs were much more resistant to trans-RA, but their drug sensitivity was fully restored by stable re-expression of Pin1, but not its inactive mutant (FIG. 31E).

Determining Trans-RA Structure-Activity Relationship [and Co-Crystal Structure with Pin1].

To Identify the Essential Moiety of Trans-RA for Pin1 Binding, we Tested Commercially Available Retinoids for Pin1 inhibition. Only those with a —COOH group inhibited Pin1, but those with —CHOH or —CHO or —COOCH3 groups were inactive (FIG. 32A). The carboxylic acid of trans-RA formed H-bonds with R68 and K63, residues essential for Pin1 to recognize the substrate phosphate group, while the other end of the molecule formed many hydrophobic interactions with residues critical for recognizing Pro in the substrate (FIG. 32B).

Trans-RA Inhibited IL-33-Induced Pin1 Activation and Cytokine Secretion in Eosinophils.

To examine the effects of trans-RA on immune cells related to asthma, we stimulated BM-derived eosinophils with 100 ng/ml IL-33 and different levels of trans-RA. trans-RA induced Pin1 degradation (FIG. 33A) and inhibited Pin1 activation (FIG. 33B) and IL-6 secretion (FIG. 33C) induced by IL-33.

Proteinuria in NZBWF1 Mice is Significantly Reduced by Pin1 Inhibitor ATRA.

Our objective here was to determine if the Pin1 inhibitor we have discovered, ATRA, offer a treatment benefit in preclinical models of SLE. To this end we have been treating NZBWF1 female mice for 3.5 months with controlled release ATRA pellets, which have been well established pharmacologically and which offer the advantage ease of delivery, reduced stress to subjects and controlled drug release. Each cohort has been pre-bleed and urine collected before the start of drug treatment. Subsequently, we have collected serum and urine samples monthly for evaluation of disease markers such as autoantibodies and proteinuria. We have analyzed each cohort for proteinuria at 3.5 months of ATRA and noticed that the placebo cohort have significantly elevated urinary protein levels in comparison to ATRA treated mice (FIG. 34).

Cutaneous Inflammation is Reduced in Pin1 KO Mice.

We have compared the development of cutaneous inflammation induced by direct treatment with a TLR7 ligand formulated into a topical cream or injection of sera from lupus prone mice with active disease into both WT and KO Pin1 mice followed by histological analysis. Both of these models have been proposed to recapitulate forms of human cutaneous lupus with TLR signaling believed to contribute to disease pathogenesis. FIG. 35 shows representative images from H&E stained skin sections from Pin1 WT and KO mice induced with either lupus sera or TLR7 ligand. We noticed that WT mice developed considerably more significant inflammation than Pin1 KO mice for both types of inducer exemplified by thickening of the keratinocyte layer or hyperkeratosis (see arrows). Although we found inflammation in the Pin1 KO mice as compared to non-treated Pin1 KO the degree of kerationcyte thickening was considerably less than that identified in the Pin1 WT mice. These findings are consistent with our previous findings that Pin1 KO mice display a reduced TLR response.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of reducing elevated Pin1 activity in a subject having elevated levels of a Pin1 marker, comprising the step of administering to said subject a therapeutically effective amount of a retinoic acid compound, wherein said subject suffers from an immune disorder characterized by dysregulation of Toll-like receptor and/or type 1 interferon, and wherein said subject has elevated levels of a Pin1 marker.

2. A method of reducing elevated Pin1 activity in a subject, comprising the steps of determining Pin1 activity levels in a sample from said subject; and administering a therapeutically effective amount of a retinoic acid compound to said subject if said sample from said subject is determined to have elevated Pin1 activity levels, wherein said subject suffers from an immune disorder characterized by dysregulation of Toll-like receptor and/or type 1 interferon.

3. The method of claim 1, further comprising the administration of a second therapeutic compound, wherein said second therapeutic compound is an anti-inflammatory compound, anti-microbial compound, or anti-viral compound.

4. The method of claim 1, wherein said Pin1 activity is reduced by Ser71 phosphorylation of Pin1.

5. The method of claim 1, further comprising determining Pin1 activity levels in said sample after said administration of a retinoic acid compound.

6. The method of claim 1, wherein said retinoic acid compound is selected from the group consisting of 13-cis-retinoic acid and all-trans-retinoic acid.

7. The method of claim 1, wherein said retinoic acid compound is selected from the group consisting of retinol, retinyl acetate, retinal, and AC-55649.

8. The method of claim 1, wherein said sample is selected from the group consisting of blood, urine, tissue biopsies, lymph, saliva, phlegm, and pus.

9. The method of claim 1, wherein said elevated Pin1 activity level is due to an inherited trait or a somatic mutation.

10. The method of claim 3, wherein said second therapeutic compound is selected from the group consisting of corticosteroids, NSAIDs, COX-2 inhibitors, biologics, small molecule immunomodulators, non-steroidal immunophilin-dependent immunosuppressants, 5-amino salicylic acid, DMARDs, hydroxychloroquine sulfate, and penicillamine.

11. The method of claim 3, wherein said second therapeutic compound is selected from the group consisting of microtubule inhibitors, topoisomerase inhibitors, platins, alkylating agents, and anti-metabolites.

12. The method of claim 3, wherein said second therapeutic compound is selected from the group consisting of 1-D-ribofuranosyl-1,2,4-triazole-3 carboxamide, 9→2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

13. The method of claim 3, wherein said second therapeutic compound is administered at a low dosage.

14. The method of claim 3, wherein said retinoic acid compound and said second therapeutic compound are formulated together.

15. The method of claim 1, wherein said immune disorder is related to increased susceptibility to infection.

16. The method of claim 1, wherein said immune disorder is selected from the group consisting of acne vulgaris; acute respiratory distress syndrome; Addison's disease; adrenocortical insufficiency; adrenogenital ayndrome; allergic conjunctivitis; allergic rhinitis; allergic intraocular inflammatory diseases, ANCA-associated small-vessel vasculitis; angioedema; ankylosing spondylitis; aphthous stomatitis; arthritis, asthma; atherosclerosis; atopic dermatitis; autoimmune disease; autoimmune hemolytic anemia; autoimmune hepatitis; Behcet's disease; Bell's palsy; berylliosis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; epicondylitis; erythema nodosum; exfoliative dermatitis; fibromyalgia; focal glomerulosclerosis; giant cell arteritis; gout; gouty arthritis; graft-versus-host disease; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflammatory bowel or gastrointestinal disorders, inflammatory dermatoses; juvenile rheumatoid arthritis; laryngeal edema; lichen planus; Loeffler's syndrome; lupus nephritis; lupus vulgaris; lymphomatous tracheobronchitis; macular edema; multiple sclerosis; musculoskeletal and connective tissue disorder; myasthenia gravis; myositis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary billiary cirrhosis; pruritus scroti; pruritis/inflammation, psoriasis; psoriatic arthritis; Reiter's disease; relapsing polychondritis; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis.

17. The method of claim 1, wherein said immune disorder results from dysregulation of Toll-like receptor signaling or type I interferon-mediated immunity.

18. The method of claim 13, wherein said retinoic acid compound and said second therapeutic compound are formulated together.

19. The method of claim 1, wherein said immune disorder is selected from the group consisting of acne vulgaris; acute respiratory distress syndrome; Addison's disease; adrenocortical insufficiency; adrenogenital ayndrome; allergic conjunctivitis; allergic rhinitis; allergic intraocular inflammatory diseases, ANCA-associated small-vessel vasculitis; angioedema; aphthous stomatitis; atherosclerosis; atopic dermatitis; autoimmune hemolytic anemia; autoimmune hepatitis; Bell's palsy; berylliosis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; Cushing's syndrome; dermatomyositis; discoid lupus erythematosus; eosinophilic fasciitis; epicondylitis; erythema nodosum; exfoliative dermatitis; focal glomerulosclerosis; giant cell arteritis; gout; gouty arthritis; Henoch-Schonlein purpura; herpes gestationis; hirsutism; hypersensitivity drug reactions; idiopathic cerato-scleritis; idiopathic pulmonary fibrosis; idiopathic thrombocytopenic purpura; laryngeal edema; Loeffler's syndrome; lupus nephritis; lupus vulgaris; lymphomatous tracheobronchitis; macular edema; musculoskeletal and connective tissue disorder; myositis; obstructive pulmonary disease; ocular inflammation; osteoarthritis; pancreatitis; pemphigoid gestationis; pemphigus vulgaris; polyarteritis nodosa; polymyalgia rheumatica; primary adrenocortical insufficiency; primary biliary cirrhosis; pruritus scroti; pruritis/inflammation, psoriatic arthritis; Reiter's disease; relapsing polychondritis; rheumatic carditis; rheumatic fever; rosacea caused by Sweet's syndrome; rosacea caused by zoster-associated pain; segmental glomerulosclerosis; serum sickness; shoulder tendinitis or bursitis; Still's disease; Sweet's disease; systemic dermatomyositis; systemic sclerosis; Takayasu's arteritis; temporal arteritis; toxic epidermal necrolysis; tuberculosis; uveitis; vasculitis; and Wegener's granulomatosis.

20. The method of claim 1, wherein said immune disorder is asthma, systemic lupus erythematosus, or rheumatoid arthritis.

* * * * *

UNITED STATES PATENT AND TRADEMARK OFFICE
CERTIFICATE OF CORRECTION

PATENT NO. : 9,439,884 B2
APPLICATION NO. : 14/122611
DATED : September 13, 2016
INVENTOR(S) : Kun Ping Lu et al.

It is certified that error appears in the above-identified patent and that said Letters Patent is hereby corrected as shown below:

On the Title Page

In the title, replace "METHODS FOR THE TREATMENT OF IMMUNE DISORDERS" with --METHODS AND COMPOSITIONS FOR THE TREATMENT OF IMMUNE DISORDERS--.

In the Drawings

In Figure 29D, replace "eiosinophils" with --eosinophils--.

In the Specification

Column 1, Lines 1-2, replace "METHODS FOR THE TREATMENT OF IMMUNE DISORDERS" with --METHODS AND COMPOSITIONS FOR THE TREATMENT OF IMMUNE DISORDERS--;
    Line 42, replace "pruritis/inflammation" with --pruritus/inflammation--.

Column 2, Line 56, replace "retinol acetate" with --retinyl acetate--;
    Line 62, replace "disregulation" with --dysregulation--;
    Line 66, replace "ayndrome" with --syndrome--.

Column 3, Line 27, replace "billiary" with --biliary--;
    Line 28, replace "pruritis/inflammation" with --pruritus/inflammation--;
    Line 64, replace "fee" with --free--.

Column 4, Line 59, replace "pyrazine, pyrazine, triazine" with --pyrazine, triazine--.

Column 5, Line 57, replace "flupredidene" with --fluprednidene--.

Signed and Sealed this
Third Day of October, 2017

Joseph Matal
*Performing the Functions and Duties of the
Under Secretary of Commerce for Intellectual Property and
Director of the United States Patent and Trademark Office*

Column 6, Line 45, replace "ng/mL, LPS," with --ng/mL LPS,--.

Column 7, Line 9, replace "staining Specific" with --staining. Specific--;
    Line 18, replace "and TRAM" with --and IRAK1--;
    Line 31, replace "experiments" with --experiments.--;
    Line 52, replace "by Pin1" with --by Pin1.--;
    Line 56, replace "Ser131. Ser144, and Ser173" with --Ser131, Ser144, and Ser173--.

Column 9, Line 42, replace "shown below the graph (t)" with --shown below the graph (f)--.

Column 10, Line 41, replace "negative selection sing MACS beads" with
        --negative selection using MACS beads--;
    Line 55, replace "pDCs isolated form spleens" with --pDCs isolated from spleens--.

Column 11, Line 13, replace "Pin-IRAK1" with --Pin1-IRAK1--;
    Line 19, replace "IRAK2, and IRAk4" with --IRAK2, and IRAK4--;
    Line 39, replace "FLAG IRAK1" with --FLAG-IRAK1--;
    Line 53, replace "IRAK null 293 cells" with --IRAK1 null 293 cells--;
    Line 58, replace "GST-Pin1 PD was" with --GST-Pin1. PD was--;
    Lines 62-63, replace "IRAK1 activation in response to activation in response to activation of
        TRL2" with --IRAK1 activation in response to activation of TLR2--.

Column 12, Lines 13-14, replace "Pin1+/+ and Pin1-/- Flt3" with --Pin1 +/+ and Pin1 -/- Flt3--;
    Line 16, replace "MAPL" with --MAPK--;
    Lines 18-19, replace "Pin1+/+ and Pin1-/- Flt3" with --Pin1 +/+ and Pin1 -/- Flt3--;
    Line 21, replace "MAPL" with --MAPK--;
    Line 26, replace "macrophages form Pin1 WT" with --macrophages from Pin1 WT--;
    Line 60, replace "but nor KO" with --but not KO--.

Column 13, Line 32, replace "umol" with --μmol--;
    Line 51, replace "were crossed with CMV-Flp mice of delete the" with --were crossed with
        CMV-Flp mice to delete the--;
    Lines 59-60, replace "we identified ATRA and Cpd4 ad new Pin1 inhibitors." with
        --we identified ATRA and Cpd4 as new Pin1 inhibitors.--.

Column 14, Line 42, replace "more efficiently that cis-RA." with --more efficiently than cis-RA.--;
    Line 43, replace "Dose-dependant" with --Dose-dependent--;
    Line 48, replace "cells, but nor in" with --cells, but not in--;
    Lines 55-56, replace "carboxylic acid, but not other groups potently" with
        --carboxylic acid, but not other groups, potently--.

Column 15, Line 1, replace "eosionophils" with --eosinophils--;
    Lines 29-30, replace "disregulation" with --dysregulation--;
    Line 35, replace "compounds" with --compounds.--;

CERTIFICATE OF CORRECTION (continued)  Page 3 of 4
U.S. Pat. No. 9,439,884 B2

Lines 47-48, replace "phosphoserinelthreonine-proline." with --phosphoserine/threonine-proline--;

Line 54, replace "antiviral responses" with --antiviral response--.

Column 16, Line 7, replace "The WW domain acts a novel" with --The WW domain acts as a novel--;

Line 20, replace "in a subject; where" with --in a subject, where--.

Column 17, Line 33, replace "'Molecular Biology," is Elsevier Science'" with --Molecular Biology," Elsevier Science--;

Lines 45-46, replace "or other genes that effect Pin1" with --or other genes that affect Pin1--.

Column 18, Line 7, replace "can be readily be adapted" with --can be readily adapted--;

Lines 64-65, replace "billiary" with --biliary--;

Line 65, replace "pruritis/inflammation" with --pruritus/inflammation--.

Column 19, Line 50, replace "and to explain some patients may not respond to RA" with --and to explain why some patients may not respond to RA--.

Column 20, Line 60, replace "hundreds or thousands of oligonucleotides probes" with --hundreds or thousands of oligonucleotide probes"--.

Column 22, Line 42, replace "Nature 324:163); Saiki et al." with --Nature 324:163; Saiki et al--.

Column 24, Line 6, replace "inflixamab, adelimumab" with --infliximab, adalimumab--;

Line 22, replace "ceforanid" with --ceforanide--;

Lines 47-48, replace "(e.g., at least 5% less (e.g., at least 10%, 20%, 50%, 80%, 90%, or even 95%) less than when the anti-inflammatory compound is administered alone." with --(e.g., at least 5% less (e.g., at least 10%, 20%, 50%, 80%, 90%, or even 95% less) than when the anti-inflammatory compound is administered alone).--.

Column 25, Line 52, replace "Ligation" with --Ligation.--.

Column 27, Line 8, replace "deletion of the UD, abolished Pin1" with --deletion of the UD abolished Pin1--;

Lines 31-32, replace "predominately" with --predominantly--;

Line 52, replace "typsin" with --trypsin--;

Line 54, replace "(FIG. 14e)" with --(FIG. 14c)--.

Column 29, Line 26, replace "Pin 1" with --Pin1--;

Line 38, replace "Pin 1" with --Pin1--;

Line 64, replace "(time constant minutes)" with --(time constant ~ minutes)--.

Column 30, Line 29, replace "MyD88lIRAK4" with --MyD88/IRAK4--;

Line 40, replace "FLAGIRAK1" with --FLAG-IRAK1--;

CERTIFICATE OF CORRECTION (continued)
U.S. Pat. No. 9,439,884 B2

Line 32, replace "IFN-α. to translocate" with --IFN-α, to translocate--;
Line 47, replace "(FIG. 4a, Thus it appears" with --(FIG. 4a, 5a). Thus it appears--;
Line 62, replace "Pin1 WT. but not" with --Pin1 WT, but not--.

Column 31, Line 11, replace "In contrast. IRF7" with --In contrast, IRF7--;
Line 21, replace "IRAK" with --IRAK1--.

Column 32, Line 4, replace "CD8 T-cell" with --$CD8^+$ T-cell--.

Column 33, Line 46, replace "Previously a leader in human SLE genetics, and we established" with --Previously a leader in human SLE genetics, we established"--.

Column 34, Lines 9-10, replace "(Allophycocyanin) The labeled" with --(Allophycocyanin). The labeled--;
Line 38, replace "express Pin." with --express Pin1.--;
Line 55, replace "PMBCs" with --PBMCs--.

Column 35, Line 18, replace "with only a moderate effects on" with --with only a moderate effect on--;
Lines 52-53, replace "Pin1 peptidic inhibitor, pTide to identify" with --Pin1 peptidic inhibitor, pTide, to identify--.

Column 36, Line 34, replace "has been pre-bleed" with --has been pre-bled--;
Line 58, replace "kerationcyte" with --keratinocyte--.

In the Claims

Column 38, Line 14, replace "adrenogenital ayndrome" with --adrenogenital syndrome--;
Line 43, replace "billiary" with --biliary--;
Line 43, replace "pruritis/inflammation" with --pruritus/inflammation--;
Line 67, replace "adrenogenital ayndrome" with --adrenogenital syndrome--.

Column 40, Lines 4-5, replace "billiary" with --biliary--;
Line 5, replace "pruritis/inflammation" with --pruritus/inflammation--.